(12) United States Patent
White et al.

(10) Patent No.: US 12,367,951 B1
(45) Date of Patent: Jul. 22, 2025

(54) OPTIMIZING MOLECULE TOXICITY BY REPLACING TARGET FRAGMENTS WITH BIOISOSTERES

(71) Applicant: AXIOMBIO, INC., San Francisco, CA (US)

(72) Inventors: Brandon White, San Francisco, CA (US); Alexander Bremner Upjohn Beatson, San Francisco, CA (US); Katherine Lynn Titterton, San Francisco, CA (US); Daniil Boiko, San Francisco, CA (US); Ángel Alexander Cabrera, San Francisco, CA (US); Alex Tim Bäuerle, San Francisco, CA (US)

(73) Assignee: AxiomBio, Inc., San Francisco, CA (US)

( * ) Notice: Subject to any disclaimer, the term of this patent is extended or adjusted under 35 U.S.C. 154(b) by 0 days.

(21) Appl. No.: 19/009,895

(22) Filed: Jan. 3, 2025

Related U.S. Application Data

(60) Provisional application No. 63/651,057, filed on May 23, 2024, provisional application No. 63/563,254, filed on Mar. 8, 2024.

(51) Int. Cl.
  *G16C 20/30* (2019.01)
  *G16C 20/70* (2019.01)
  *G16C 20/90* (2019.01)

(52) U.S. Cl.
  CPC .............. *G16C 20/30* (2019.02); *G16C 20/70* (2019.02); *G16C 20/90* (2019.02)

(58) Field of Classification Search
  CPC ........ G16C 20/30; G16C 20/70; G16C 20/90; G06V 10/82
  See application file for complete search history.

(56) References Cited

U.S. PATENT DOCUMENTS

| | | | |
|---|---|---|---|
| 2013/0144584 A1* | 6/2013 | Chen ...................... | G16C 20/30 703/11 |
| 2019/0080057 A1* | 3/2019 | Stanley .................. | G06V 10/82 |

OTHER PUBLICATIONS

Athey et al., "Generalized Random Forests," CoRR, Submitted on Jul. 6, 2017, arXiv:1610.01271v3, 47 pages.

(Continued)

*Primary Examiner* — Lam S Nguyen
(74) *Attorney, Agent, or Firm* — Fish & Richardson P.C.

(57) ABSTRACT

Methods, systems, and apparatus, including computer programs encoded on a computer storage medium, for predicting toxicity of molecules. In one aspect, a method comprises: obtaining data identifying: (i) an input molecule, and (ii) a target molecule fragment; determining, for each candidate molecule fragment in a database of candidate molecule fragments, a respective similarity measure between: (i) an embedding of the target molecule fragment, and (ii) an embedding of the candidate molecule fragment; selecting a plurality of candidate molecule fragments for inclusion in a set of alternative molecule fragments based on the similarity measures; and generating data defining a plurality of modified molecules, wherein each modified molecule is a modified version of the input molecule where the target molecule fragment is replaced by a respective alternative molecule fragment from the set of alternative molecule fragments; and generating a respective toxicity prediction for each of the plurality of modified molecules.

20 Claims, 34 Drawing Sheets

(56) References Cited

OTHER PUBLICATIONS

Bray et al., "Cell Painting, a high-content image-based assay for morphological profiling using multiplexed fluorescent dyes," Nature Protocols, Aug. 25, 2016, 11(9):1757-1774.
Breiman, "Random Forests," Machine Learning, 2001, 45:5-32.
Gilmer et al., "Neural Message Passing for Quantum Chemistry," CoRR, Submitted on Apr. 4, 2017, arXiv:1704.01212v1, 13 pages.
Goodfellow et al., "Generative Adversarial Networks," CoRR, Submitted on Jun. 10, 2014, arXiv:1406.2661v1, 9 pages.
Mikolov et al., "Efficient Estimation of Word Representations in Vector Space," CoRR, Submitted on Sep. 7, 2013, arXiv:1301.3781v3, 12 pages.
Radford et al., "Learning Transferable Visual Models From Natural Language Supervision," CoRR, Submitted on Feb. 26, 2021, arXiv:2103.00020v1, 48 pages.
Rombach et al., "High-Resolution Image Synthesis with Latent Diffusion Models," CoRR, Submitted on Apr. 13, 2022, aXiv:2112.10752v2, 45 pages.
Ronneberger et al., "U-Net: Convolutional Networks for Biomedical Image Segmentation," CoRR, Submitted on May 18, 2015, arXiv:1505.04597v1, 8 pages.

\* cited by examiner

300

┌─────────────────────────────────────┐
│ PROCESS A REPRESENTATION OF A CHEMICAL │
│ STRUCTURE OF THE INPUT MOLECULE USING A │
│ MOLECULE EMBEDDING NEURAL NETWORK TO │ — 302
│ GENERATE AN EMBEDDING OF THE INPUT │
│ MOLECULE │
└─────────────────────────────────────┘
                  ↓
┌─────────────────────────────────────┐
│ INCLUDE THE EMBEDDING OF THE INPUT  │ — 304
│ MOLECULE IN THE MODEL INPUT TO THE TOXICITY │
│ PREDICTION MACHINE LEARNING MODEL   │
└─────────────────────────────────────┘

FIG. 3A

Reagents

| Name | Supplier | Catalog # | Storage |
|---|---|---|---|
| Collagen I, Rat Tail (Lot 991343A) | Thermo Fisher | A10483-01 | 4°C |
| Collagen I, Rat | Corning via Fisher Scientific | 11563550 / Corning 354236 | 4°C |
| Acetic Acid | Carl Roth | 3738.1 | |
| Male Human Hepatocytes – Individual, Cryoplatable | BioIVT | M00995-P, Lot: INM, AW ID: s0600174 | <-150°C, N₂ (l) tank |
| LIVERPOOL®* Mixed Gender Human Hepatocytes – 5-Donor Pool, Cryoplateable | BioIVT | X008052-P | Lot: BSS, AW ID: s0617818 | <-150°C, N₂ (l) tank |
| INVITROGRO CP Medium | BioIVT | Z99029, Lot: C07123D | 4°C |
| TORPEDO Antibiotic Mix | BioIVT | Z99000, Lot: C06103A | -20°C, aliquot à 1 ml |
| DPBS (w/o Ca²⁺, Mg²⁺) | PAN-Biotech | P04-36500 | RT |
| CyQUANT™ LDH Cytotoxicity Assay Kit | Invitrogen | C20300/1 | -20°C |
| RealTime-Glo MT Cell Viability Assay | Promega | G9713 | -20°C |
| PhenoVue reagent dye diluent A (5x) | Revvity | PVDDA1 | RT |
| PhenoVue 641 Mitochondrial stain | Revvity | CP3D1 #08A | -20°C |
| PhenoVue Flour 555 -WGA | Revvity | CP1551 #02A | -20°C |
| PhenoVue Flour 488 Concanavalin A | Revvity | CP94881 #03B | -20°C |
| PhenoVue Flour 568 Phalloidin | Revvity | CP25681 #04A | -20°C |
| PhenoVue 512 nucleic acid stain | Revvity | CP61 #03A | -20°C |
| PhenoVue Hoechst 33342 nuclear Stain | Revvity | CP71 #01B | 4°C |
| HBSS (10X), w/calcium and magnesium, no phenol red | Fisher Scientific | 14065056 | RT |
| Antimycotic/Antibiotic (AA) | Sigma-Aldrich | A5955 | 4°C |
| 32% Paraformaldehyde solution | Science Services | E15740 | RT |
| DMSO | Carl Roth | 4720 | RT |

Plates/Plasticware

| Name | Supplier | Catalog # |
|---|---|---|
| Cell plate: 384-well High Content Imaging, Low base | Corning | 4518 |
| Filter units, 0.2 µm PES (500 ml) | FisherScientific | 10229090 |
| 50 ml conical tubes PP | Greiner BioOne | 227261 |
| 250 ml conical tubes PP | Corning | 430776 |
| CyBio RoboTipTray 384/60 µL | Analytic Jena | OL3810-25-244 |
| 384 Automation Reservoirs, sterile | FisherScientific | 10141443 |
| LDH Assay Plate: Greiner 384 | Greiner BioOne | 781101 |
| Echo Master Plate: 384-well Microplate COC LDV; barcoded | Labcyte | LP0200 |
| Library plate, 10 mM COC plates BAI Plus | Assay.Works | |
| Compound ARP: Greiner plate | Greiner BioOne | 784201 |

FIG. 18A

Specialized Equipment

| Type | Name & Description |
|---|---|
| Multichannel dispenser | Multidrop Combi, Thermo Fisher |
| 384-Well liquid handler | CyBio-Felix w/ 384-well head, Analytik Jena |
| Corning Cell Counter | Corning |
| Cell Plate Incubator | Cytomat, Thermo Fisher (plate racks on a rotating platform) |
| Luminescence microplate reader | EnVision Multimode Detector, PerkinElmer (now Revvity) |
| High content imager | Operetta CLS, PerkinElmer (now Revvity) |
| Nanoliter dispenser | Labcyte ECHO550 |
| Microplate reader | SPECTROstar Nano, BMG |
| Microplate washer | Biotek |
| Automation Platform | "Hit Works", Analytic Jena (custom integrated platform) |
| MicroPure water purifier | Thermo Fisher Scientific |

Additional Materials and Equipment

- 10% Ethanol, 70% Ethanol
- Sterile, disposable pipettes
- Table-top centrifuge, tube shaker, pH meter

FIG. 18B

20 mM Acetic Acid

|  |  |  |  |
|---|---|---|---|
| Acetic Acid | 17 M | 850 | 590 µl |
| Millipore H₂O |  |  | 500 ml |

Sterile filter before use

Collagen solution 50 µg/ml

|  |  |  |  |
|---|---|---|---|
| Collagen I, rat tail | 3 mg / ml | 60 | 1.6 ml |
| 20 mM Acetic Acid |  |  | 98.4 ml |

Complete CP medium

|  |  |
|---|---|
| INVITROGRO CP medium | Supplemented with |
| TORPEDO Antibiotic Mix | 45x stock, e.g., add 5.5 ml to 250 ml or 1ml to 45 ml CP medium |

Medium expires 7 days after addition of antibiotic mix.

1x MT-Glo Reagent

Prewarm to 37 °C: Complete CP Medium in water bath, MT Cell viability substrate and NanoLuc®Enzyme in incubator.

|  |  |  |  |  |
|---|---|---|---|---|
| Complete CP Medium |  |  |  | 125 ml |
| MT Cell viability substrate | 1000x | 0.5x | 1000 | 125 µl |
| NanoLuc®Enzyme | 1000x | 0.5x | 1000 | 125 µl |

*17 plates

LDH reaction mixture

Prepare one day prior to run and freeze.

|  |  |
|---|---|
| H₂O dest | 11.4 ml |
| LDH substrate | 1 vial |
| LDH Reagent buffer | 600 µl |

For 17 plates: prepare 72 ml ≅ 6 vials

Staining Buffer 1x

|  |  |  |
|---|---|---|
| Diluent A 5x | 1x | 28 ml |
| Triton 20% | 0.3% (dilF 66.6) | 2.1 ml |
| H₂O dest |  | 112 ml |

*17 plates

≅ Mix & filter (with 0.2 µm filter unit)

MitoTracker Stain 2x

Prewarm Complete CP Medium to 37°C in a water bath before adding Mitotracker.

|  |  |  |  |  |
|---|---|---|---|---|
| Complete CP medium |  |  |  | 140 mL |
| PhenoVue 641 Mitochondrial stain (final 500 nM) | 1 mM |  | 1000 nM | 1000 | 140 µl |

*17 plates

FIG. 19A

16% PFA/Water

| Name | | | | C (μL) |
|---|---|---|---|---|
| Milli-Q water | | | | 45 mL |
| Paraformaldehyde (PFA) | 32% | 16% | 2 | 45 mL |

*17 plates

Cell Painting Stain

Vortex and spin down the dyes prior to use, especially ConA solution contains precipitate ☒ avoid adding to the mixture

| Name | Stock conc. | Final conc. | Required Dilution Factor | C (μL) |
|---|---|---|---|---|
| Staining buffer 1x | | | | 140 ml |
| PhenoVue Fluor 555 WGA (final 1.5 μg/ml) | 1 mg/ml | 3 μg/ml | 333 | 420 μl |
| PhenoVue Fluor 488 Concanavalin A (final 5 μg/ml) | 2 mg/ml | 10 μg/ml | 200 | 700 μl |
| PhenoVue Fluor 568 Phalloidin (final 8.25 nM) | 6.6 μM | 16.5 nM | 400 | 350 μl |
| RNA 512 (final 1 μM) | 5 mM | 2 μM | 2500 | 56 μl |
| Hoechst 33342 (final 1 μg/ml) | 10 mg/ml | 2 μg/ml | 5000 | 28 μl |

*17 plates

1x HBSS

| Component | Concentration |
|---|---|
| H₂O | Supplemented with |
| 10x HBSS | 1x |

Adjust pH to 7.2 with 1 M NaOH

1x HBSS/AA

| Component | Concentration |
|---|---|
| 1x HBSS | Supplemented with |
| AA | 1:100 |

| 100µM Start / 500nL / 1:3 | | | | |
|---|---|---|---|---|
| Plate-Name | Source (10mM) | final conc. (µM) | DMSO backfill | print direction |
| P1 | 500nL | 100 | 0 nL | meander by row |
| P2 | 167.5nL | 33.5 | 332.5nL | zigzag by column |
| P3 | 55nL | 11 | 445nL | zigzag by row |
| P4 | 17.5nL | 3.5 | 482.5nL | meander by column |
| P5 | 5nL | 1 | 495nL | meander by row |
| Intermediate (i1): 25nL (Source) + 6000nL DMSO (41.4938µM) | | | | |
| Plate-Name | Source (i1) | final conc. (µM) | DMSO backfill | print direction |
| P6 | 495nL | 0.4108 | 5nL | zigzag by column |
| P7 | 165nL | 0.1369 | 335nL | zigzag by row |
| P8 | 55nL | 0.0456 | 445nL | meander by column |

Vol.Source (S): 745 + 25 + 2.5 = 770nL
Vol. Intermediate 1 (i1): 715nL

FIG. 24

OPTIMIZING MOLECULE TOXICITY BY REPLACING TARGET FRAGMENTS WITH BIOISOSTERES

CROSS-REFERENCE TO RELATED APPLICATIONS

This application claims priority to U.S. Provisional Application No. 63/651,057, filed on May 23, 2024, and U.S. Provisional Application No. 63/563,254, filed on Mar. 8, 2024. The disclosures of the prior applications are considered part of and are incorporated by reference in the disclosure of this application.

BACKGROUND

This specification relates to predicting toxicity of molecules.

Predictions can be made using machine learning models. Machine learning models receive an input and generate an output, e.g., a predicted output, based on the received input. Some machine learning models are parametric models and generate the output based on the received input and on values of the parameters of the model. Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system implemented as computer programs on one or more computers in one or more locations that can predict a toxicity of a molecule. The toxicity of a molecule can represent a measure of harm or damage that the molecule can cause to a cell or a group of cells, when the cell or group of cells is exposed to the molecule.

A molecule includes two or more atoms bonded together. Examples of molecules include small molecules (e.g., having a molecular weight of less than 900 daltons), proteins, nucleic acids, polysaccharides, lipids, etc.

The toxicity of a molecule can be characterized along different dimensions, e.g., cell morphology changes, membrane integrity (e.g., a measure of lactate dehydrogenase (LDH)), metabolic activity (e.g., a measure of adenosine triphosphate (ATP)), apoptosis, necrosis, a cell count, or a percent cell viability measuring the proportion of cells that are alive in a cell culture exposed to the molecule relative to the cell culture prior to exposure to the molecule.

The toxicity of a molecule can be characterized using, for example, using cytotoxicity assays that measure the extent to which the molecule harms or kills cells, e.g., by evaluating biochemical readouts indicating cell membrane integrity, metabolic activity, apoptosis, or necrosis. Some examples of cytotoxicity assays include Methylthiazolyldiphenyl-tetrazolium Bromide (MTT) assays, Lactate Dehydrogenase (LDH) assays, or flow cytometry. The toxicity of a molecule can also be characterized by cell viability assays that measure the ability of cells to survive and remain metabolically active after exposure to the molecule, e.g., by evaluating the number or proportion of cells that are alive, or biochemical readouts indicating the ability of cells to maintain metabolic activity. Some examples of cell viability assays include MTT assays or adenosine triphosphate (ATP) bioluminescence assays.

The toxicity of a molecule can also be characterized using various imaging-based metrics such as a cell morphology changes (e.g., a proportion of cells or magnitude of visual changes in mitochondrial phenotype such as mitochondrial swelling or fission, cell shape, nuclei size, lipid accumulation, or cytoplasmic vacuolation), a proportion of cells or magnitude of visual changes in membrane integrity, a proportion of cells or magnitude of visual changes in metabolic activity, a proportion of cells or magnitude of visual changes indicating apoptosis, a proportion of cells or magnitude of visual changes indicating necrosis, or a cell count.

According to one aspect, there is provided a method performed by one or more computers, the method comprising: obtaining data identifying an input molecule; generating a toxicity dose-response curve for the input molecule using a toxicity prediction machine learning model, comprising: for each dose value in a sequence of dose values: generating a model input to the toxicity prediction machine learning model that comprises: (i) a set of features characterizing the input molecule, and (ii) the dose value; and processing the model input using the toxicity prediction machine learning model and in accordance with values of a set of machine learning model parameters to generate a toxicity prediction for the input molecule at the dose value; generating the toxicity dose-response curve for the input molecule based on the toxicity predictions for the sequence of dose values; and outputting the toxicity dose-response curve for the input molecule.

In some implementations, generating the toxicity dose-response curve for the input molecule based on the toxicity predictions for the sequence of dose values comprises: generating the toxicity dose-response curve by interpolating between the toxicity predictions generated by the toxicity prediction machine learning model.

In some implementations, the toxicity dose-response curve is a continuous curve that defines a respective toxicity prediction for each dose value in a continuous range of possible dose values.

In some implementations, outputting the toxicity dose-response curve for the input molecule comprises: presenting a visual representation of the toxicity dose-response curve on a display of a user device.

In some implementations, the toxicity prediction machine learning model has been trained by operations comprising: generating a set of training examples, wherein each training example comprises: (i) a training input that includes a set of features characterizing a training molecule and a dose value, and (ii) a target toxicity; and training the toxicity prediction machine learning model on the set of training examples by a machine learning training technique.

In some implementations, training the toxicity prediction machine learning model on the set of training examples by the machine learning training technique comprises, for each training example: training the toxicity prediction machine learning model to reduce a discrepancy between: (i) a toxicity prediction generated by the toxicity prediction machine learning model by processing the training input of the training example, and (ii) the target toxicity of the training example.

In some implementations, for each of one or more training examples in the set of training examples, the target toxicity for the training example is generated by performing operations comprising: obtaining one or more images of a cell culture that has been exposed to the training molecule of the training example at the dose value specified by the training example; processing the one or more images of the cell culture to generate the target toxicity for the training example.

In some implementations, the one or more images of the cell culture comprise fluorescence microscopy images that include multiple fluorescence channels that correspond to different cellular structures; wherein the fluorescence microscopy image is captured after the cell culture has been stained with a panel of fluorescent dyes that mark various cellular structures.

In some implementations, processing the one or more images of the cell culture to generate the target toxicity for the training example comprises: determining the target toxicity for the training example based on one or more of: a number of cells in the cell culture, morphological features of organelles in cells in the cell culture, or a size of cells in the cell culture.

In some implementations, processing the one or more images of the cell culture to generate the target toxicity for the training example comprises: processing the one or more images of the cell culture using an image processing neural network to generate a segmentation of the one or more images of the cell culture; and determining the target toxicity for the training example based at least in part on the segmentation of the one or more images of the cell culture.

In some implementations, for each of one or more training examples in the set of training examples, the target toxicity for the training example is generated by performing operations comprising: obtaining results of one or more biochemical assays performed on a cell culture that has been exposed to the training molecule of the training example at the dose value specified by the training example; and determining the target toxicity for the training example based on the results of the one or more biochemical assays.

In some implementations, the one or more biochemical assays include a cytotoxicity assay, or a cell viability assay, or both.

In some implementations, for each of one or more training examples in the set of training examples: the target toxicity of the training example is determined based on a toxicity measurement of a cell culture that has been exposed to the training molecule of the training example at the dose value specified by the training example; the cell culture corresponding to the training example is located in a target well in a multi-well plate; and the toxicity measurement of the cell culture is normalized based on a spatial location in the multi-well plate of the target well that holds the cell culture.

In some implementations, normalizing the toxicity measurement of the cell culture based on the spatial location in the multi-well plate of the target well that holds the cell culture comprises: obtaining control toxicity measurements for each of a plurality of control wells in the multi-well plate; training a normalization machine learning model to, for each control well in the multi-well plate, process a model input that defines a spatial location of the control well to generate a prediction for the control toxicity measurement for the control well; and normalizing the toxicity measurement of the cell culture in the target well using the normalization machine learning model.

In some implementations, normalizing the toxicity measurement of the cell culture in the target well using the normalization machine learning model comprises: processing a model input that defines a spatial location of the target well using the normalization machine learning model to generate a prediction for a control toxicity measurement for the target well; and normalizing the toxicity measurement of the cell culture in the target well based on the prediction for the control toxicity measurement for the target well.

In some implementations, normalizing the toxicity measurement of the cell culture in the target well based on the prediction for the control toxicity measurement for the target well comprises: dividing the toxicity measurement of the cell culture in the target well by the prediction for the control toxicity measurement for the target well that was generated by the normalization machine learning model.

In some implementations, generating the model input to the toxicity prediction machine learning model comprises: processing a representation of a chemical structure of the input molecule using a molecule embedding neural network to generate an embedding of the input molecule; and including the embedding of the input molecule in the model input to the toxicity prediction machine learning model.

In some implementations, the molecule embedding neural network has been jointly trained with an image embedding neural network; and wherein the image embedding neural network is configured to process a set of one or more images to generate an embedding of the set of images.

In some implementations, the joint training of the molecule embedding neural network and the image embedding neural network is performed by operations comprising: obtaining a set of molecule-image pairs, wherein each molecule-image pair comprises: (i) chemical structure data for a molecule, and (ii) a set of one or more images of a cell culture that has been exposed to the molecule; jointly training the molecule embedding neural network and the image embedding neural network on the set of molecule-image pairs to optimize a contrastive objective function.

In some implementations, for each molecule and each set of one or more images that are included in a same molecule-image pair, the contrastive objective function encourages an increase in similarity between: (i) an embedding of the molecule that is generated by the molecule embedding neural network, and (ii) an embedding of the set of images that is generated by the image embedding neural network.

In some implementations, for each molecule and each set of one or more images that are not included in a same molecule-image pair, the contrastive objective function encourages a decrease in similarity between: (i) an embedding of the molecule that is generated by the molecule embedding neural network, and (ii) an embedding of the set of images that is generated by the image embedding neural network.

In some implementations, the contrastive objective function further encourages: (i) an increase in similarity between respective embeddings of differently transformed versions of images that are included in a same molecule-image pair; and (ii) a decrease in similarity between respective embeddings of images that are included in different molecule-image pairs.

In some implementations, the toxicity prediction machine learning model comprises one or more of: a decision tree ensemble, or a neural network, or a support vector machine.

In some implementations, the method further comprises selecting the input molecule for physical synthesis based at least in part on the toxicity dose-response curve.

In some implementations, the method further comprises further comprising physically synthesizing the input molecule in response to selecting the input molecule for physical synthesis based at least in part on the toxicity dose-response curve.

In some implementations, the method further comprises performing a physical experiment to measure an experimental toxicity of the input molecule.

According to another aspect, there is provided a method performed by one or more computers, the method comprising: obtaining data identifying: (i) an input molecule, and (ii) a target molecule fragment of the input molecule; generating a set of alternative molecule fragments by performing operations comprising: determining, for each candidate molecule fragment in a database of candidate molecule fragments, a respective similarity measure between: (i) an embedding of the target molecule fragment, and (ii) an embedding of the candidate molecule fragment; selecting a plurality of candidate molecule fragments from the database of candidate molecule fragments for inclusion in the set of alternative molecule fragments based on the similarity measures; and generating data defining a plurality of modified molecules, wherein each modified molecule is a modified version of the input molecule where the target molecule fragment is replaced by a respective alternative molecule fragment from the set of alternative molecule fragments; generating a respective toxicity prediction for each of the plurality of modified molecules; and outputting data identifying the plurality of modified molecules and the toxicity predictions for the plurality of modified molecules.

In some implementations, embeddings of the candidate molecule fragments in the database of candidate molecule fragments have been generated by performing operations comprising: training a neural network to perform a machine learning task, wherein the neural network comprises: an embedding subnetwork that is configured to process data identifying a set of input molecule fragments to generate a respective embedding of each input molecule fragment; and a prediction subnetwork that is configured to process the embeddings of the input molecule fragments to generate a network output; and determining the respective embedding of each candidate molecule fragment as the embedding generated by processing the candidate molecule fragment using the embedding subnetwork of the neural network.

In some implementations, the machine learning task comprises predicting an identity of a molecule fragment included in a training molecule based on identities of one or more other molecule fragments included in the training molecule.

In some implementations, the machine learning task comprises predicting an identity of a molecule fragment included in a training example based on both: (i) identifies of one or more other molecule fragments included in the training molecule, and (ii) a spatial arrangement of the one or more other molecule fragments included in the training molecule.

In some implementations, training the neural network to perform the machine learning task comprises: generating a set of training examples for training the neural network, comprising, for each training example: obtaining data identifying a training molecule; processing the data identifying the training molecule to identify a set of molecule fragments included in the training molecule; generating a training input for the training example, wherein the training input comprises all but one of the molecule fragments in the set of molecule fragments; and generating a target output for the training example, wherein the target output comprises the one molecule fragment excluded from the training input; and training the neural network on the set of training examples.

In some implementations, training the neural network on the set of training examples comprises, for each training example: processing molecule fragments included in the training input of the training example using the neural network to generate a score distribution over the database of candidate molecule fragments; and training the neural network to optimize an objective function that measures an error between: (i) the score distribution over the database of candidate molecule fragments, and (ii) a molecule fragment specified by the target output of the training example.

In some implementations, training the neural network to optimize the objective function comprises: backpropagating gradients of the objective function through the prediction subnetwork and into the embedding subnetwork of the neural network.

In some implementations, the objective function measures the error using a cross-entropy term.

In some implementations, the embedding subnetwork is parametrized by an array of embeddings that comprises a respective embedding for each candidate molecule fragment in the database of candidate molecule fragments; and wherein backpropagating gradients of the objective function through the prediction subnetwork and into the embedding subnetwork of the neural network comprises: backpropagating gradients through the array of embeddings that parametrize the embedding subnetwork of the neural network.

In some implementations, the embedding subnetwork of the neural network is configured to process data characterizing a respective chemical structure of each input molecule fragment in a set of input molecule fragments using one or more embedding neural network layers; and wherein backpropagating gradients of the objective function through the prediction subnetwork and into the embedding subnetwork of the neural network comprises: backpropagating gradients through the embedding neural network layers of the embedding subnetwork of the neural network.

In some implementations, the database of candidate molecule fragments has been generated by fragmenting a plurality of training molecules.

In some implementations, selecting a plurality of candidate molecule fragments from the database of candidate molecule fragments for inclusion in the set of alternative molecule fragments based on the similarity measures comprises: selecting a plurality of candidate molecular fragments with embeddings having highest similarity to the embedding of the target molecule fragment for inclusion in the set of alternative molecule fragments.

In some implementations, outputting data identifying the plurality of modified molecules and the toxicity predictions for the plurality of modified molecules comprises: determining a ranking of the plurality of modified molecules based at least in part on the toxicity predictions for the plurality of modified molecules.

In some implementations, the ranking of the plurality of modified molecule is based at least in part on one or more other properties in addition to toxicity, including one or more of: synthetic accessibility, binding affinity, or solubility.

In some implementations, the ranking of the plurality of modified molecules is a ranking from lowest toxicity to highest toxicity.

In some implementations, outputting data identifying the plurality of modified molecules and the toxicity predictions for the plurality of modified molecules further comprises: providing, for display on a user device, a visual representation of a ranked list of the plurality of modified molecules.

In some implementations, for each of the plurality of modified molecules, generating the respective toxicity prediction for the modified molecule comprises: processing a model input that characterizes the modified molecule using a toxicity prediction machine learning model to generate a model output that defines the toxicity prediction for the modified molecule.

In some implementations, the toxicity prediction machine learning model comprises a decision tree ensemble.

In some implementations, the method further comprises selecting a modified molecule from the plurality of modified molecules for physical synthesis based at least in part on the toxicity predictions.

In some implementations, the method further comprises physically synthesizing the modified molecule selected for physical synthesis.

In some implementations, the method further comprises performing a physical experiment to measure an experimental toxicity of the modified molecule.

According to another aspect, there is provided a method performed by one or more computers, the method comprising: obtaining data identifying an input molecule; generating data defining a toxicity analysis tree for the input molecule, wherein: each node in the toxicity analysis tree represents a respective molecule and is associated with data defining a toxicity prediction for the molecule represented by the node; a root node of the toxicity analysis tree represents the input molecule; and each child node of the toxicity analysis tree represents a child molecule that is generated by modifying a parent molecule represented by a parent node of the child node; wherein generating the toxicity analysis tree comprises iteratively expanding the toxicity analysis tree over a plurality of iterations, comprising, at each of one or more iterations: selecting a node in the toxicity analysis tree for expansion at the iteration based at least in part on the toxicity predictions for the nodes in the toxicity analysis tree; generating data defining a modified molecule by modifying a molecule represented by the selected node; determining a toxicity prediction for the modified molecule; and expanding the toxicity analysis tree by: (i) adding a new node representing the modified molecule to the toxicity analysis tree as a child node of the selected node, and (ii) associating the new node with the toxicity prediction for the modified molecule; and processing the toxicity analysis tree to generate a respective toxicity score for each of a plurality of molecule fragments in the input molecule that characterizes an impact of the molecule fragment on a toxicity of the input molecule.

In some implementations, generating data defining the modified molecule by modifying the molecule represented by the selected node comprises: removing a molecule fragment from the molecule represented by the selected node.

In some implementations, generating data defining the modified molecule by modifying the molecule represented by the selected molecule comprises: replacing a molecule fragment from the molecule represented by the selected node with a new molecule fragment.

In some implementations, at each of one or more iterations, expanding the toxicity analysis tree comprises: adding a plurality of new child nodes to a node in the toxicity analysis tree that is selected for expansion at the iteration; wherein each new child node represents a respective modified molecule that is generated by applying a respective modification operation from a set of possible modification operations to a molecule represented by the node that is selected for expansion at the iteration.

In some implementations, iteratively expanding the toxicity analysis tree over the plurality of iterations comprises: iteratively expanding the toxicity analysis tree over the plurality of iterations to encourage an increase in toxicity predictions of molecules represented by nodes in the toxicity analysis tree.

In some implementations, for each of the plurality of molecule fragments in the input molecule, processing the toxicity analysis tree to generate the toxicity score for the molecule fragment comprises: identifying a plurality of nodes in the toxicity analysis tree that represent molecules which include the molecule fragment; generating a respective node-specific score for each node in the toxicity analysis tree that represents a molecule that includes the molecule fragment; and aggregating the node-specific scores to generate the toxicity score for the molecule fragment.

In some implementations, for each node in the toxicity analysis tree that represents a molecule that includes the molecule fragment, generating the node-specific score comprises: determining the node-specific score based at least in part on: (i) the toxicity prediction for the molecule represented by the node, and (ii) a size of the molecule represented by the node relative to a size of the input molecule.

In some implementations, aggregating the node-specific scores to generate the toxicity score for the molecule fragment comprises: determining the toxicity score for the molecule fragment based on a measure of central tendency of the node-specific scores.

In some implementations, selecting the node in the toxicity analysis tree to expand at the iteration based at least in part on the toxicity predictions for the nodes in the toxicity analysis tree comprises: selecting the node in the toxicity analysis tree to expand at the iteration using a Monte Carlo Tree Search (MCTS) optimization algorithm.

In some implementations, selecting the node in the toxicity analysis tree to expand at the iteration based at least in part on the toxicity predictions for the nodes in the toxicity analysis tree comprises: sequentially traversing nodes in the toxicity analysis tree, starting from the root node, until a node that is eligible for expansion is reached, comprising, at each node before the node that is eligible for expansion is reached: determining a respective selection score for each child node of the node based at least in part on: (i) a toxicity prediction for a molecule represented by the child node, (ii) toxicity predictions for any subtree of the toxicity analysis tree that is rooted at the child node, and (iii) a number of previous visits to the child node; and selecting a child node of the node to be visited next in the sequential traversal of the nodes in the toxicity analysis tree based on the selection scores for the child nodes.

In some implementations, the method further comprises presenting a visual representation of the toxicity scores for the molecule fragments in the input molecule on a display of a user device.

In some implementations, the visual representation of the toxicity scores for the molecule fragments in the input molecule comprises: a two-dimensional (2D) representation of a chemical structure of the input molecule, wherein each of a plurality of molecule fragments in the input molecule are overlaid with a color having an intensity that represents a toxicity score for the molecule fragment.

In some implementations, determining the toxicity prediction for the modified molecule comprises: processing a model input that characterizes the modified molecule using a toxicity prediction machine learning model to generate a model output that defines the toxicity prediction for the modified molecule.

In some implementations, the toxicity prediction machine learning model comprises a decision tree ensemble.

In some implementations, the method further comprises determining a modified molecule having a lower predicted toxicity than the input molecule by modifying the input molecule based at least in part on the toxicity scores for the plurality of molecule fragments in the input molecule.

In some implementations, the method further comprises selecting the modified molecule for physical synthesis.

In some implementations, the method further comprises physically synthesizing the modified molecule selected for physical synthesis.

In some implementations, the method further comprises performing a physical experiment to measure an experimental toxicity of the modified molecule.

According to another aspect, there is provided a system comprising: one or more computers; and one or more storage devices communicatively coupled to the one or more computers, wherein the one or more storage devices store instructions that, when executed by the one or more computers, cause the one or more computers to perform operations of the methods described herein.

According to another aspect, there are provided one or more non-transitory computer storage media storing instructions that when executed by one or more computers cause the one or more computers to perform operations of the methods described herein.

Particular embodiments of the subject matter described in this specification can be implemented so as to realize one or more of the following advantages.

Conventionally, determining the toxicity of a molecule, such as a drug molecule, involves physically synthesizing the molecule and exposing a cell culture to the physically synthesized molecule. In addition, determining the toxicity of the molecule at multiple doses requires further synthesis and testing on cell cultures. Thus, to determine the toxicity of multiple molecules, such as multiple drug candidates in a drug development process, and at multiple doses, can require a large amount of resources and time.

The system described in this specification predicts the toxicity of an input molecule. For example, the system can generate a toxicity dose-response curve for an input molecule given data identifying the input molecule. More specifically, the system can use a toxicity prediction machine learning model to generate a toxicity prediction for the input molecule at each of multiple dose values. The system can generate toxicity dose-response curves for a large number, e.g., greater than 100, 1,000, or 10,000 input molecules, without requiring physical synthesis of the molecules or testing of the molecules on cell cultures. The system can thus accelerate the drug development process by generating a predicted toxicity of a large number of molecules at multiple doses, allowing for early filtering and prioritization of molecules to physically synthesize.

In addition, some conventional systems for determining the toxicity of a molecule involve using biochemical assays, such as cytotoxicity assays or cell viability assays. The system described in this specification can generate toxicity predictions that characterize toxicity in other dimensions, such as cell morphology changes. For example, the system can train the toxicity prediction machine learning model on training examples that each include a target toxicity prediction that characterizes toxicity, of a dimension such as a cell morphology change, for a training molecule at a dose value. The system can generate the target toxicity prediction from one or more images of a cell culture that has been exposed to the training molecule at the dose value. The system can thus train the toxicity prediction machine learning model to generate toxicity predictions that characterize toxicity in dimensions that are not available conventionally, providing for a more thorough understanding of the predicted toxicity of the molecule.

Furthermore, the system described in this specification predicts the toxicity of an input molecule using a smaller amount of computational resources than conventional systems for predicting the toxicity of an input molecule. For example, some conventional systems for predicting the toxicity of an input molecule require performing simulations of how the input molecule interacts with a target molecule, e.g., a protein or enzyme, that is associated with toxic effects. Some of these conventional systems can simulate interactions among atoms in the input molecule and the target molecule using molecular docking or molecular dynamics simulations, which can require a large amount of computational resources and time to perform. For example, a molecular dynamics simulation can involve calculating a large number of interatomic forces between pairs of atoms and across a large number of time steps, which requires a large amount of computational resources. As another example, molecular docking can require a large number of binding energy calculations between pairs of atoms, or simulation of a large number of binding poses, which requires a large amount of computational resources. The system described in this specification can predict toxicity of the input molecule using a single forward pass through a toxicity prediction machine learning model, reducing consumption of computational resources that would otherwise be needed to perform molecular docking or a molecular dynamics simulation. Each forward pass consumes a consistent and small amount of computational resources compared to simulations.

In addition, some conventional systems predict toxicity of an input molecule for a target molecule associated with toxic effects, limiting the toxicity predictions to the toxic effects of available or known target molecules. The system described in this specification can predict toxicity of an input molecule without being limited to the toxic effects associated with the target molecule, providing more thorough and comprehensive information about the toxicity of the input molecule.

Furthermore, predicting the toxicity of the input molecule for different target molecules associated with different toxic effects requires using molecular docking or performing a molecular dynamics simulation for each of the different target molecules, which is computationally expensive. The system described in this specification can predict toxicity of the input molecule using a single forward pass through a toxicity prediction machine learning model for each of multiple dimensions characterizing toxicity, reducing consumption of computational resources that would otherwise be needed to perform molecular docking or a molecular dynamics simulation for each of multiple different target molecules in order to determine different toxic effects.

In some implementations, the toxicity prediction machine learning model can have been trained to generate a toxicity prediction for an input molecule given a variety of features of the input molecule. For example, the toxicity prediction machine learning model can have been trained on training examples that include different combinations of sets of features characterizing a training molecule and a dose value, and a target toxicity. Some of the features can have been derived from images of cell cultures exposed to training molecules. The training examples can have been derived from a large number of diverse training molecules, providing for better generalization at inference compared to training examples derived from a smaller number of training molecules or a smaller variety of features.

In some implementations, the system can train the toxicity prediction machine learning model on training data that has been normalized to account for biases and artificial sources of variability in the multi-well plate-based experiments from which the training data is derived. For example, a training example can include a target toxicity that is based on a toxicity measurement of a cell culture that has been exposed to a training molecule at a dose value specified by the training example. The cell culture is located at a particular spatial location in a multi-well plate. In some cases, the toxicity measurement is systematically biased due to the particular spatial location of the cell culture in the multi-well plate, e.g., due to the differences in environmental conditions at different positions of the plate, or consistent variations in the number of cells placed at different positions of the plate. The system described in this specification can address this issue by normalizing the toxicity measurement of each training example based on a spatial location of the target well that holds the cell culture in the multi-well plate. For example, the system can normalize the toxicity measurement using a normalization machine learning model for the multi-well plate. Thus the system can generate training examples with more accurate target toxicities. The system can train the toxicity prediction machine learning model on training data that is more accurate, resulting in better performance by the toxicity prediction machine learning model at inference.

In some implementations, the system can determine molecule fragments of an input molecule that are likely to contribute to toxicity of the input molecule. For example, the system can process a toxicity analysis tree to generate a respective toxicity score for each of multiple molecule fragments in the input molecule that characterizes an impact of the molecule fragment on a toxicity of the input molecule. In some examples, the system can present a visual representation that shows which molecule fragments are likely to contribute to the toxicity of the input molecule, and which fragments, upon being removed or replaced, can reduce the toxicity of the molecule. The system can thus identify molecule fragments that can be removed or replaced to reduce the toxicity of the input molecule, allowing for insight into the toxicity of the input molecule. The system can thus accelerate the drug development process by identifying molecule fragments that are likely to contribute to toxicity of an input molecule.

Conventional systems for predicting the toxicity of an input molecule provide only a toxicity prediction for the input molecule, allowing for limited understanding of which parts of the input molecule contribute to the toxicity of the input molecule. The system described in this specification addresses this issue by identifying molecule fragments of an input molecule that are likely to contribute to toxicity of the input molecule, allowing for understanding of which parts of the input molecule contribute to the toxicity of the input molecule at a more granular level.

Furthermore, the system can generate the toxicity analysis tree in a computationally efficient manner. Generating the toxicity analysis tree in a conventional manner, e.g., using naive expansion or brute-force expansion, can result in a large toxicity analysis tree, which requires a large amount of computing resources such as time and memory for generation and storage. In some cases, generating the toxicity analysis tree in a conventional manner is computationally infeasible due to the large number of possible modified molecules that can be included in the toxicity analysis tree. The system described in this specification addresses this issue by expanding the toxicity analysis tree based on the toxicity predictions for molecules represented by the nodes in the toxicity analysis tree. For example, the system can expand the toxicity analysis tree to encourage an increase in toxicity predictions of molecules represented by nodes in the toxicity analysis tree by selecting nodes to expand at each iteration based at least in part on the toxicity predictions for the nodes in the toxicity analysis tree. Thus the system described in this specification can generate a toxicity analysis tree by prioritizing an increase in toxicity predictions, resulting in a smaller toxicity analysis tree that requires less computing time and resources to generate and store.

In some implementations, the system can generate data defining multiple modified molecules that can replace an input molecule, e.g., modified molecules that have similar chemical or biological properties as the input molecule. For example, given an input molecule and a target molecule fragment of the input molecule, the system can generate data defining a modified molecule for the input molecule, where the modified molecule includes an alternative molecule fragment in place of the target molecule fragment. In particular, the target molecule fragment can be, e.g., a molecule fragment that is predicted to contribute to toxicity of the input molecule as described above. The alternative molecule fragment can be a bioisostere for the target molecule fragment. For example, the modified molecule that includes the alternative molecule fragment in place of the target molecule fragment can have similar chemical or biological properties, e.g., therapeutic effects, as the input molecule, while potentially having a lower toxicity. The system can thus allow for the identification of potential replacement molecules for the input molecule that, in some cases, can have a lower toxicity than the input molecule. The system can thus accelerate the drug development process.

Some conventional systems for generating data defining modified molecules can involve replacing a target molecule fragment with alternative molecule fragments from predefined or manually created libraries of bioisosteres, e.g., created by researchers. However, predefined or manually created libraries can include a limited number of bioisosteres for each target molecule fragment, or include bioisosteres for a limited number of target molecule fragments. In addition, replacing a target molecule fragment in different input molecules with the same bioisostere can have different effects on the chemical or biological properties of the resulting modified molecule.

The system described in this specification addresses these issues by selecting candidate molecule fragments from a database of candidate molecule fragments based on a similarity measure between each candidate molecule fragment and the target molecule fragment. For example, the system can determine, for each candidate molecule fragment in the database of candidate molecule fragments, a respective similarity measure between an embedding of the target molecule fragment and an embedding of the candidate molecule fragment. For each selected candidate molecule fragment, the system can generate data defining a modified molecule. The system can thus generate data defining modified molecules with candidate molecule fragments that are selected from a varied database of candidate molecule fragments and that are predicted, e.g., based on the similarity measures, to be bioisosteres for the target molecule fragment.

The system can then generate a toxicity prediction for each modified molecule. By generating a toxicity prediction for each modified molecule, the system can allow for the identification and synthesis of molecules that have lower toxicity than the input molecule. The synthesized molecules can be used, e.g., with similar therapeutic effects as the input molecule, with fewer or less serious side effects.

Furthermore, the system can enable reduced consumption of computational resources required to identify modified molecules that have lower toxicity than the input molecule. For example, the bioisosteres included in predefined libraries can have been included in the libraries without taking into account the context of the input molecule that includes the target molecule fragment that the bioisostere replaces. Thus a conventional system that replaces the target molecule fragment with bioisosteres included in predefined libraries requires generating toxicity predictions for a large number of modified molecules with randomly selected bioisosteres. The system described in this specification generates data defining a small set of modified molecules with candidate molecule fragments that are predicted, e.g., based on the similarity measures, to be bioisosteres for the target molecule fragment. Thus the system generates toxicity predictions for a smaller number of modified molecules, consuming a smaller amount of computing time and resources that would be required to generate toxicity predictions for a larger number of modified molecules.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 3A is a flow diagram of an example process for generating a model input to a toxicity prediction machine learning model.

FIGS. 18A-18B show example materials and equipment for performing a physical experiment involving the exposure of cell cultures to an input molecule.
FIGS. 19A-19B show example recipes involved in a physical experiment involving the exposure of cell cultures to an input molecule.
FIG. 22 shows an example reference destination plate layout.
FIG. 24 shows example compound and DMSO volumes picked per concentration.

Like reference numbers and designations in the various drawings indicate like elements.

DETAILED DESCRIPTION

Figure 1A:
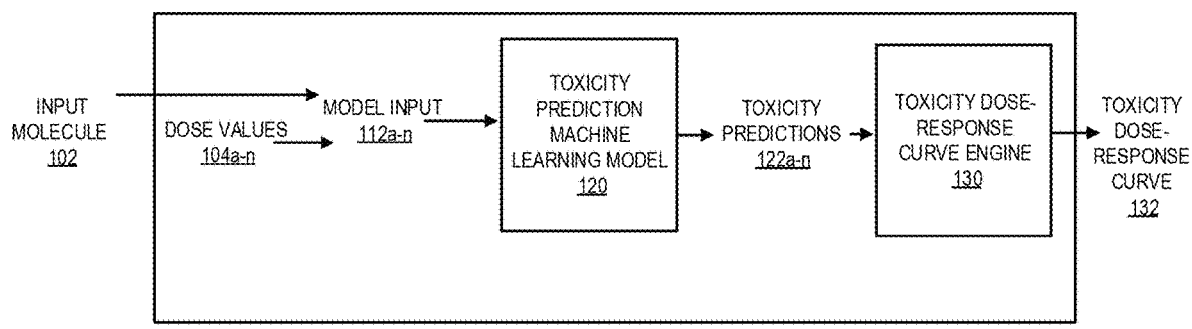
FIG. 1A shows an example toxicity prediction system.

FIG. 1A shows an example toxicity prediction system 100. The toxicity prediction system 100 is an example of a system implemented as computer programs on one or more computers in one or more locations in which the systems, components, and techniques described below are implemented.

The toxicity prediction system 100 is configured to generate a toxicity dose-response curve 132 for an input molecule 102. For example, as described below, the toxicity prediction system 100 can generate the toxicity dose-response curve 132 for the input molecule 102 using a toxicity prediction machine learning model 120.

The toxicity dose-response curve 132 is a curve that defines a respective toxicity prediction for the input molecule 102 for multiple dose values. For example, the toxicity dose-response curve 132 can be a continuous curve that defines a respective toxicity prediction for each dose value in a continuous range of possible dose values. An example toxicity dose-response curve 132 is shown below with reference to FIG. 1B.

In some examples, the toxicity prediction system 100 can generate multiple toxicity dose-response curves for the input molecule 102. For example, each of the toxicity dose-response curves can define toxicity predictions of a different dimension along which toxicity can be measured.

To generate the toxicity-dose response curve 132 for the input molecule 102, the system 100 receives data identifying the input molecule 102. The data identifying the input molecule 102 can include any appropriate data identifying the molecule. For example, the data identifying the input molecule 102 can include a textual representation of the molecule, e.g., a simplified molecular-input line-entry system (SMILES) string identifying the molecule, or an International Chemical Identifier (InChI). In some examples where the input molecule 102 is a protein, the data identifying the input molecule 102 can include data defining an amino acid sequence of the protein. In some examples where the input molecule 102 is a nucleic acid, the data identifying the input molecule 102 can include data defining a nucleic acid sequence of the nucleic acid.

The toxicity prediction system 100 can receive the data identifying the input molecule 102 from any appropriate source, e.g., from a user or from another system, by way of an appropriate interface, e.g., an application programming interface (API) or a user interface (e.g., a graphical user interface). As an example, the other system can be an upstream system that generates data identifying molecules, e.g., in a drug discovery workflow.

For each dose value in a sequence of dose values 104a-n, the toxicity prediction system 100 generates a model input 112a-n. Each model input 112a-n includes a set of features characterizing the input molecule 102 and the corresponding dose value 104a-n.

Each dose value of the dose values 104a-n quantifies an amount of the input molecule 102 administered to a cell culture. For example, the dose value can be a concentration of the input molecule, e.g., in micromolar, millimolar, nanomolar, or picomolar, or a mass per volume of solution.

In some examples, the dose values include dose values in a continuous range of possible dose values. In some examples, the dose values include dose values at a regular interval in a range of possible dose values. In some examples, the dose values in the sequence of dose values 104a-n are predetermined. For example, the dose values in the sequence of dose values 104a-n can include one or more dose values in training data for the toxicity prediction machine learning model 120.

The toxicity prediction system 100 includes a toxicity prediction machine learning model 120. For each dose value in the sequence of dose values 104a-n, the toxicity prediction system 100 processes the model input 112a-n using the toxicity prediction machine learning model 120 to generate a corresponding toxicity prediction 122a-n. Each toxicity prediction 122a-n represents a prediction of a measure of toxicity when exposing cells to the input molecule 102 at the corresponding dose value 104a-n. For example, the toxicity prediction can be based on any one or more dimensions of toxicity, e.g., cell morphology changes (e.g., a proportion of cells or magnitude of visual changes in mitochondrial phenotype such as mitochondrial swelling or fission, cell shape, nuclei size, lipid accumulation, or cytoplasmic vacuolation), membrane integrity (e.g., a biochemical readout indicating membrane integrity, or a proportion of cells or magnitude of visual changes in membrane integrity), metabolic activity (e.g., a biochemical readout indicating metabolic activity, or a proportion of cells or magnitude of visual changes indicating metabolic activity), apoptosis (e.g., a biochemical readout indicating apoptosis, or a proportion of cells or magnitude of visual changes indicating apoptosis), necrosis (e.g., a biochemical readout indicating apoptosis, or a proportion of cells or magnitude of visual changes indicating necrosis), a cell count, or a percent cell viability.

The toxicity prediction machine learning model 120 can be implemented as any appropriate type of machine learning model that can perform a toxicity prediction task, e.g., by processing a model input that includes a set of features characterizing an input molecule and a dose value to generate a toxicity prediction for the input molecule at the dose value. For instance, the toxicity prediction machine learning model 120 can be implemented as a decision tree ensemble, a neural network, or a support vector machine. As particular examples, the toxicity prediction machine learning model 120 can be implemented as a decision tree ensemble, a graph neural network, or a graph Transformer network.

In implementations where the toxicity prediction machine learning model 120 is implemented as a graph neural network, the toxicity prediction machine learning model 120 can process a graph representation of the chemical structure of the input molecule 102. The graph representation represents the input molecule 102 using a set of nodes and a set of edges. Each node in the graph representation can represent a respective atom in the input molecule 102. Each edge in the graph that connects a pair of nodes can represent, e.g., a bond between the two atoms represented by the pair of nodes, or that the two atoms represented by the pair of nodes are separated by less than a threshold distance, e.g., 8 Angstroms. Each node in the graph representation can be associated with a set of features, e.g., elemental type of the atom, of the atom represented by the node. Each edge in the graph can be associated with a set of features, e.g., the type of bond, between the atoms represented by the nodes for which the edge connects. In some examples, the set of features associated with each node can include the dose value of the molecule. In some examples, the set of features associated with each edge can include the dose value of the molecule.

The toxicity prediction machine learning model 120 can include an encoder block, a sequence of one or more message passing layers, and a decoder block. The encoder block can process the set of features associated with each node to generate an embedding associated with the node. In some examples, the encoder block can process the set of features associated with each edge to generate an embedding associated with the edge. The message passing layers can iteratively update the embeddings associated with the nodes using message passing operations that propagate information along the edges. In some examples, the message passing layers can update the embeddings associated with the edges. The decoder block can process the embeddings associated with the nodes to generate the embedding of the molecule. For example, the decoder block can pool (e.g., average pool or max pool) the embeddings associated with the nodes to generate a combined embedding, and project the combined embedding to generate the toxicity prediction. In some examples, the decoder block can process the embeddings associated with the nodes and the embeddings associated with the edges to generate the toxicity prediction. A suitable architecture for a graph neural network is described in Gilmer, J., et al., Neural Message Passing for Quantum Chemistry, arXiv: 1704.01212 (2017).

In implementations where the toxicity prediction machine learning model 120 is implemented as a decision tree ensemble, the toxicity prediction machine learning model can process a feature representation of the model input using multiple decision trees. The feature representation can represent the set of features and the dose value of the model input as a feature vector. Each decision tree processes the feature representation to generate an individual toxicity prediction. For example, each decision tree includes multiple nodes that are each associated with a decision rule and multiple child nodes. The feature representation is processed through the nodes of the decision tree by evaluating the decision rule at each node and selecting one of the child nodes to traverse based on the evaluation of the decision rule, until a leaf node with no child nodes is reached. The leaf node includes the individual toxicity prediction. The toxicity prediction machine learning model 120 combines the individual toxicity predictions (e.g., computes the average) to generate the toxicity prediction. Decision tree ensembles are described in Breiman, L. Random Forests.

Machine Learning 45, 5-32 (2001) and Athey, S., et al., Generalized Random Forests, arXiv: 1610.01271 (2016).

The toxicity prediction system 100 can include a toxicity dose-response curve engine 130. The toxicity dose-response curve engine 130 generates the toxicity dose-response curve 132 based on the toxicity predictions 122a-n. In some examples, the toxicity dose-response curve engine 130 can interpolate between the toxicity predictions 122a-n to generate the toxicity dose-response curve 132.

After generating the toxicity dose-response curve 132, the toxicity prediction system 100 can output the toxicity dose-response curve 132. For example, the toxicity prediction system 100 can present a visual representation of the toxicity dose-response curve on a display of a user device. As another example, the toxicity prediction system 100 can store data defining the toxicity dose-response curve 132 in a memory. As another example, the toxicity prediction system 100 can transmit data defining the toxicity dose-response curve 132 over a data communication network. As another example, the toxicity prediction system 100 can provide data defining the toxicity dose-response curve to a system that performs downstream processing based on the toxicity dose-response curve.

In some implementations, the toxicity prediction system 100 or a downstream system can select the input molecule 102 for physical synthesis based at least in part on the toxicity dose-response curve 132. For example, the toxicity prediction system 100 can select the input molecule 102 out of a set of multiple candidate input molecules if the toxicity dose-response curve indicates a lowest toxicity score out of the toxicity dose-response curves generated by the toxicity prediction system 100 for each of the input molecules in the set.

For example, the toxicity prediction system 100 can obtain a set of multiple candidate input molecules. The toxicity prediction system 100 can generate a toxicity dose-response curve for each of the candidate input molecules. The toxicity prediction system 100 can generate a toxicity score for each of the candidate input molecules based on the toxicity-dose response curve for the candidate input molecule. For example, the toxicity prediction system 100 can generate the toxicity score based on the area under the toxicity dose-response curve, or the maximum dose value that has at most a threshold level of toxicity.

The toxicity prediction system 100 can rank the candidate input molecules based on the toxicity scores. For example, the toxicity prediction system 100 can rank the candidate input molecules in order of ascending toxicity scores, e.g., in examples where a higher toxicity prediction represents a higher toxicity.

The toxicity prediction system 100 can select one or more candidate input molecules for further processing, e.g., for inclusion in a drug, for physical synthesis, or further computational analysis, from the set of candidate input molecules based on the ranking. For example, in examples where a higher toxicity prediction represents a higher toxicity, the system can select the one or more candidate input molecules that have the lowest toxicity scores in the ranking.

Further processing such as further computational analysis can be computationally intensive, and performing further computational analysis of all of the candidate input molecules in the set may be computationally infeasible. By selecting one or more candidate input molecules based on the toxicity scores, the toxicity prediction system 100 performs further processing only on the selected candidate input molecules that are predicted to perform better, e.g., have fewer toxic effects, out of the set of candidate input molecules. The toxicity prediction system 100 can thus filter a set of multiple candidate input molecules to prioritize the selected candidate input molecules for further processing, reducing the consumption of computational resources otherwise required to perform further processing for a larger number or all of the candidate input molecules in the set.

In some implementations, in response to selecting the input molecule for physical synthesis, the toxicity prediction system 100 or another downstream system can physically synthesize the input molecule 102 for physical synthesis based at least in part on the toxicity dose-response curve. In some examples, the system can perform a physical experiment with the physically synthesized molecule, e.g., a physical experiment to measure an experimental toxicity of the input molecule 102.

In some implementations, the toxicity prediction system 100 can generate a prediction of a clinical cell injury, e.g., a clinical liver injury. For example, the system 100 can use a clinical injury prediction machine learning model that is configured to generate a model output that indicates the likelihood of clinical tissue injury given a model input that includes a dose value and one or more features of an input molecule, a cell culture that has been exposed to the input molecule, or both. In some examples, the model input can include an image of a cell culture that has been exposed to the input molecule at the dose value.

The one or more features of cells can include, for example, toxicity predictions generated by the toxicity prediction machine learning model 120 (e.g., cell count, morphological features, predicted metabolic viability) for the input molecule and the dose value. In some examples, the one or more features of cells can include image features, e.g., image embeddings, of a cell culture that has been exposed to the input molecule at the dose value.

As another example, the one or more features of the input molecule can include a set of features characterizing the input molecule, e.g., any one or more of a molecular representation of the input molecule, or molecular properties of the input molecule, as described below with reference to FIG. 2.

The clinical injury prediction machine learning model can be trained on a set of training examples by a machine learning technique. Each of the training examples can include (i) a training input that includes the one or more features of cells, an input molecule, or both, and (ii) a target likelihood of clinical tissue injury.

For each training example, the system can train the clinical injury prediction machine learning model to reduce a discrepancy between: (i) a likelihood of clinical tissue injury generated by the clinical injury prediction machine learning model, and (ii) the target likelihood of clinical tissue injury of the training example. For example, the system can evaluate an objective function that measures an error (e.g., an absolute error) for each training example between (i) a likelihood of clinical tissue injury generated by the clinical injury prediction machine learning model, and (ii) the target likelihood of clinical tissue injury of the training example. The system can determine gradients of the objective function with respect to current values of parameters of the clinical injury prediction machine learning model, e.g., using backpropagation. The system can then update the current values of the parameters of the clinical injury prediction machine learning model using the gradients, e.g., by the update rule of an appropriate gradient descent optimization algorithm, e.g., RMSprop or Adam.

In some examples, the system can derive the target likelihood of clinical tissue injury from clinical data, e.g., a clinical study involving the input molecule and the dose value. In some examples, the system can derive the target likelihood of clinical tissue injury from a clinical injury prediction machine learning model. For example, the system can train a clinical injury prediction machine learning model to generate a likelihood of clinical tissue injury given an image of a cell culture exposed to an input molecule at a dose value, where the target likelihood of clinical tissue injury of the training examples is derived from clinical data. The system can use the trained clinical injury prediction machine learning model to generate predicted likelihoods of clinical tissue injury for each of multiple training molecules for which images of cell cultures exposed to the training molecule exist, but clinical data may not. The system can use the predicted likelihoods of clinical tissue injury as the target likelihoods for training examples for training a clinical injury prediction machine learning model to generate a likelihood of clinical tissue injury given data identifying the structure of an input molecule. The system can thus generate synthetic training data using a clinical injury prediction machine learning model, increasing the amount of training data available, and resulting in a clinical injury prediction machine learning model with better generalization capabilities.

Figure 1B:
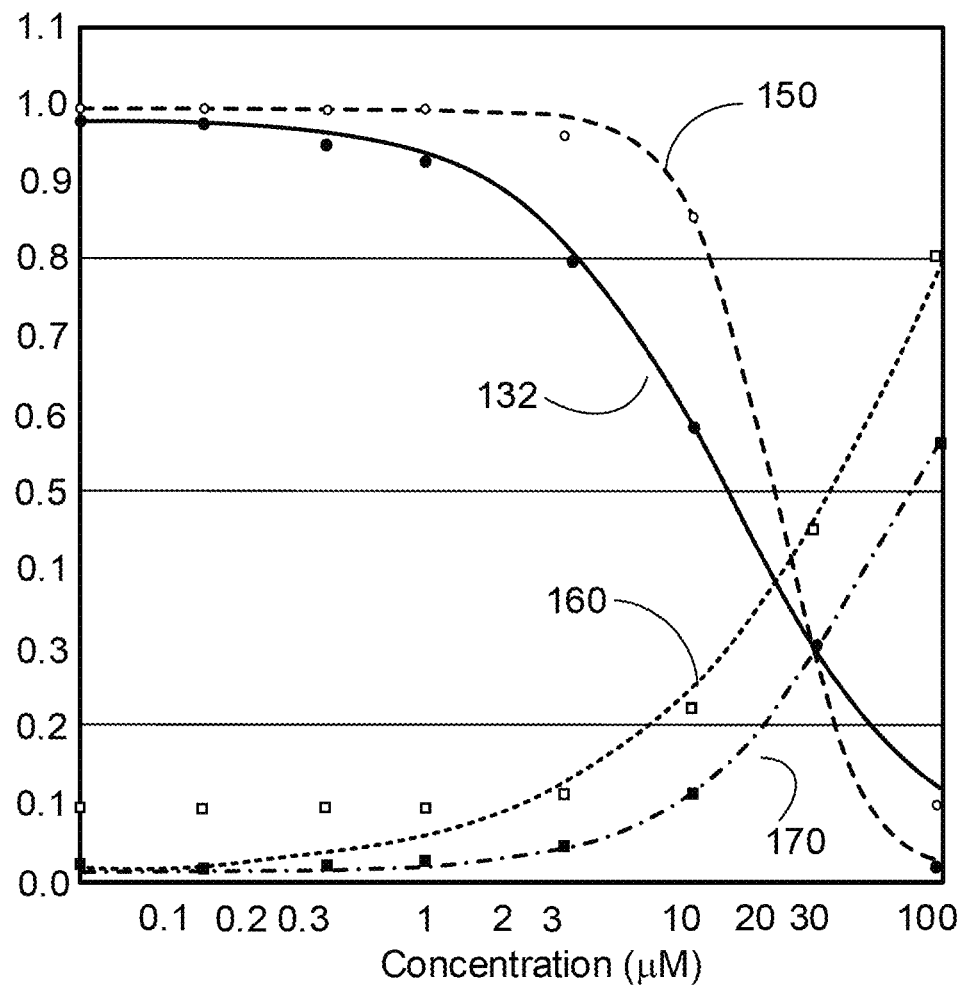
FIG. 1B shows an example toxicity dose-response curve.

FIG. 1B shows an example toxicity dose-response curve 132. The example toxicity dose-response curve 132 defines a toxicity prediction that characterizes metabolic viability for each of multiple dose values. For example, the multiple dose values, measured by concentration, include approximately 0.0, 0.15, 0.32, 1, 4, 10, 30, and 100 micromolar. For each dose value, the system 100 generates a toxicity prediction. For example, for the dose value of 0.15, the system 100 generated a toxicity prediction characterized by a percent cell viability of 0.97.

FIG. 1B also shows other example toxicity dose-response curves 150, 160, and 170 that characterize different dimensions of toxicity than the toxicity dose-response curve 132. For example, the toxicity dose-response curve 150 can characterize a measure of ATP. As another example, the toxicity dose-response curve 160 can characterize a measure of LDH.

Figure 2:
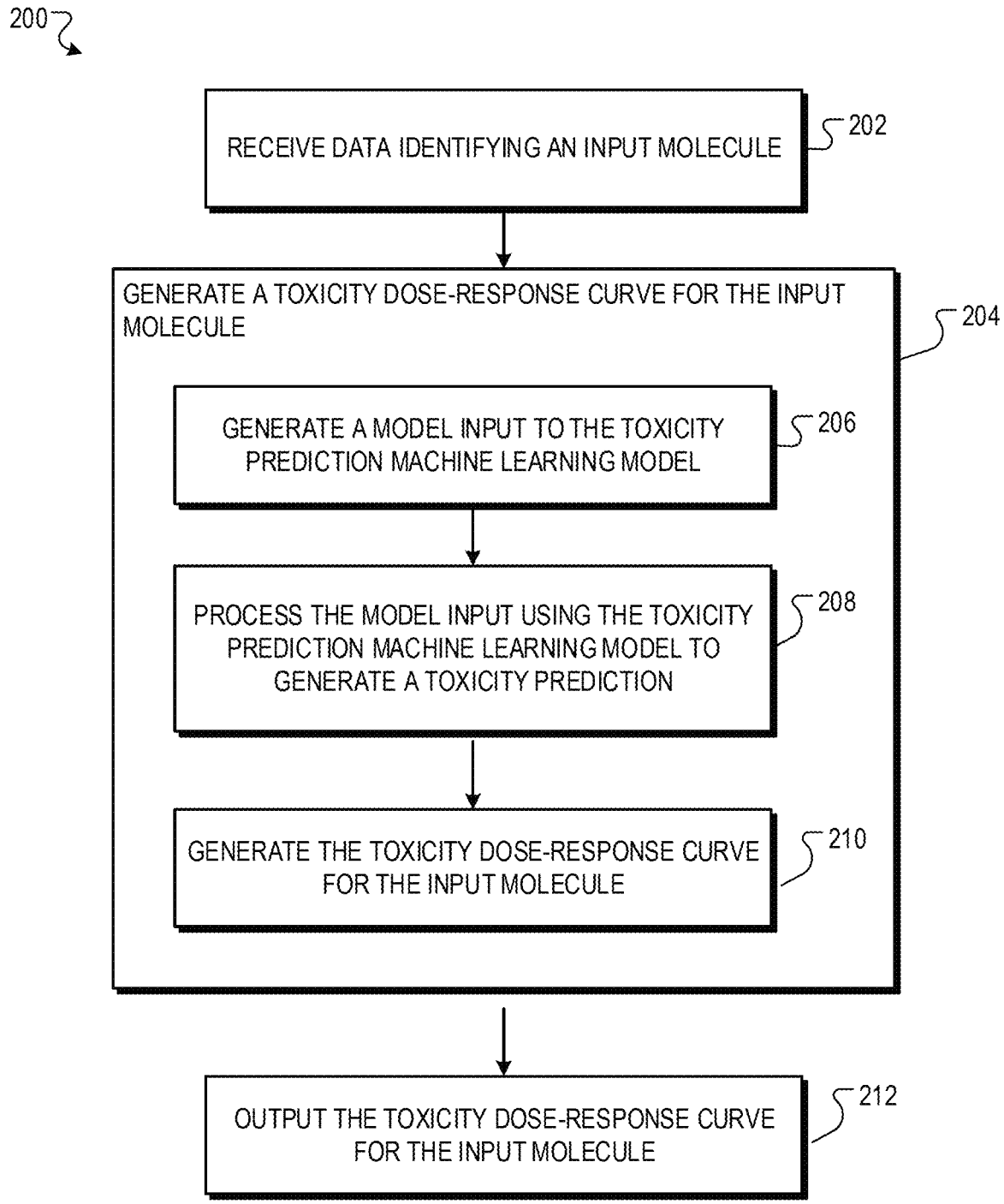
FIG. 2 is a flow diagram of an example process for generating a toxicity dose-response curve for an input molecule.

FIG. 2 is a flow diagram of an example process 200 for generating a toxicity dose-response curve. For convenience, the process 200 will be described as being performed by a system of one or more computers located in one or more locations. For example, a toxicity prediction system, e.g., the toxicity prediction system 100 of FIG. 1A, appropriately programmed in accordance with this specification, can perform the process 200.

The system obtains data identifying an input molecule (step 202). In some examples, the system can obtain the data identifying the input molecule from any appropriate source, e.g., from a user or from an upstream system that generates data identifying an input molecule, e.g., in a drug discovery workflow. The system can obtain the data identifying the input molecule by way of an appropriate interface, e.g., an application programming interface (API) or a user interface (e.g., a graphical user interface).

The system generates a toxicity dose-response curve for the input molecule using a toxicity prediction machine learning model (step 204). The system performs steps 206-208 for each dose value in a sequence of dose values.

For each dose in a sequence of dose values, the system generates a model input to the toxicity prediction machine learning model (step 206). The model input includes a set of features characterizing the input molecule, and the dose value. In some examples, as described below with reference to FIG. 3A, the system generates the model input to also include an embedding of the input molecule.

The set of features characterizing the input molecule can include any one or more of a molecular representation of the input molecule, or molecular properties of the input molecule. The molecular representation can include, for example, a molecular fingerprint of the input molecule. The molecular fingerprint of the input molecule can define substructures around each atom in the input molecule, e.g., using Extended Connectivity Fingerprints (ECFP), a set of binary fingerprints based on molecular substructures of the input molecule, e.g., using MACCS Keys; molecular paths or linear fragments, e.g., using path-based fingerprints such as in Daylight or RDKit's default fingerprinting, or features such as hydrogen bond donors and acceptors, charges, and hydrophobic groups of the input molecule.

In some examples, the molecular representation can include 3D structural information of the input molecule.

In some examples, the molecular representation can include a vector of features representing the input molecule. In some examples, the vector of features can have been generated using a neural network such as a graph neural network. For example, the system can process a graph representation of the input molecule using the graph neural network to generate the vector of features. The graph neural network can have been pre-trained to extract a vector of features for a given graph representation of a molecule.

In some examples, the molecular representation can include an embedding of the input molecule. For example, the embedding of the input molecule can have been generated by a molecule embedding neural network. Generating the embedding of the input molecule is described in further detail below with reference to FIG. 3A.

The molecular properties of the input molecule can include physicochemical descriptors, e.g., a predicted solubility, molecular weight, log P (octanol-water partition coefficient), hydrogen bond donors and acceptors, polar surface area, etc. The molecular properties of the input molecule can also include topological descriptors such as Wiener index, Balaban index, and other graph-theoretical metrics that reflect molecular connectivity. The molecular properties of the input molecule can also include electronic descriptors such as partial charges, electronegativity, and dipole moments.

For each dose in the sequence of dose values, the system processes the model input using the toxicity prediction machine learning model to generate a toxicity prediction for the input molecule at the dose value (step 208). For example, the system can process the model input using the toxicity prediction machine learning model and in accordance with values of a set of machine learning model parameters to generate the toxicity prediction.

The toxicity prediction can represent a prediction of a measure of toxicity when exposing cells to the input molecule at the dose value. For example, the toxicity prediction can be based on any one or more dimensions of toxicity, e.g., cell morphology changes (e.g., mitochondrial phenotype such as mitochondrial swelling or fission, cell shape, nuclei size, lipid accumulation, or cytoplasmic vacuolation), membrane integrity, metabolic activity, apoptosis, necrosis, a cell count, or a percent cell viability.

In some implementations, the system can train the toxicity prediction machine learning model by generating a set of training examples. Each training example can include (i) a training input that includes a set of features characterizing a training molecule and a dose value, and (ii) a target toxicity.

In some examples, at least some of the training examples in the set can include a training input with a different set of features. For example, the training examples in the set can have different combinations of features in the set of features.

In some examples, the system can obtain data defining the training molecules from existing libraries of molecules. For example, the system can randomly select the training molecules from databases such as PubChem or ChEMBL.

In some examples, for each of one or more of the training examples, the system can generate the target toxicity as described in further detail below with reference to FIG. 4 or FIG. 5.

In some examples, for each of one or more of the training examples, the target toxicity of the training example can be determined based on a toxicity measurement of a cell culture that has been exposed to the training molecule of the training example at the dose value specified by the training example. In these examples, the cell culture corresponding to the training example is located in a target well in a multi-well plate. The toxicity measurement of the cell culture can be normalized based on a spatial location in the multi-well plate of the target well that holds the cell culture. Normalizing the toxicity measurement of the cell culture is described in further detail below with reference to FIG. 6.

In some examples, for each of one or more of the training examples, the target toxicity of the training example for a particular dose value can be determined by interpolating between the target toxicity of training examples for other dose values. For example, the system can determine target toxicities for a training molecule for multiple dose values. The system can determine interpolated target toxicities for one or more dose values that are in between the dose values of the training examples for the training molecule. The system can generate training examples for a training molecule for additional dose values without having to expose cell cultures to the additional dose values of the training molecule. The system can thus augment the existing training examples for each training molecule to generate a large number of training examples for the training molecule. Having a larger number of training examples can allow for training larger, e.g., having more parameters, machine learning models, that can perform better at inference than smaller machine learning models. Training a toxicity prediction machine learning model on a larger number of training examples can result in better performance at inference, e.g., by reducing the risk of overfitting and improving robustness.

The set of features characterizing the training molecule can include any one or more of a molecular representation of the training molecule, molecular properties of the training molecule, or an embedding of the training molecule. The molecular representation can include, for example, a vector of features representing the training molecule. In some examples, the vector of features can have been generated using a graph neural network as described above. In some examples, the molecular representation can include a molecular fingerprint or 3D structural information of the training molecule. The molecular properties can include physicochemical properties or a metabolite profile of the training molecule. The embedding of the training molecule can have been generated by a molecule embedding neural network as described below with reference to FIG. 3A.

In some examples, each training input can also include one or more toxicity predictions of different dimensions than the target toxicity of the training example. For example, if the target toxicity is based on a percent cell viability, the training input can include one or more of the cell count after exposure, the nuclei size after exposure, or morphological features of organelles such as the mitochondrial phenotype after exposure. By including toxicity predictions of other dimensions in the training input, the system can generate training examples that provide a richer training signal, which can result in improved performance and robustness of the toxicity prediction machine learning model after training.

The system can train the toxicity prediction machine learning model on the set of training examples by a machine learning training technique. For example, for each training example, the system can train the toxicity prediction machine learning model to reduce a discrepancy between: (i) a toxicity prediction generated by the toxicity prediction machine learning model by processing the training input of the training example, and (ii) the target toxicity of the training example.

For example, the system can evaluate an objective function that measures an error (e.g., a mean absolute error, or a mean squared error) between (i) toxicity predictions generated by the toxicity prediction machine learning model by processing the training inputs of a batch of training examples, and (ii) the target toxicities of the batch of training examples.

In some examples where the toxicity prediction machine learning model includes a tree-based model such as a decision tree ensemble, the system can generate one or more trees, each corresponding to a batch of training examples. At each of multiple nodes in the tree, the system can determine a decision rule that splits the training examples based on minimizing the objective function for the resulting child nodes created by the split.

In some examples where the toxicity prediction machine learning model includes a neural network, the system can determine gradients of the objective function with respect to current values of parameters of the toxicity prediction machine learning model, e.g., using backpropagation. The system can then update the current values of the parameters of the toxicity prediction machine learning model using the gradients, e.g., by the update rule of an appropriate gradient descent optimization algorithm, e.g., RMSprop or Adam.

The system generates the toxicity dose-response curve for the input molecule based on the toxicity predictions for the sequence of dose values (step 210).

In some examples, the system can generate the toxicity dose-response curve by interpolating between the toxicity predictions generated by the toxicity prediction machine learning model. For example, the system can generate a dose-response curve that best fits the toxicity predictions, and is continuous. In some examples, the system can determine interpolated toxicity predictions for one or more dose values that are in between the dose values in the sequence. The system can determine interpolated toxicity predictions such that the toxicity dose-response curve is smooth.

For example, the system can generate the toxicity dose-response curve by fitting a smooth function, e.g., using polynomial regression or spline interpolation, to the toxicity predictions generated by the toxicity prediction machine learning model.

In some examples, the system can modify the toxicity dose-response curve according to one or more rules. For example, the system can modify the toxicity dose-response curve to start, e.g., determine the toxicity prediction for a dose value of 0, at a predetermined value.

The system outputs the toxicity dose-response curve for the input molecule (step 212). As an example, the system can present a visual representation of the toxicity dose-response curve on a display of a user device. For example, the visual representation can include a graph that plots the toxicity predictions against the dose values.

FIG. 3A is a flow diagram of an example process 300 for generating a model input to a toxicity prediction machine learning model. For convenience, the process 300 will be described as being performed by a system of one or more computers located in one or more locations. For example, a toxicity prediction system, e.g., the toxicity prediction system 100 of FIG. 1A, appropriately programmed in accordance with this specification, can perform the process 300.

The system processes at least a representation of a chemical structure of the input molecule using a molecule embedding neural network to generate an embedding of the input molecule (step 302). An embedding of an entity, e.g., a molecule or an image, can refer to a representation of the entity as an ordered collection of numerical values, e.g., a vector, matrix, or other tensor of numerical values.

In some examples, the representation can include a textual representation, e.g., a SMILES string, of the chemical structure of the input molecule. In some examples, the representation of the chemical structure can define a spatial arrangement, e.g., a respective spatial location, of each of one or more atoms in the input molecule. For example, the representation can include a 2D representation or a 3D representation of the input molecule. In some of these examples, the system can generate the representation of the chemical structure of the input molecule from the data identifying the input molecule. For example, the system can process a SMILES string identifying the input molecule to generate a 2D or 3D representation of the input molecule.

In some examples, the system processes the representation of the chemical structure of the input molecule and a dose value of the input molecule using the molecule embedding neural network to generate the embedding of the input molecule.

The molecule embedding neural network is configured to process at least a representation of a chemical structure of a molecule to generate an embedding of the molecule. In some examples, the system processes the representation of the chemical structure of the molecule and a dose value of the molecule to generate the embedding of the molecule.

The molecule embedding neural network can have any appropriate neural network architecture that enables the molecule embedding neural network to perform its described functions. In particular, the molecule embedding neural network can include any appropriate types of neural network layers (e.g., fully connected layers, message passing layers, convolutional layers, attention layers, recurrent layers, pooling layers, and so forth), in any appropriate number (e.g., 5 layers, or 10 layers, or 50 layers), and connected in any appropriate configuration (e.g., as a directed graph of layers).

As a particular example, the molecule embedding neural network can be implemented as a graph neural network. For example, the molecule embedding neural network can process a graph representation of the chemical structure of the molecule. The graph representation represents the molecule using a set of nodes and a set of edges. Each node in the graph representation can represent a respective atom in the molecule. Each edge in the graph that connects a pair of nodes can represent, e.g., a bond between the two atoms represented by the pair of nodes, or that the two atoms represented by the pair of nodes are separated by less than a threshold distance, e.g., 8 Angstroms. Each node in the graph representation can be associated with a set of features, e.g., elemental type of the atom, of the atom represented by the node. Each edge in the graph can be associated with a set of features, e.g., the type of bond, between the atoms represented by the nodes for which the edge connects. In some examples, the set of features associated with each node can include the dose value of the molecule. In some examples, the set of features associated with each edge can include the dose value of the molecule.

The molecule embedding neural network can include an encoder block, a sequence of one or more message passing layers, and a decoder block. The encoder block can process the set of features associated with each node to generate an embedding associated with the node. In some examples, the encoder block can process the set of features associated with each edge to generate an embedding associated with the edge. The message passing layers can iteratively update the embeddings associated with the nodes using message passing operations that propagate information along the edges. In some examples, the message passing layers can update the embeddings associated with the edges. The decoder block can process the embeddings associated with the nodes to generate the embedding of the molecule. For example, the decoder block can pool (e.g., average pool or max pool) the embeddings associated with the nodes to generate the embedding of the molecule. In some examples, the decoder block can process the embeddings associated with the nodes and the embeddings associated with the edges to generate the embedding of the molecule. A suitable architecture for a graph neural network is described in Gilmer, J., et al., Neural Message Passing for Quantum Chemistry, arXiv: 1704.01212 (2017).

In some implementations, the molecule embedding neural network can have been jointly trained, e.g., by the system, with an image embedding neural network. The image embedding neural network can be configured to process a set of one or more images to generate an embedding of the set of images.

The image embedding neural network can have any appropriate neural network architecture that enables the molecule embedding neural network to perform its described functions. In particular, the image embedding neural network can include any appropriate types of neural network layers (e.g., fully connected layers, message passing layers, convolutional layers, attention layers, recurrent layers, pooling layers, and so forth), in any appropriate number (e.g., 5 layers, or 10 layers, or 50 layers), and connected in any appropriate configuration (e.g., as a directed graph of layers).

As a particular example, the image embedding neural network can be implemented as a convolutional neural network. For example, the convolutional neural network can include a sequence of convolutional layers (e.g., 3, 5, or 10 convolutional layers) generate feature maps for the set of images. The convolutional neural network can include a pooling layer that performs a pooling operation (e.g., a max pooling) over the feature maps to generate the embedding of the set of images.

In some examples, to jointly train the molecule embedding neural network and the image embedding neural network, the system can obtain a set of molecule-image pairs, where each molecule-image pair includes (i) chemical structure data for a molecule, and (ii) a set of one or more images of a cell culture that has been exposed to the molecule. Each set of images of a cell culture can depict a cell culture that has been exposed to the molecule at a particular dose value of the molecule. In some examples, each molecule-image pair can also include data representing the dose value of the molecule.

In some examples, one or more of the images in the set can include fluorescence microscopy images that include multiple fluorescence channels that correspond to different cellular structures. Each of the fluorescence microscopy images can have been captured after the cell culture is stained with a panel of fluorescent dyes that mark various cellular structures. For example, each image in the set can correspond to a fluorescence channel and can have been captured after the cell culture is stained with the fluorescent dye corresponding to the fluorescence channel.

Figure 3B:
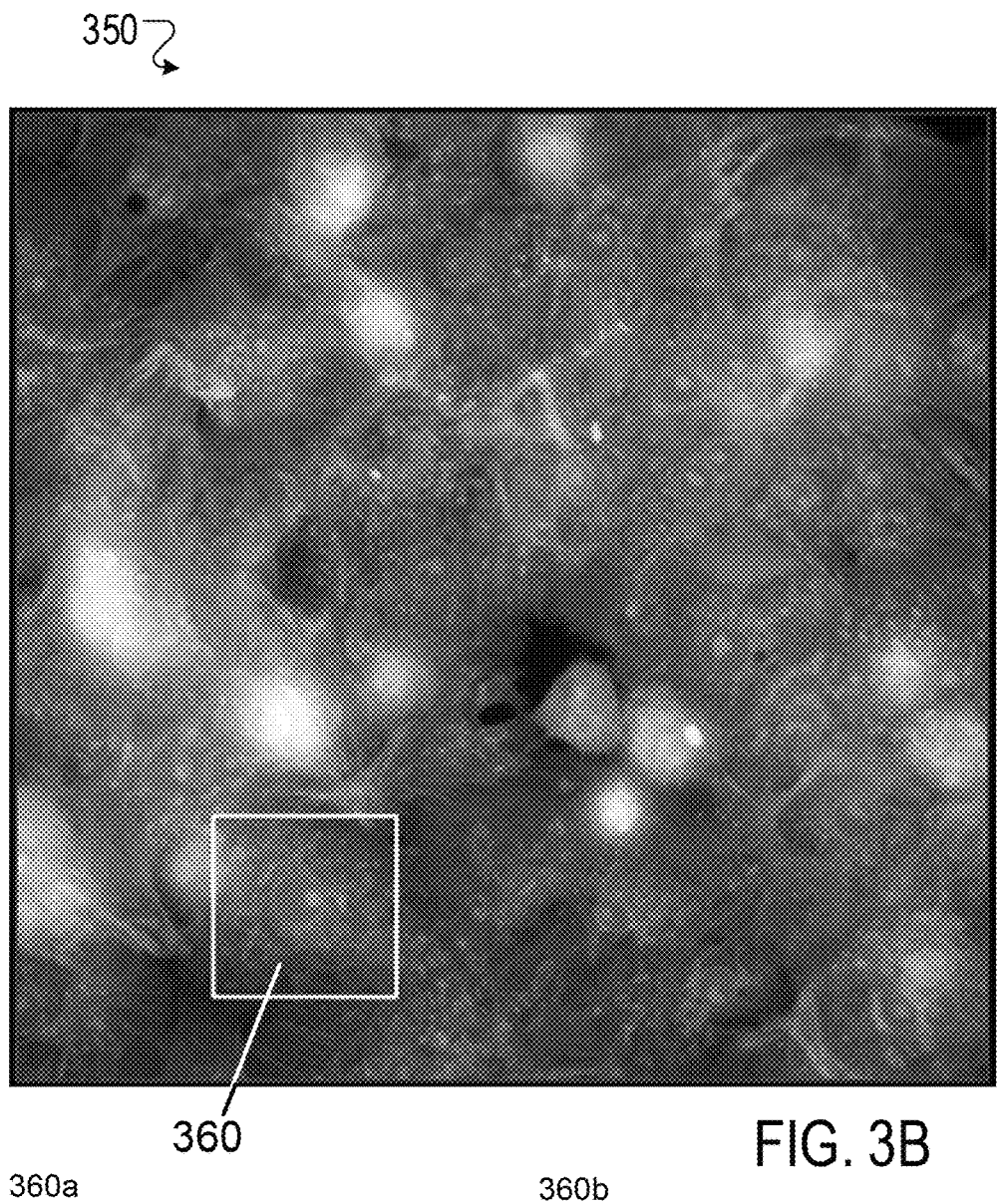
FIG. 3B shows an example fluorescence microscopy image.

As an example, each of the fluorescence microscopy images can have been captured after performing cell painting using the panel of fluorescent dyes on the cell culture. An example fluorescence microscopy image is shown in FIG. 3B.

To capture a fluorescence microscopy image for a molecule at a dose value, the cell culture can be exposed to the molecule at the dose value. Each dye in the panel of fluorescent dyes can be applied simultaneously or sequentially to the cell culture. Each dye targets a specific cellular structure, e.g., DNA, endoplasmic reticulum (ER), plasma membrane, RNA, Golgi apparatus, mitochondria, lysosomes, etc.

Figure 3C:
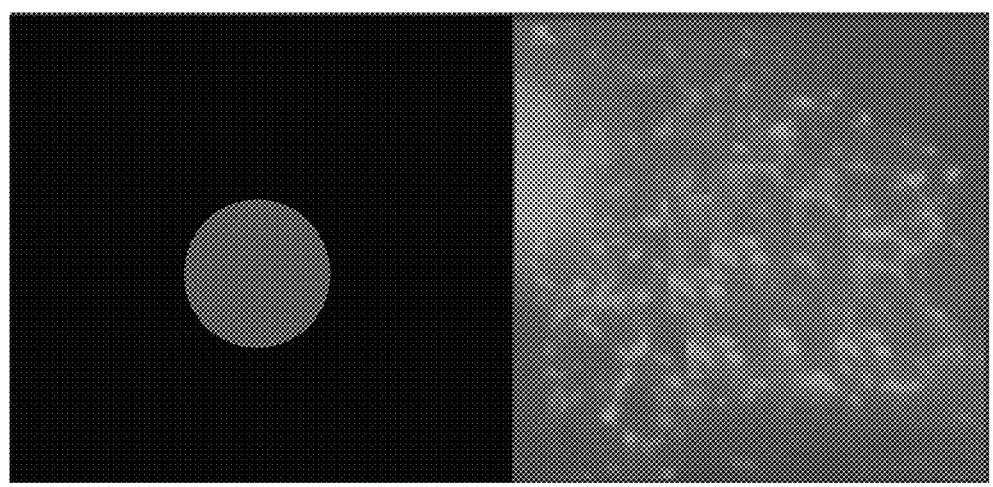
FIG. 3C shows example fluorescence channels for a region of an example fluorescence microscopy image.

For each dye, a fluorescence channel is captured, e.g., by an imaging sensor, that corresponds to the cellular structure targeted by the dye. Example fluorescence channels are shown in FIG. 3C. The fluorescence channels can be combined to generate a multi-channel fluorescence microscopy image. Example techniques for cell painting are described in Bray, M. A., et al., Cell Painting, a high-content image-based assay for morphological profiling using multiplexed fluorescent dyes. Nature protocols, 11 (9), 1757-1774 (2016).

The system can jointly train the molecule embedding neural network and the image embedding neural network on the set of molecule-image pairs to optimize a contrastive objective function. For example, the system can learn a joint molecule-image embedding space. An example contrastive objective function is described in Radford, A. et al., Learning Transferable Visual Models from Natural Language Supervision, arXiv: 2103.00020 (2021).

In some implementations, for each molecule and each set of one or more images that are included in a same molecule-image pair, the contrastive objective function encourages an increase in similarity between: (i) an embedding of the molecule that is generated by the molecule embedding neural network, and (ii) an embedding of the set of images that is generated by the image embedding neural network. For example, the contrastive objective function encourages a molecule and the set of images included in the same molecule-image pair as the molecule to have embeddings that have a high similarity measure, e.g., cosine similarity, Euclidean distance, etc., to each other in the joint molecule-image embedding space.

In some implementations, for each molecule and each set of one or more images that are not included in a same molecule-image pair, the contrastive objective function encourages a decrease in similarity between: (i) an embedding of the molecule that is generated by the molecule embedding neural network, and (ii) an embedding of the set of images that is generated by the image embedding neural network. For example, the contrastive objective function encourages a molecule and the sets of images that are not included in the same molecule-image pair as the molecule to have embeddings that have a low similarity measure to each other in the joint molecule-image embedding space.

In some implementations, the contrastive objective function further encourages: (i) an increase in similarity between respective embeddings of differently transformed versions of images that are included in a same molecule-image pair; and (ii) a decrease in similarity between respective embeddings of images that are included in different molecule-image pairs. For example, the differently transformed versions of the images can include sheared, rotated, or inverted versions of the images included in the molecule-image pair.

As an example, to train the molecule embedding neural network and the image embedding neural network, the system can determine gradients of the contrastive objective function with respect to current values of parameters of the molecule embedding neural network and the image embedding neural network, e.g., using backpropagation. The system can then update the current values of the parameters of the molecule embedding neural network and the image embedding neural network using the gradients, e.g., by the update rule of an appropriate gradient descent optimization algorithm, e.g., RMSprop or Adam.

By training the molecule embedding neural network and the image embedding neural network to optimize a contrastive objective function, the system can train the molecule embedding neural network to generate an embedding of a molecule that implicitly incorporates features of images of cell cultures that have been exposed to the molecule, thus resulting in an embedding that captures different types of information than the representation of the chemical structure of the molecule.

The system includes the embedding of the input molecule in the model input to the toxicity prediction machine learning model (step 304). The system can process the model input that includes the embedding of the input molecule using the toxicity prediction machine learning model as described with reference to step 208 of FIG. 2. Thus the system can provide additional features as input to the toxicity prediction machine learning model, improving the performance of the toxicity prediction machine learning model.

In some implementations, the system can use the embedding of the input molecule to obtain one or more images of a cell culture for the input molecule. The system can provide the one or more images of a cell culture for the input molecule for presentation on the user device. By providing one or more images of a cell culture, the system can allow for a deeper and richer source of context for understanding toxicity in addition to the toxicity dose-response curve. For example, the one or more images can be analyzed by expert users such as toxicologists and physicians.

In addition, in some examples, the system can provide the one or more images as input to downstream image analysis models, providing for further insight into toxicity of the input molecule. For example, the system can process the one or more images using, e.g., a segmentation machine learning model configured to identify features of a cell culture, to generate data representing features such as morphological features of organelles depicted in the one or more images. The system can provide data representing the features for presentation on the user device.

In some examples, the system can obtain the one or more images of the cell culture based on a similarity in a joint molecule-image embedding space between an embedding of the input molecule and an embedding of a set of one or more images of a cell culture that has been exposed to a molecule. For example, the system can generate an embedding of the input molecule in the embedding space using the molecule embedding neural network. The system can identify a set of images that has an embedding of the highest similarity to the embedding of the input molecule in the embedding space.

The system can provide the one or more identified for presentation on the user device.

As another example, the system can generate a synthetic image of a cell culture for the input molecule at a dose value in the sequence of dose values. For example, the system can process the embedding of the input molecule using a generative neural network, e.g., a generative diffusion model or generative adversarial network, to generate an image of a cell culture for the input molecule at the dose value. The generative neural network is configured to process a network input that includes a molecule embedding to generate a sample from an image space of the generative neural network.

The generative neural network can have been trained on a set of training examples by a machine learning technique. For example, each training example can include a training network input that includes an embedding of a molecule, and a training target output that includes an image of the molecule. For example, the generative neural network can have been trained to minimize the difference, e.g., a reconstruction loss, between an image generated by the generative neural network by processing a training network input of a training example, and a target image of the training example. In some examples, the system can obtain the training network input and the training target output from a molecule-image pair for the molecule. Example suitable architectures for generative neural networks for generating images are described in Rombach, R. et al., High-Resolution Image Synthesis with Latent Diffusion Models, arXiv: 2112.10752 (2022) and Goodfellow, I., et al. Generative adversarial networks, arXiv: 1406.2661 (2014).

FIG. 3B shows an example fluorescence microscopy image 350. The image 350 shows different cellular structures in different colors. For example, DNA is depicted in dark gray and mitochondria are depicted in gray. The golgi apparati, RNA, and actin filaments are depicted in light gray. The example fluorescence microscopy image 350 can have been generated from multiple fluorescence channels as described above with reference to FIG. 3A.

FIG. 3C shows example fluorescence channels 360a and 360b for a region 360 of the image 350 of FIG. 3B. For example, the fluorescence channel 360a can correspond to DNA, and depicts only the DNA in the region 360. The fluorescence channel 360b can correspond to mitochondria, and depicts only the mitochondria in the region 360.

Figure 4:
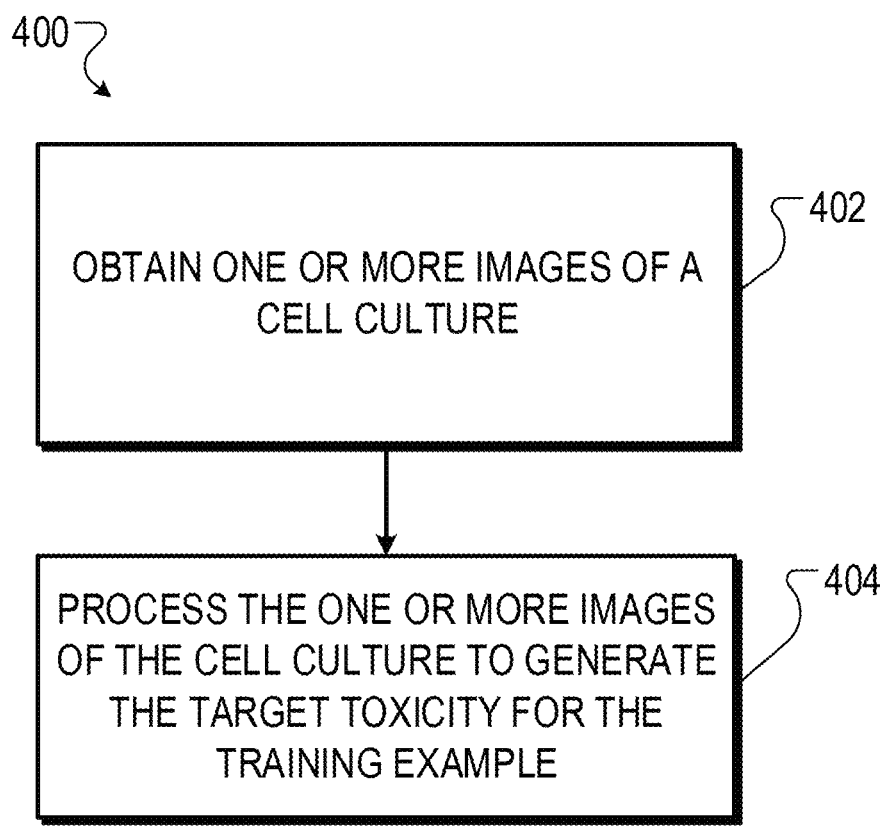
FIG. 4 is a flow diagram of an example process generating a target toxicity for a training example for training a toxicity prediction machine learning model.

FIG. 4 is a flow diagram of an example process 400 generating a target toxicity for a training example for training a toxicity prediction machine learning model. For convenience, the process 400 will be described as being performed by a system of one or more computers located in one or more locations. For example, a toxicity prediction system, e.g., the toxicity prediction system 100 of FIG. 1A, appropriately programmed in accordance with this specification, can perform the process 400.

The system obtains one or more images of a cell culture (step 402). The cell culture can have been exposed to the training molecule of the training example at the dose value specified by the training example.

As an example, the one or more images of the cell culture can include fluorescence microscopy images that include multiple fluorescence channels that correspond to different cellular structures. The fluorescence microscopy image can have been captured after the cell culture has been stained with a panel of fluorescent dyes that mark various cellular structures. As an example, each of the fluorescence microscopy images can have been captured after performing cell painting using the panel of fluorescent dyes on the cell culture. Cell painting is described in more detail above with reference to FIG. 3A. An example fluorescence microscopy image, generated from multiple fluorescence channels, is shown in FIG. 3B. Example fluorescence channels are shown in FIG. 3C.

The system processes the one or more images of the cell culture to generate the target toxicity for the training example (step 404).

For example, the system can determine the target toxicity for the training example based on one or more of: a number of cells in the cell culture after being exposed to the training molecule, morphological features of organelles in cells in the cell culture after being exposed to the training molecule, a size of cells in the cell culture after being exposed to the training molecule, a proportion of cells or magnitude of visual changes in membrane integrity, a proportion of cells or magnitude of visual changes in metabolic activity, a proportion of cells or magnitude of visual changes indicating apoptosis, or a proportion of cells or magnitude of visual changes indicating necrosis. Morphological features of organelles can include, for example, nuclei size, mitochondrial phenotype, e.g., swelling or fission, cell shape, cytoplasmic vacuolation, or lipid accumulation.

In some examples, the system can process the one or more images of the cell culture using an image processing neural network to generate a segmentation of the one or more images of the cell culture. The segmentation can identify, e.g., different cells, or different organelles in different cells. In some examples, the segmentation can identify types of organelles such as a healthy or unhealthy nucleus, or a swollen or healthy mitochondria.

By generating the segmentation of the one or more images using the image processing neural network, the system can automate the generation of the target toxicity for the training example. The system can thus automate aspects of generating training data for training the toxicity prediction machine learning model, allowing for the processing and segmentation of a larger number of images, e.g., compared to manual segmentation by human raters. In addition, processing the one or more images using the image processing neural network can result in more objective and reliable segmentations, e.g., as compared to manual segmentation by human raters, allowing for the generation of more accurate and consistent target toxicity for the training example. The system can thus use the image processing neural network to generate a large number of high-quality training examples for training the toxicity prediction machine learning model.

The image processing neural network can have any appropriate neural network architecture that enables the image processing neural network to perform its described functions. In particular, the image processing neural network can include any appropriate types of neural network layers (e.g., fully connected layers, message passing layers, convolutional layers, attention layers, recurrent layers, pooling layers, and so forth), in any appropriate number (e.g., 5 layers, or 10 layers, or 50 layers), and connected in any appropriate configuration (e.g., as a directed graph of layers).

As a particular example, the image processing neural network can be implemented as a U-Net or a convolutional neural network. An example U-Net is described in further detail in Ronneberger, O., et al., U-Net: Convolutional Networks for Biomedical Image Segmentation, arXiv: 1505.04597 (2015).

The image processing neural network can be trained on a set of training examples by a machine learning technique. Each of the training examples can include (i) a training input that includes one or more images of a training cell culture, and (ii) a target segmentation of the one or more images of the training cell culture. For each training example, the system can train the image processing neural network to reduce a discrepancy between: (i) a segmentation generated by the image processing neural network by processing the training input of the training example, and (ii) the target segmentation of the training example.

For example, the system can evaluate an objective function that measures an error (e.g., a cross-entropy loss) for each training example between (i) a segmentation generated by the image processing neural network by processing the training input of the training example, and (ii) the target segmentation of the training example. The system can determine gradients of the objective function with respect to current values of parameters of the image processing neural network, e.g., using backpropagation. The system can then update the current values of the parameters of the image processing neural network using the gradients, e.g., by the update rule of an appropriate gradient descent optimization algorithm, e.g., RMSprop or Adam.

The system can determine the target toxicity for the training example based at least in part on the segmentation of the one or more images of the cell culture. For example, the system can identify a quantity of nuclei or a size of the nuclei in the segmentation. The system can determine the target toxicity, e.g., by comparing the quantity of nuclei or size of the nuclei relative to the quantity of nuclei or size of the nuclei in the cell culture prior to exposing the cell culture to the training molecule. As another example, the system can determine the target toxicity by comparing a quantity of a certain type of morphological feature relative to the quantity of the type of morphological feature prior to exposing the cell culture to the training molecule.

Figure 5:
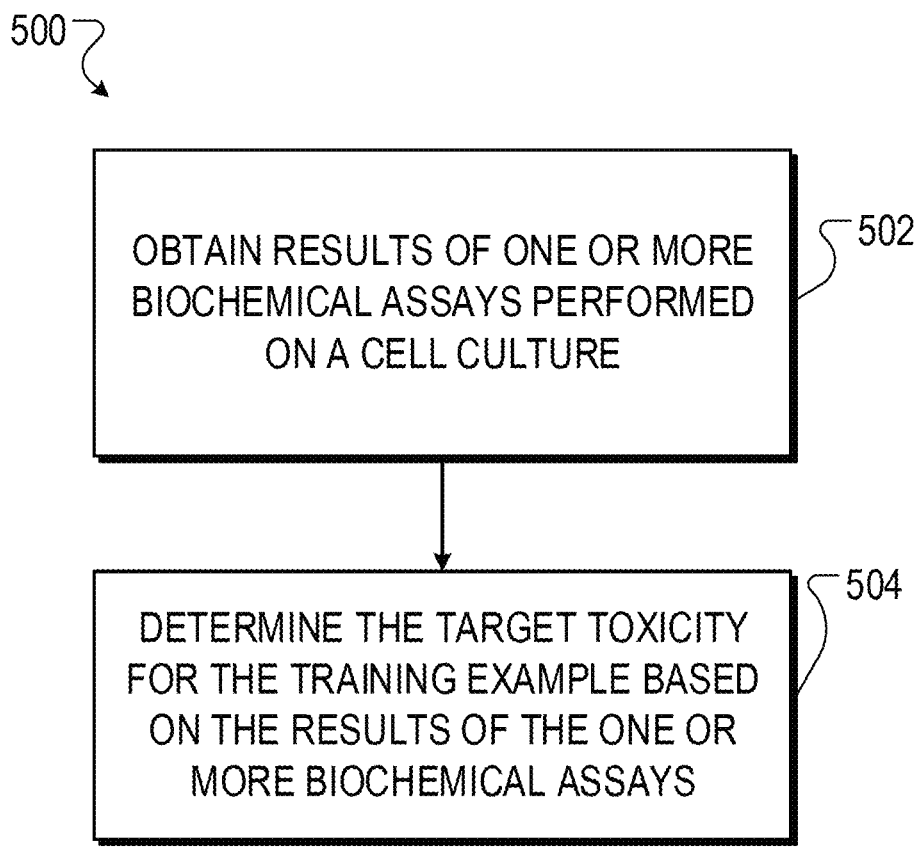
FIG. 5 is a flow diagram of an example process for generating a target toxicity for a training example for training a toxicity prediction machine learning model.

FIG. 5 is a flow diagram of an example process 500 for generating a target toxicity for a training example for training a toxicity prediction machine learning model. For convenience, the process 500 will be described as being performed by a system of one or more computers located in one or more locations. For example, a toxicity prediction system, e.g., the toxicity prediction system 100 of FIG. 1A, appropriately programmed in accordance with this specification, can perform the process 500.

The system obtains results of one or more biochemical assays performed on a cell culture (step 502). The cell culture can have been exposed to the training molecule of the training example at the dose value specified by the training example.

The system determines the target toxicity for the training example based on the results of the one or more biochemical assays (step 504). The one or more biochemical assays can include a cytotoxicity assay, or a cell viability assay, or both.

The cytotoxicity assay can measure the extent to which the training molecule harms or kills cells, e.g., by evaluating cell membrane integrity, metabolic activity, apoptosis, or necrosis. The result of the cytotoxicity assay can include, for example, a percent cell viability that compares the number of cells in the cell culture that has been exposed to the training molecule to the number of cells in a control cell culture, e.g., a cell culture that has not been exposed to the training molecule, or a measure of LDH released by the cells in the cell culture. Some examples of cytotoxicity assays include Methylthiazolyldiphenyl-tetrazolium Bromide (MTT) assays, Lactate Dehydrogenase (LDH) assays, or flow cytometry.

The cell viability assay can measure the ability of cells to survive and remain metabolically active after exposure to the training molecule, e.g., by evaluating the number of cells that are alive, or the ability of cells to maintain metabolic activity. The result of the cell viability assay can include, for example, a percent cell viability that compares the number of cells in the cell culture that has been exposed to the training molecule to the number of cells in a control cell culture, or an optical density value. Some examples of cell viability assays include Methylthiazolyldiphenyl-tetrazolium Bromide (MTT) assays or adenosine triphosphate (ATP) bioluminescence assays.

Figure 6:
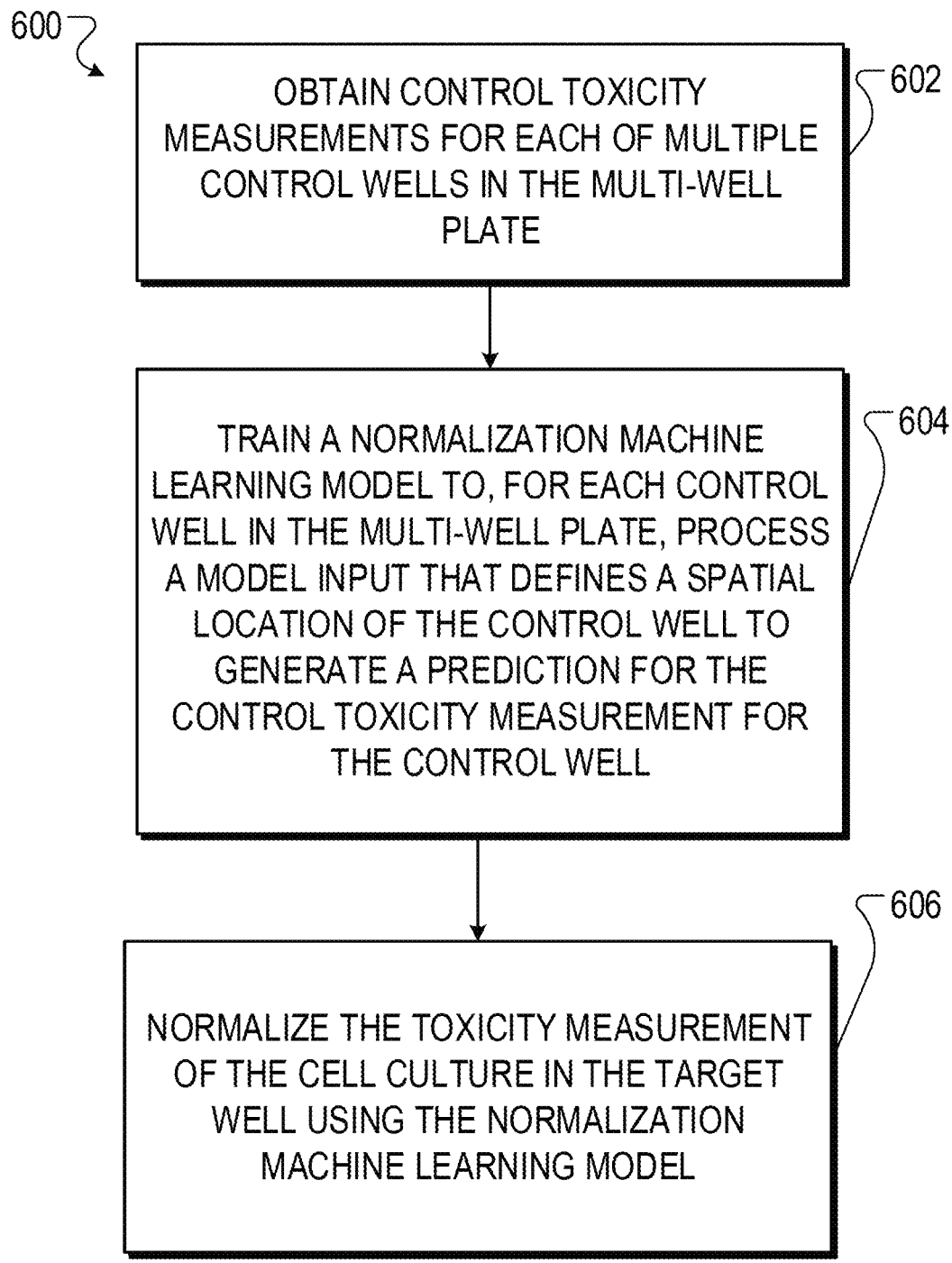
FIG. 6 is a flow diagram of an example process for normalizing a toxicity measurement of a cell culture.

FIG. 6 is a flow diagram of an example process 600 for normalizing a toxicity measurement of a cell culture. For convenience, the process 600 will be described as being performed by a system of one or more computers located in one or more locations. For example, a toxicity prediction system, e.g., the toxicity prediction system 100 of FIG. 1A, appropriately programmed in accordance with this specification, can perform the process 600.

As described above with reference to FIG. 2, the cell culture is located in a target well in a multi-well plate. The system can obtain a toxicity measurement of the cell culture located in the target well. The system can perform the process 600 to normalize the toxicity measurement.

A multi-well plate is a plate with multiple wells. Each well is a depression on the plate and can hold a particular volume of sample, e.g., 0.1 mL, 2 mL, 5 mL, or any appropriate volume of cell culture. The multiple wells are arranged on the multi-well plate such that each well is located at a different spatial location on the multi-well plate. In some examples, the spatial location of each well can be identified by a row index and a column index. As an example, a multi-well plate with 6 wells can have a 2 row and 3 column rectangular arrangement of wells. As another example, a multi-well plate with 48 wells can have a 6 row and 8 column rectangular arrangement of wells. In other examples, the multi-well plate can have, e.g., 12, 24, 96, etc., wells.

The system obtains control toxicity measurements for each of multiple control wells in the multi-well plate (step 602). For example, the control toxicity measurements can be based on any one or more dimensions of toxicity, e.g., cell morphology, membrane integrity, metabolic activity, or a cell count.

The cell culture located in each of the control wells is not exposed to the training molecule. The multi-well plate can include, e.g., 2, 3, 8, or any appropriate number of control wells. In some examples, the control wells are located at predefined spatial positions on the multi-well plate, e.g., in the first few columns of the first row of the multi-edge plate, in the first few rows of the first column of the multi-well plate, along the border of the multi-well plate, near the center of the multi-well plate, or near the corners of the multi-well plate.

The system trains a normalization machine learning model to, for each control well in the multi-well plate, process a model input that defines a spatial location of the control well to generate a prediction for the control toxicity measurement for the control well (step 604). For example, the model input can define the spatial location of the control well using a row index and a column index.

The normalization machine learning model can be implemented as any appropriate type of machine learning model that can generate a prediction for the control toxicity measurement for a given control well. As particular examples, the normalization machine learning model can be a kernel regression or a ridge regression model, a decision tree, or a neural network.

The system can train the normalization model machine learning model specific to the multi-well plate. For example, the normalization model can be trained on a set of training examples for the multi-well plate by a machine learning technique. Each of the training examples can include (i) a training input that includes a spatial location of a training control well, and (ii) a target control toxicity measurement for the training control well. For each training example, the system can train the normalization machine learning model to reduce a discrepancy between: (i) a control toxicity measurement generated by the normalization machine learning model by processing the training input of the training example, and (ii) the target control toxicity measurement of the training example.

In examples where the normalization machine learning model is a ridge regression model, the system can learn a vector of regression coefficients that minimizes an objective function that measures an error (e.g., a residual sum of squares) between the control toxicity measurements generated by the normalization machine learning model by processing the training inputs of the training examples, and the target control toxicity measurements of the training examples.

In examples where the normalization machine learning model is a kernel regression model, the system can learn a weight for each training example that minimizes an objective function that measures a weighted sum of squared errors between the control toxicity measurements generated by the normalization machine learning model by processing the training inputs of the training examples, and the target control toxicity measurements of the training examples, where the weights are determined based on a kernel function that measures the similarity between each training input and each other training input.

As another example, the normalization machine learning model can be a neural network. The system can evaluate an objective function that measures an error (e.g., an absolute error) for each training example between (i) a control toxicity measurement generated by the normalization machine learning model by processing the training input of the training example, and (ii) the target control toxicity measurement of the training example. The system can determine gradients of the objective function with respect to current values of parameters of the normalization model, e.g., using backpropagation. The system can then update the current values of the parameters of the normalization model using the gradients, e.g., by the update rule of an appropriate gradient descent optimization algorithm, e.g., RMSprop or Adam.

The system normalizes the toxicity measurement of the cell culture in the target well using the normalization machine learning model (step 606).

For example, the system can process a model input that defines a spatial location of the target well using the normalization machine learning model to generate a prediction for a control toxicity measurement for the target well. For example, the model input can define the spatial location of the target well using a row index and a column index.

The system can normalize the toxicity measurement of the cell culture in the target well based on the prediction for the control toxicity measurement for the target well. For example, the system can divide the toxicity measurement of the cell culture in the target well by the prediction for the control toxicity measurement for the target well that was generated by the normalization machine learning model.

Thus the system can account for noise in the toxicity measurements, e.g., due to temperature variations across locations of the multi-well plate, evaporation across locations of the multi-well plate, or variations in the number of cells placed in different wells of the multi-well plate. Thus the system can generate training examples with more accurate target toxicities, and allow for training the toxicity prediction machine learning model to generate more accurate toxicity predictions.

Figure 7:
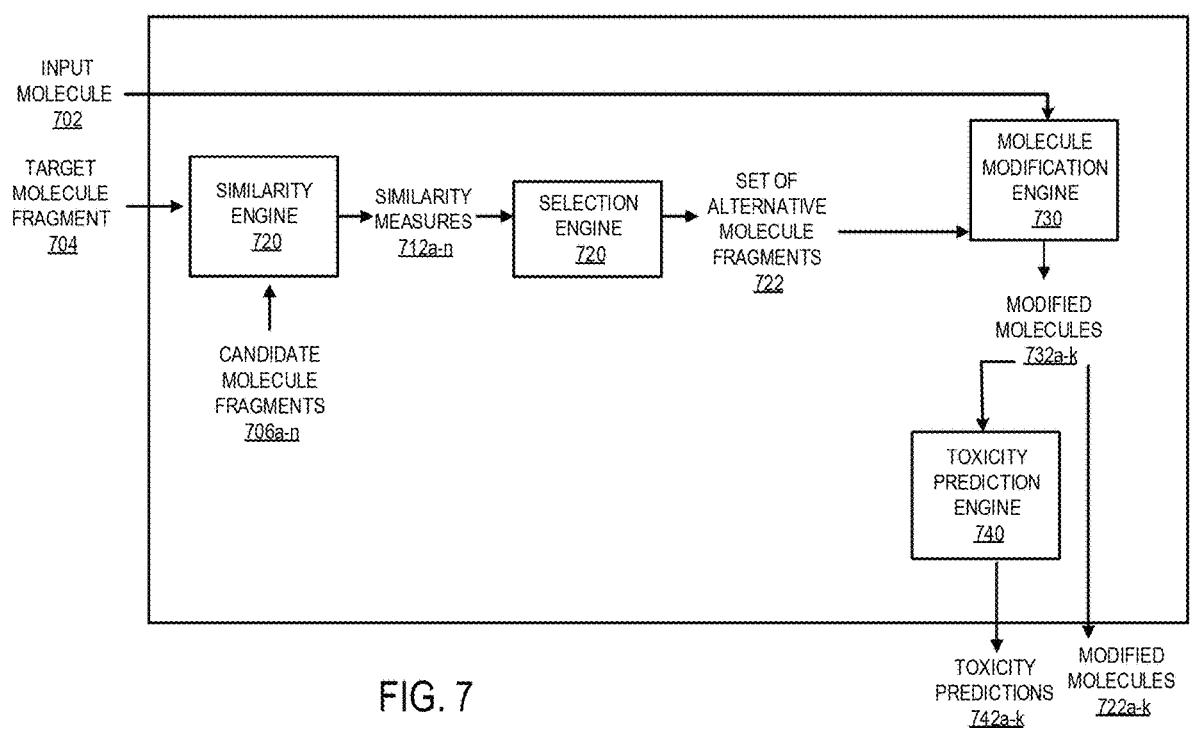
FIG. 7 shows an example molecule modification system.

FIG. 7 shows an example molecule modification system 700. The molecule modification system 700 is an example of a system implemented as computer programs on one or more computers in one or more locations in which the systems, components, and techniques described below are implemented.

The molecule modification system 700 can generate data defining multiple molecules 722*a-k* for an input molecule 702. For example, the input molecule 702 can be a molecule of interest, e.g., for inclusion in a therapeutic, but may have toxic effects. The molecule modification system 700 can generate data defining the molecules 722*a-k* that are each a modified version of the input molecule 702. In some cases, the molecules 722*a-k* have fewer toxic effects or a diminished severity of toxic effects, while retaining other properties of the input molecule 702 that are desirable for therapeutic uses, e.g., binding affinity for a binding site, solubility, or excretion properties, etc.

In some implementations, the molecule modification system 700 can be part of the toxicity prediction system 100 described above with reference to FIG. 1A or the toxicity analysis system 1300 described below with reference to FIG. 13A. In some implementations, the molecule modification system 700, the toxicity prediction system 100, and/or the toxicity analysis system 1300 can be subsystems of another system. In some implementations, the molecule modification system 700, the toxicity prediction system 100, and/or the toxicity analysis system 1300 can share one or more components, such as the toxicity prediction machine learning model 120 described with reference to FIG. 1A.

The molecule modification system 700 is configured to generate data defining multiple modified molecules 722*a-k* for the input molecule 702. In particular, each of the modified molecules 722*a-k* is a modified version of the input molecule 702, where a target molecule fragment 704 is replaced by a respective alternative molecule fragment.

To generate the data defining the modified molecules 722*a-k*, the system 700 obtains data identifying the input molecule 702 and data identifying the target molecule fragment 704 of the input molecule 702.

The data identifying the input molecule 702 can include any appropriate data identifying the molecule. An example input molecule 702 is shown below in FIG. 12A.

In some examples, the data identifying the input molecule 702 can include a textual representation of the molecule, e.g., a SMILES string identifying the molecule or an International Chemical Identifier (InCHI). In some examples where the input molecule 702 is a protein, the data identifying the input molecule 702 can include data defining an amino acid sequence of the protein. In some examples where the input molecule 702 is a nucleic acid, the data identifying the input molecule 102 can include data defining a nucleic acid sequence of the nucleic acid.

The data identifying the target molecule fragment 704 can include any appropriate data identifying a molecule fragment of the molecule. An example target molecule fragment 704 is shown below in FIG. 12A.

In some examples, the data identifying the target molecule fragment 704 can include a textual representation of the molecule fragment. For example, the data identifying the target molecule fragment 704 can include a subsequence of the text of the SMILES string identifying the molecule, where the subsequence corresponds to the target molecule fragment 704.

In some implementations, the system 700 can generate the data identifying the target molecule fragment 704. For example, the system 700 can process the data identifying the input molecule 702 to identify multiple fragments of the input molecule 702. In some examples, the system 700 can fragment the input molecule 702 using retrosynthetic fragmentation, e.g., using the Breaking of Retrosynthetically Interesting Chemical Substructures (BRICS) algorithm. In some examples, the system can fragment the input molecule 702 using functional group-based fragmentation, e.g., using a pattern matching algorithm, or graph-based fragmentation, e.g., using the Bron-Kerbosch algorithm.

In some examples, for each identified fragment of the input molecule 702, the system 700 can obtain data identifying the fragment as data identifying the target molecule fragment 704. Thus, the system 700 can generate modified molecules for the input molecule 702 that have different fragments of the input molecule 702 replaced.

The molecule modification system 700 can obtain the data identifying the input molecule 702 or the data identifying the target molecule fragment 704 from any appropriate source, e.g., from a user or from another system, by way of an appropriate interface, e.g., an application programming interface (API) or a user interface (e.g., a graphical user interface). As an example, the other system can be an upstream system that generates data identifying molecules, e.g., in a drug discovery workflow.

As a particular example, the molecule modification system 700 can provide a graphical user interface that allows a user to provide inputs that identify the target molecule fragment 704. For example, the graphical user interface can include a user interface element that allows the user to input a textual representation of the target molecule fragment 704.

As another example, the graphical user interface can allow the user to identify the target molecule fragment 704 from a visualization of the input molecule 702 that depicts, e.g., atoms and bonds of the input molecule 702. The graphical user interface can include a user interface element that allows the user to highlight or select one or more atoms or bonds of the input molecule 702 to include in the target molecule fragment 704. The molecule modification system 700 can generate the data identifying the target molecule fragment 704 based on the atoms or bonds selected by the user.

The visualization of the input molecule can be generated based on textual or graphical data input by the user. For example, the graphical user interface can include a user interface element that allows the user to draw the input molecule 702, and the graphical user interface can provide a visualization of the input molecule 702 for display. As another example, the graphical user interface can include a user interface element that allows the user to input a textual representation of the input molecule 702. The molecule modification system 700 can process the textual representation to generate a visualization of the input molecule 702, and the graphical user interface can provide the visualization of the input molecule 702 for display.

In some examples, the target molecule fragment 704 can be a target molecule fragment that is predicted to contribute to toxicity. For example, the molecule modification system 700 can provide the data identifying the input molecule 702 as input to a toxicity analysis system, e.g., the toxicity analysis system 1300 of FIG. 13A, that generates a toxicity score for each molecule fragment in the input molecule 702. The molecule modification system 700 can select a target molecule fragment from the input molecule 702 based on the toxicity scores for multiple molecule fragments in the input molecule 702. For example, the molecule modification system 700 can select the molecule fragment with the highest toxicity score as the target molecule fragment.

The system 700 includes a database of candidate molecule fragments 706a-n. The system 700 selects a set of alternative molecule fragments 722 for the target molecule fragment 704 from the database of candidate molecule fragments 706a-n.

The database of candidate molecule fragments 706a-n includes a large number, e.g., over 100, 1,000, or 10,000, candidate molecule fragments. Each candidate molecule fragment in the database of candidate molecule fragments 706a-n can include, e.g., an atom, a group of atoms, or a functional group.

In some examples, the database of candidate molecule fragments 706a-n can have been generated by fragmenting multiple training molecules. For example, the system can fragment each training molecule into multiple candidate molecule fragments. In some examples, the system can fragment each training molecule using retrosynthetic fragmentation, e.g., using the Breaking of Retrosynthetically Interesting Chemical Substructures (BRICS) algorithm. In some examples, the system can fragment each training molecule using functional group-based fragmentation, e.g., using a pattern matching algorithm, or graph-based fragmentation, e.g., using the Bron-Kerbosch algorithm.

In some examples, the system can filter the fragments generated from the multiple training molecules. For example, in some cases multiple training molecules can include the same fragment. The system can maintain a count of the number of appearances of each fragment in the multiple training molecules. The system can refrain from including fragments for which the count does not meet a threshold number in the database of candidate molecule fragments 706a-n.

For each candidate molecule fragment in the database of candidate molecule fragments 706a-n, the system can determine a respective similarity measure between (i) an embedding of the target molecule fragment, and (ii) an embedding of the candidate molecule fragment. A higher similarity measure for a candidate molecule fragment can represent that the candidate molecule fragment is more similar to the target molecule fragment, and is more likely to be a bioisostere for the target molecule fragment.

To determine similarity measures 712a-n, the system 700 can process, for each candidate molecule fragment in the database of candidate molecule fragments 706a-n, data identifying the candidate molecule fragment and the target molecule fragment using a similarity engine 710 to generate the respective similarity measure.

For each candidate molecule fragment, the similarity engine 710 can obtain an embedding of the target molecule fragment and the candidate molecule fragment. The similarity engine 710 can determine the similarity measure based on the distance, e.g., the cosine distance, between the embedding of the target molecule fragment and the embedding of the candidate molecule fragment.

The similarity engine 710 can generate the embedding for the target molecule fragment 704 by target molecule fragment 704 using a neural network.

In some examples, the similarity engine 710 can generate the embedding for the candidate molecule fragment using the neural network as described above. In some examples, the similarity engine 710 can maintain pre-computed embeddings, e.g., generated by the neural network, for each of the candidate molecule fragments 706a-n. Thus the system does not have to generate embeddings for the same candidate molecule fragments 706a-n given different target molecule fragments, reducing the consumption of computational resources such as computing time and power that would otherwise be required to generate the embeddings.

The system 700 can include a selection engine 720. The selection engine 720 can select the set of alternative molecule fragments 722 from the similarity measurements 712a-n for the candidate molecule fragments 706a-n. For example, the selection engine 720 can select candidate molecule fragments for which the similarity measures indicate a high similarity to the target molecule fragment 704. An example set of alternative molecule fragments 722 is shown below in FIGS. 12B-12C.

The system 700 can include a modification engine 730. The modification engine 730 can generate data defining the modified molecules 732a-k. For example, for each alternative molecule fragment in the set of alternative molecule fragments 722, the modification engine 730 can generate data defining a modified molecule that includes the alternative molecule fragment in place of the target molecule fragment 704. As a particular example, for each alternative molecule fragment, the modification engine 730 can replace the subsequence of the textual representation of the input molecule 702 that corresponds to the target molecule fragment 704, with a textual representation of the alternative molecule fragment, to generate a textual representation of the modified molecule that includes the alternative molecule fragment.

The system 700 can include a toxicity prediction engine 740. The toxicity prediction engine 740 can generate toxicity predictions 742a-k for the modified molecules 732a-k. For example, the toxicity prediction engine 740 can generate a respective toxicity prediction for each of the modified molecules 732a-k. In some examples, the toxicity prediction engine 740 can provide data identifying each modified molecule 732a-k and a dose value as input to a toxicity prediction machine learning model, e.g., the toxicity prediction machine learning model 120 described above with reference to FIG. 1A, to generate the toxicity predictions 742a-k. In some examples, the dose value is a predefined dose value.

In some examples, for each modified molecule 722a-k, and for each of multiple predefined dose values, the toxicity prediction engine 740 can provide data identifying the modified molecule to a toxicity prediction system, e.g., the toxicity prediction system 100 of FIG. 1A, to generate a toxicity dose-response curve for the modified molecule. In these examples, the toxicity prediction engine 740 can generate a summarized toxicity prediction for each modified molecule. For example, for each modified molecule, the toxicity prediction engine 740 can derive a statistic summarizing the toxicity dose-response curve, e.g., the area under the curve.

After generating the data identifying the modified molecules 722a-k and the toxicity predictions 742a-k, the molecule modification system 700 can output the data identifying the modified molecules 722a-k, the data identifying the toxicity predictions 742a-k, or both. For example, the molecule modification system 700 can present a visual representation of one or more of the modified molecules 722a-k on a display of a user device. As another example, the molecule modification system 700 can store the data identifying the modified molecules 722a-k, the data identifying the toxicity predictions 742a-k, or both, in a memory. As another example, the molecule modification system 700 can transmit data defining the data identifying the modified molecules 722a-k, the data identifying the toxicity predictions 742a-k, or both, over a data communication network. As another example, the molecule modification system 700 can provide the data identifying the modified molecules 722a-k, the data identifying the toxicity predictions 742a-k, or both to a system that performs downstream processing based on the data identifying the modified molecules 722a-k, the data identifying the toxicity predictions 742a-k, or both.

In some implementations, the molecule modification system 700 or a downstream system can select a modified molecule from the multiple modified molecules 722a-k for physical synthesis based at least in part on the toxicity predictions 742a-k. For example, the molecule modification system 700 can select one or more modified molecules that have the lowest toxicity predictions for physical synthesis.

In some implementations, the molecule modification system 700 or another downstream system can physically synthesize the modified molecule selected for physical synthesis. In some examples, the system can perform a physical experiment to measure an experimental toxicity of the modified molecule.

Figure 8:
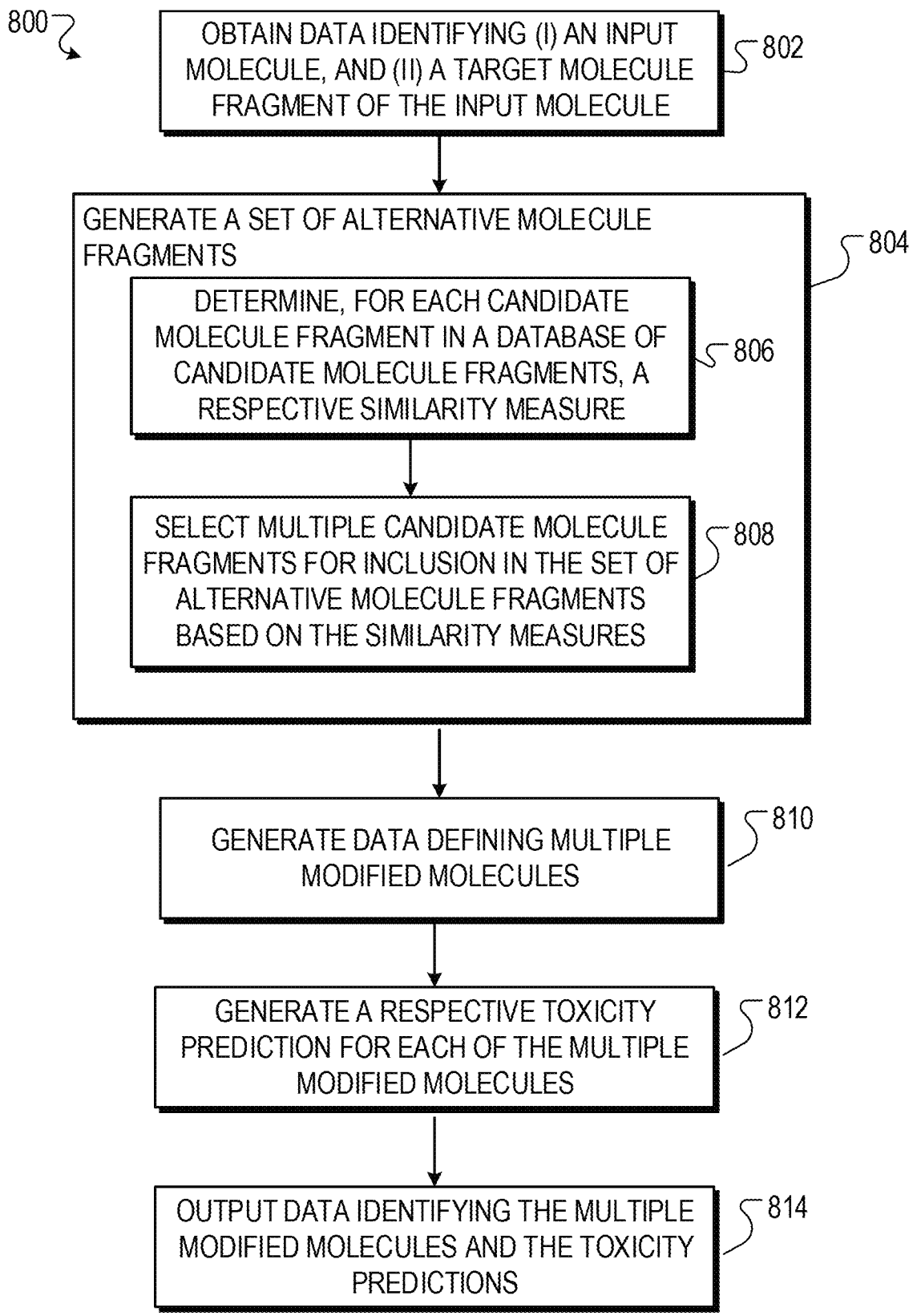
FIG. 8 is a flow diagram of an example process for generating data defining multiple modified molecules.

FIG. 8 is a flow diagram of an example process 800 for generating data defining multiple modified molecules. For convenience, the process 800 will be described as being performed by a system of one or more computers located in one or more locations. For example, a molecule modification system, e.g., the molecule modification system 700 of FIG. 7, appropriately programmed in accordance with this specification, can perform the process 800.

The system obtains data identifying: (i) an input molecule, and (ii) a target molecule fragment of the input molecule (step 802). In some examples, the system can obtain the data identifying the input molecule and the data identifying the target molecule fragment from any appropriate source, e.g., from a user or from an upstream system that generates data identifying an input molecule, e.g., in a drug discovery workflow. The system can obtain the data identifying the input molecule by way of an appropriate interface, e.g., an application programming interface (API) or a user interface (e.g., a graphical user interface).

The system generates a set of alternative molecule fragments (step 804). The system performs steps 804-808 to generate the set of alternative molecule fragments.

For example, the system determines, for each candidate molecule fragment in a database of candidate molecule fragments, a respective similarity measure (step 806). For example, the system can determine the respective similarity measure between: (i) an embedding of the target molecule fragment, and (ii) an embedding of the candidate molecule fragment.

The system can generate the embedding of the target molecule fragment using the neural network. For example, the system can process an identifier of the target molecule fragment in the database of candidate molecule fragments, or a graph representation of the target molecule fragment, using the neural network.

The system can determine the respective embedding of each candidate molecule fragment as the embedding generated by processing the candidate molecule fragment using the neural network. In some examples, the system can generate the embedding by processing the candidate molecule fragment using the neural network. For example, the system can process an identifier of the candidate molecule fragment in the database of candidate molecule fragments, or a graph representation of the candidate molecule fragment, using the neural network.

In some examples, the system can obtain the embedding, e.g., as a pre-computed embedding maintained by the system for the candidate molecule fragment. The system can thus reduce latency and consumption of computational resources compared to generating embeddings of the candidate molecule fragments repeatedly.

In particular, the system can generate the embeddings using an embedding subnetwork of the neural network. The neural network can include an embedding subnetwork that is configured to process data identifying a set of input molecule fragments to generate a respective embedding of each input molecule fragment.

In some examples, the embedding subnetwork is parametrized by an array of embeddings that includes a respective embedding for each candidate molecule fragment in the database of candidate molecule fragments. The embedding subnetwork receives an identifier of an input molecule fragment in the database of candidate molecule fragments (e.g., in the form of a one-hot embedding). The embedding subnetwork maps the input molecule fragment to its corresponding embedding as defined by the array. In some cases, the input molecule fragment may not be included in the database of candidate molecule fragments, and thus may not have a corresponding entry in the array. In these cases the system can generate an embedding for the input molecule fragment that is an average of embeddings of candidate molecule fragments from the database of candidate fragments that are included in the input molecule fragment.

In some examples, the embedding subnetwork is configured to process data characterizing a respective chemical structure of each input molecule fragment in a set of input molecule fragments using one or more embedding neural network layers. In these examples, the embedding subnetwork can process a graph representation of the chemical structure of the input molecule fragment. The graph representation represents the input molecule fragment using a set of nodes and a set of edges. Each node in the graph representation can represent a respective atom in the input molecule fragment. Each edge in the graph that connects a pair of nodes can represent, e.g., a bond between the two atoms represented by the pair of nodes, or that the two atoms represented by the pair of nodes are separated by less than a threshold distance, e.g., 8 Angstroms. Each node in the graph representation can be associated with a set of features, e.g., elemental type of the atom, of the atom represented by the node. Each edge in the graph can be associated with a set of features, e.g., the type of bond, between the atoms represented by the nodes for which the edge connects.

The embedding subnetwork can include an encoder block, a sequence of one or more message passing layers, and a decoder block. The encoder block can process the set of features associated with each node to generate an embedding associated with the node. In some examples, the encoder block can process the set of features associated with each edge to generate an embedding associated with the edge. The message passing layers can iteratively update the embeddings associated with the nodes using message passing operations that propagate information along the edges. In some examples, the message passing layers can update the embeddings associated with the edges. The decoder block can process the embeddings associated with the nodes to generate the embedding of the input molecule fragment. For example, the decoder block can pool (e.g., average pool or max pool) the embeddings associated with the nodes to generate the embedding of the input molecule fragment. In some examples, the decoder block can process the embeddings associated with the nodes and the embeddings associated with the edges to generate the embedding of the input molecule fragment. A suitable architecture for a graph neural network is described in Gilmer, J., et al., Neural Message Passing for Quantum Chemistry, arXiv: 1704.01212 (2017).

The neural network can also include a prediction subnetwork. The prediction subnetwork is described in further detail with reference to FIG. 11.

The system selects multiple candidate molecule fragments from the database of candidate molecule fragments for inclusion in the set of alternative molecule fragments based on the similarity measures (step 808).

As an example, the system can select the multiple candidate molecule fragments with embeddings that have a highest similarity to the embedding of the target molecule fragment for inclusion in the set of alternative molecule fragments.

The system generates data defining multiple modified molecules (step 810). Each modified molecule is a modified version of the input molecule where the target molecule fragment is replaced by a respective alternative molecule fragment from the set of alternative molecule fragments.

The system generates a respective toxicity prediction for each of the multiple modified molecules (step 812). For example, for each of the multiple modified molecules, the system can process a model input that characterizes the modified molecule using a toxicity prediction machine learning model to generate a model output that defines the toxicity prediction for the modified molecule. In some cases, the modified molecule retains certain properties of the input molecule, while having a different toxicity prediction.

An example toxicity prediction machine learning model is described above with reference to FIG. 1A. As a particular example, the toxicity prediction machine learning model can include a decision tree ensemble.

The system outputs data identifying the multiple modified molecules and the toxicity predictions for the multiple modified molecules (step 814).

In some examples, the system can determine properties of the multiple modified molecules, e.g., molecular weight, H-bond acceptors, or H-bond donors. The system can also provide data defining the properties for display on a user device.

In some examples, the system can determine a ranking of the multiple modified molecules based at least in part on the toxicity predictions for the plurality of modified molecules. For example, the ranking can be a ranking from lowest toxicity to highest toxicity.

In some examples, the ranking can be based at least in part on one or more other properties in addition to toxicity, including one or more of: synthetic accessibility, binding affinity, or solubility.

In some examples, the system can provide, for display on a user device, a visual representation of a ranked list of the multiple modified molecules. For example, the system can provide a two-dimensional (2D) representation of a chemical structure of each of the multiple modified molecules according to the ranking.

In some examples, the system can select a subset of one or more modified molecules, e.g., less than 50%, less than 10%, or less than 1%, of the modified molecules generated by the system for further processing, e.g., for inclusion in a drug, for physical synthesis, or further computational analysis, from the multiple modified molecules based on the ranking. For example, the system can select the one or more modified molecules that have the lowest toxicity in the ranking.

Further computational analysis can include, e.g., predicting the binding affinity for a binding site, e.g., using molecular docking or molecular dynamics simulations. Further computational analysis can be computationally intensive, and performing further computational analysis of all of the modified molecules generated by the system may be computationally infeasible. By selecting one or more modified molecules based on the ranking, the system performs further processing only on the selected modified molecules that are predicted to have lower toxicity. The system can thus filter the modified molecules to prioritize the selected modified molecules for further processing, reducing the consumption of computational resources, e.g., memory and computing power, otherwise required to perform further processing for a larger number or all of the multiple modified molecules.

Figure 9:
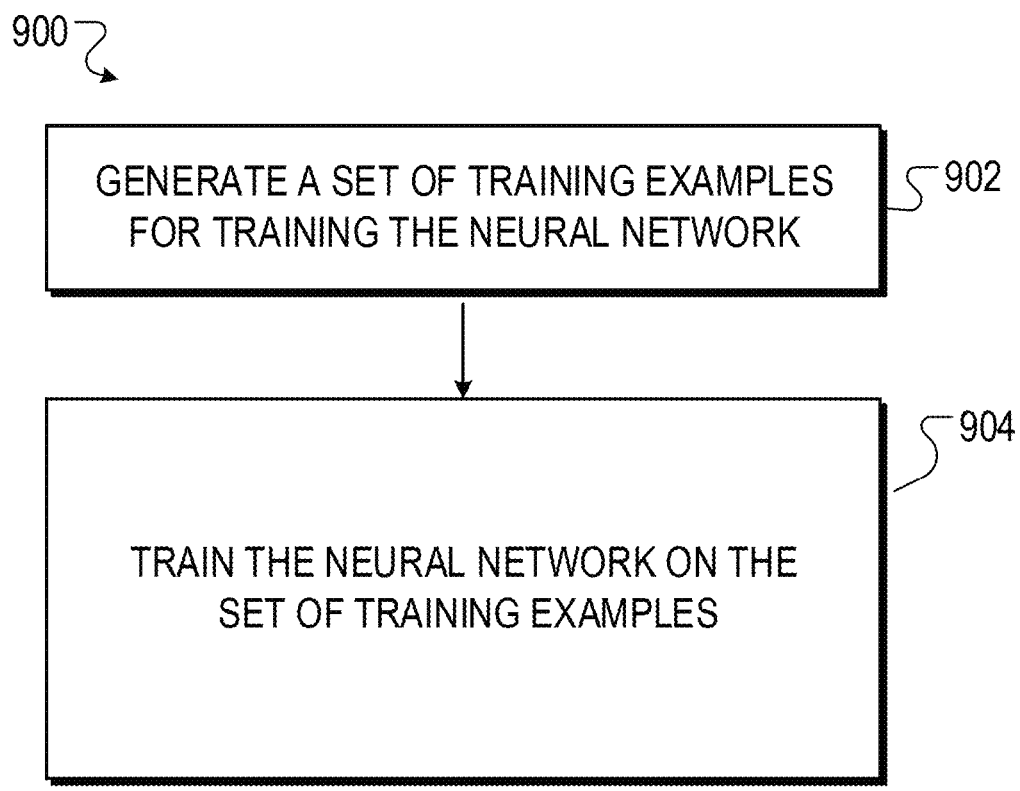
FIG. 9 is a flow diagram of an example process for training a neural network to perform a machine learning task.

FIG. 9 is a flow diagram of an example process 900 for training a neural network to perform a machine learning task. For convenience, the process 900 will be described as being performed by a system of one or more computers located in one or more locations. For example, a molecule modification system, e.g., the molecule modification system 700 of FIG. 7, appropriately programmed in accordance with this specification, can perform the process 900.

The system generates a set of training examples for training the neural network (step 902). Generating a training example for the set of training examples is described in further detail with reference to FIG. 10.

The system trains the neural network on the set of training examples (step 904). Training the neural network on the set of training examples is described in further detail with reference to FIG. 11.

Figure 10:
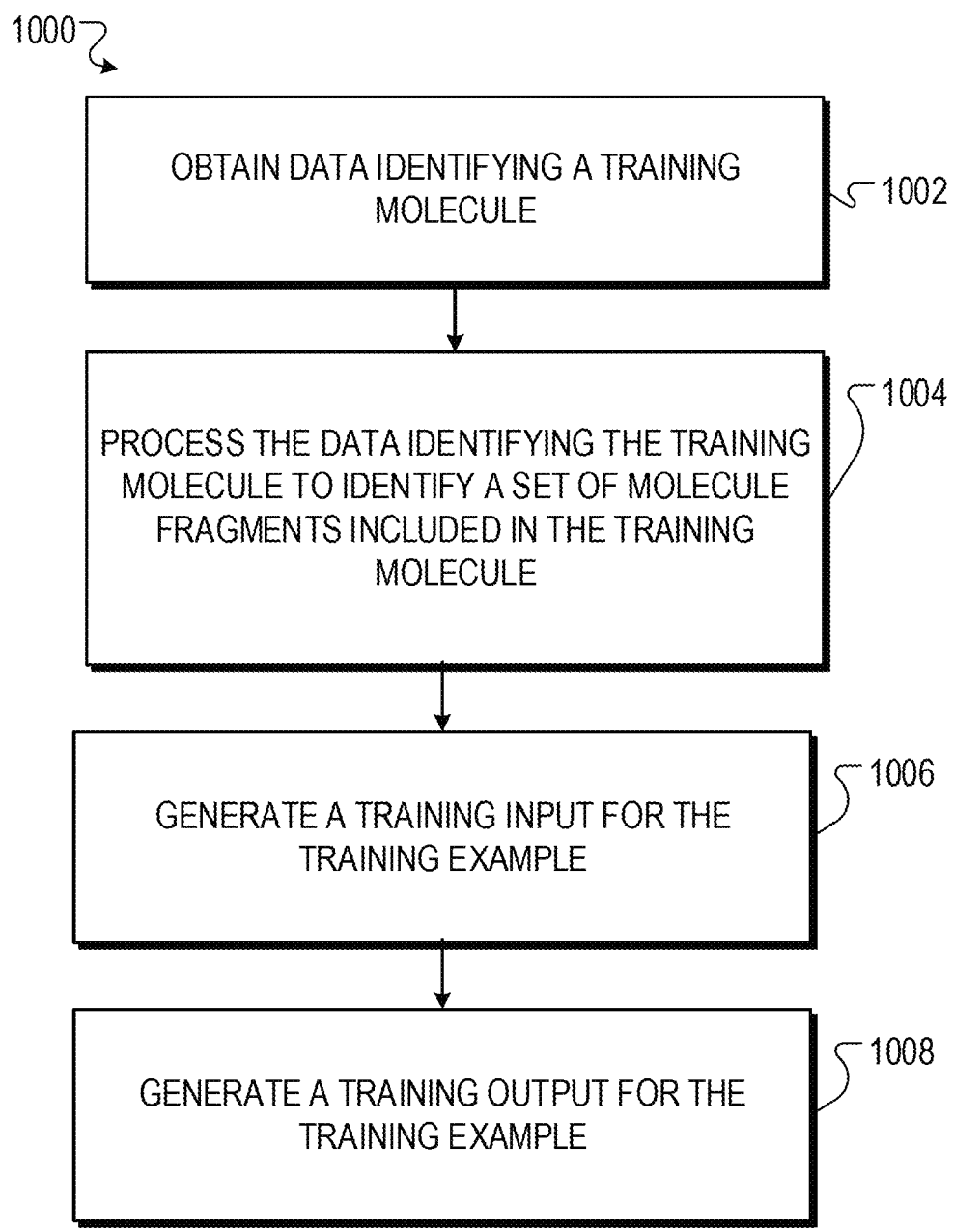
FIG. 10 is a flow diagram of an example process for generating a training example for training a neural network.

FIG. 10 is a flow diagram of an example process 1000 for generating a training example for training a neural network. For convenience, the process 1000 will be described as being performed by a system of one or more computers located in one or more locations. For example, a molecule modification system, e.g., the molecule modification system 700 of FIG. 7, appropriately programmed in accordance with this specification, can perform the process 1000.

The system performs the steps 1002-1008 to generate each training example of a set of training examples for training the neural network.

The system obtains data identifying a training molecule (step 1002). The data identifying the training molecule can include any appropriate data identifying the training molecule. For example, the data identifying the training molecule can include a textual representation of the molecule, e.g., a SMILES string identifying the training molecule.

The system processes the data identifying the training molecule to identify a set of molecule fragments included in the training molecule (step 1004). For example, the system can fragment each training molecule using retrosynthetic fragmentation, e.g., using the Breaking of Retrosynthetically Interesting Chemical Substructures (BRICS) algorithm. In some examples, the system can fragment each training molecule using functional group-based fragmentation, e.g., using a pattern matching algorithm, or graph-based fragmentation, e.g., using the Bron-Kerbosch algorithm.

In some examples, each of the set of molecule fragments is included in a database of candidate molecule fragments. In some cases, one or more of the molecule fragments is not included in the database of candidate molecule fragments. In these cases, the system can update the database of candidate molecule fragments to include the new molecule fragments.

The system generates a training input for the training example (step 1006). The training input includes all but one of the molecule fragments in the set of molecule fragments. For example, the system can select the one fragment to not be included in the training input randomly from the set of molecule fragments.

In some examples, the training input includes data identifying each of the molecule fragments except for the selected molecule fragment. As an example, the data identifying each of the molecule fragments can define the chemical structure of the molecule fragment. For example, the data identifying each of the molecule fragments can include, for each molecule fragment, a subsequence of the text of the SMILES string identifying the molecule, where the subsequence corresponds to the molecule fragment.

As another example, the data identifying each of the molecule fragments can include, for each molecule fragment, a unique numerical identifier for the molecule fragment. For example, each of the molecule fragments in the database can be indexed using a numerical identifier for the molecule fragment.

The system generates a target output for the training example (step 1008). The target output includes the one molecule fragment excluded from the training input.

In some examples, the training output includes data identifying the selected molecule fragment excluded from the training input. As an example, the data identifying the molecule fragment can define the chemical structure of the molecule fragment. For example, the data identifying the molecule fragment can a subsequence of the text of the SMILES string identifying the molecule, where the subsequence corresponds to the molecule fragment.

As another example, the data identifying the molecule fragments can include a unique numerical identifier for the molecule fragment, e.g., the unique numerical identifier assigned to the molecule fragment in the database.

In some examples, the system generates multiple training examples from one training molecule. For example, for each training example, the system can select a different molecule fragment to include in the target output for the training example, and different molecule fragments to include in the training input for the training example.

Figure 11:
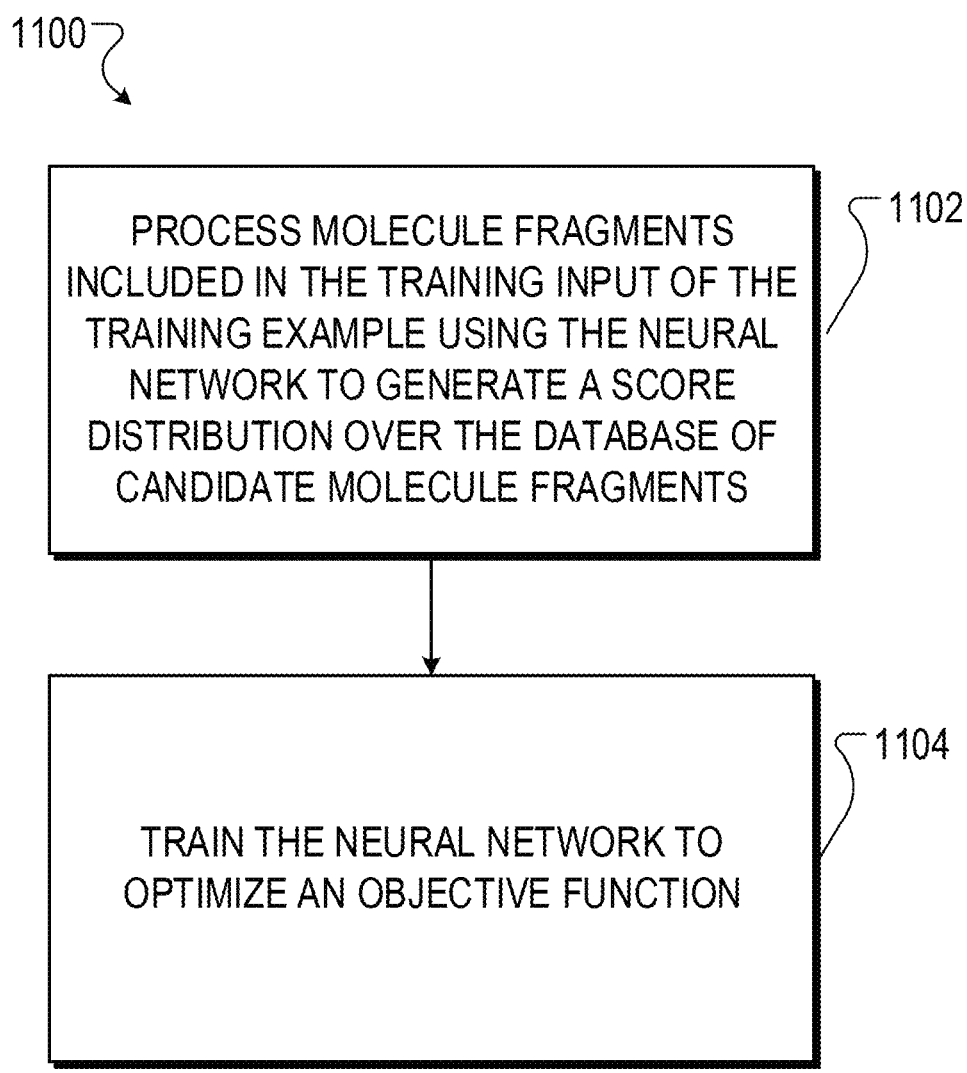
FIG. 11 is a flow diagram of an example process for training a neural network.

FIG. 11 is a flow diagram of an example process 1100 for training a neural network. For convenience, the process 1100 will be described as being performed by a system of one or more computers located in one or more locations. For example, a molecule modification system, e.g., the molecule modification system 700 of FIG. 7, appropriately programmed in accordance with this specification, can perform the process 1100.

The system can perform steps 1102-1104 for each training example in the set of training examples.

The system processes molecule fragments included in the training input of the training example using the neural network to generate a score distribution over the database of candidate molecule fragments (step 1102). For example, the system can provide data characterizing each of the molecule fragments of the training input using the embedding subnetwork of the neural network to generate a corresponding embedding for the molecule fragment. The system can combine (e.g., average or sum) the corresponding embeddings to generate a combined embedding.

The neural network can include a prediction subnetwork that is configured to process the embeddings of the input molecule fragments to generate a network output. As a particular example, the prediction subnetwork can generate a score distribution over the candidate molecule fragments in the database of candidate molecule fragments. The system can process the combined embedding using the prediction subnetwork to generate the score distribution. The score distribution can include a respective score for each candidate molecule fragment in the database.

As an example, the machine learning task can include predicting an identity of a molecule fragment included in a training molecule based on identities of one or more other molecule fragments included in the training molecule. As a particular example, the prediction subnetwork can generate a score distribution that includes a score representing the likelihood of a molecule fragment being included in the training molecule.

In some examples, the machine learning task can include predicting an identity of a molecule fragment included in a training example based on both: (i) identities of one or more other molecule fragments included in the training molecule, and (ii) a spatial arrangement of the one or more other molecule fragments included in the training molecule. The spatial arrangement of the one or more other molecule fragments included in the training molecule can be represented by data that defines, e.g., a respective center of mass (e.g., in 3D spatial coordinates) of each of the other molecule fragments.

In some examples, the prediction subnetwork can generate a predicted reconstruction of the chemical structure of the training molecule given the combined embedding. In these examples, the neural network performs an auto-encoding task.

The system trains the neural network to optimize an objective function (step 1104). The objective function measures an error between: (i) the score distribution over the database of candidate molecule fragments, and (ii) a molecule fragment specified by the target output of the training example. In some examples, the objective function can measure the error using a cross-entropy term. The molecule fragment specified by the target output of the training example is included in the database of candidate molecule fragments, so that the score distribution over the database of candidate molecule fragments includes a predicted score for the molecule fragment specified by the target output.

The system can determine gradients of the objective function with respect to current values of parameters of the neural network, e.g., using backpropagation. The system can then update the current values of the parameters of the neural network using the gradients, e.g., by the update rule of an appropriate gradient descent optimization algorithm, e.g., RMSprop or Adam.

In some examples, the system can train the neural network by training the prediction subnetwork and the embedding subnetwork. For example, the system can backpropagate gradients of the objective function through the prediction subnetwork and into the embedding subnetwork of the neural network.

In some examples, the embedding subnetwork is parametrized by an array of embeddings that comprises a respective embedding for each candidate molecule fragment in the database of candidate molecule fragments. In these examples, the system can backpropagate gradients of the objective function through the array of embeddings that parametrize the embedding subnetwork of the neural network.

In some examples, the embedding subnetwork is configured to process data characterizing a respective chemical structure of each input molecule fragment in a set of input molecule fragments using one or more embedding neural network layers. In these examples, the system can backpropagate gradients of the objective function through the embedding neural network layers of the embedding subnetwork of the neural network.

As another example, the embedding subnetwork can be part of an autoencoder neural network that also includes a decoder subnetwork. The autoencoder neural network can be trained on a set of training examples that each includes (i) a training input that includes all but one of the molecule fragments in the set of molecule fragments included in the training molecule, and (ii) a target output that includes all of the molecule fragments in the set of molecule fragments included in the training molecule. For each training example, the system can process the training input using the embedding subnetwork, e.g., an RNN, to generate an embedding of all but one of the molecule fragments in the set of molecule fragments included in the training molecule. The system can process the embedding using the decoder subnetwork, e.g., an autoregressive language model such as an RNN or Transformer neural network, to generate data characterizing all of the molecule fragments in the set of molecule fragments included in the training molecule. The system can train the autoencoder neural network to optimize an objective function that measures an error (e.g., a reconstruction error) between (i) data characterizing all of the molecule fragments in the set of molecule fragments included in the training molecule that has been generated using the embedding subnetwork and the decoder subnetwork and (ii) the data characterizing all of the molecule fragments in the set of molecule fragments included in the training molecule of the target output.

The system can determine gradients of the objective function with respect to current values of parameters of the autoencoder neural network, e.g., using backpropagation. The system can then update the current values of the parameters of the autoencoder neural network using the gradients, e.g., by the update rule of an appropriate gradient descent optimization algorithm, e.g., RMSprop or Adam.

As another example, the autoencoder neural network can be trained on a set of training examples that each includes (i) a training input that includes a set of molecule fragments included in a training molecule, and (ii) a target output that includes the set of molecule fragments of the training input. For each training example, the system can process the training input using the embedding subnetwork, e.g., an RNN, to generate an embedding of the set of molecule fragments included in the training molecule. The system can process the embedding using the decoder subnetwork, e.g., an autoregressive language model such as an RNN or Transformer neural network, to generate a prediction of the set of molecule fragments included in the training molecule. The system can train the autoencoder neural network to optimize an objective function that measures an error (e.g., a reconstruction error) between (i) the prediction of the set of molecule fragments included in the training molecule that has been generated using the embedding subnetwork and the decoder subnetwork and (ii) the set of molecule fragments included in the training molecule of the target output.

The system can determine gradients of the objective function with respect to current values of parameters of the autoencoder neural network, e.g., using backpropagation. The system can then update the current values of the parameters of the autoencoder neural network using the gradients, e.g., by the update rule of an appropriate gradient descent optimization algorithm, e.g., RMSprop or Adam.

Figure 12A:
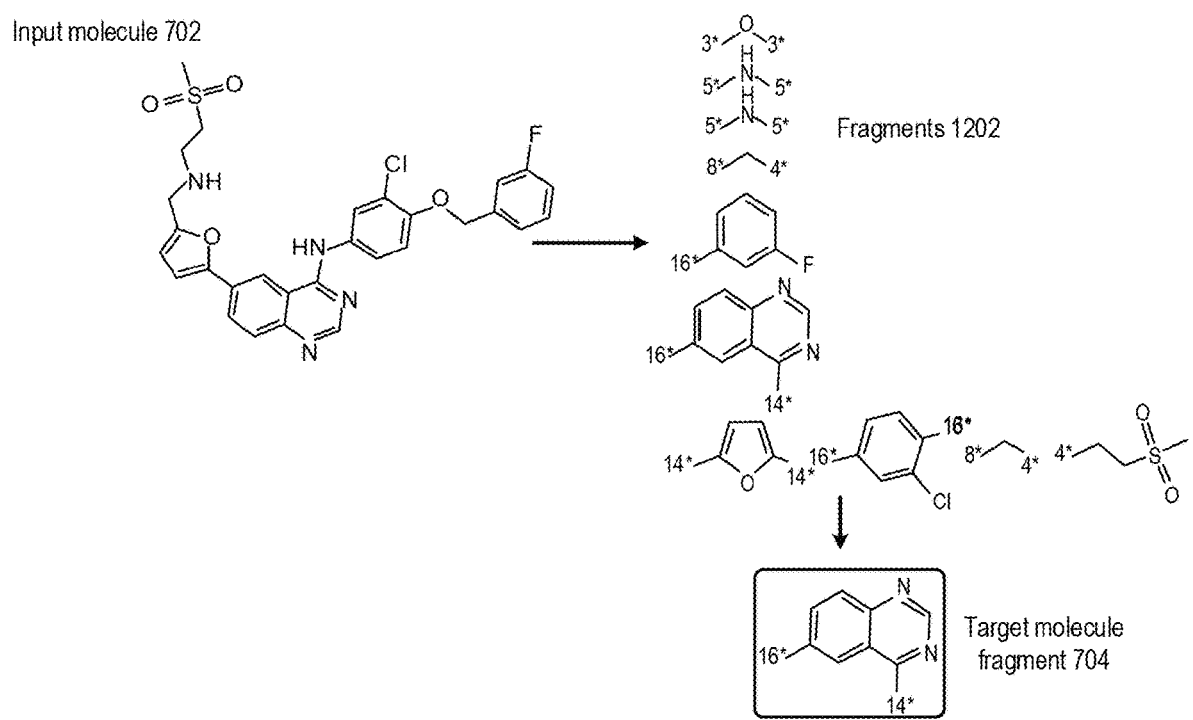
FIGS. 12A-12C show an example input molecule and an example set of alternative molecule fragments.

FIG. 12A shows an example input molecule 702. FIG. 12A also shows an example target molecule fragment 704. In the example of FIG. 12A, the target molecule fragment 704 is selected from fragments 1202 of the input molecule 702. The fragments 1202 can each include an atom, a group of atoms, or a functional group of the input molecule 702. In some cases, multiple fragments include the same atom, group of atoms, or functional groups of the input molecule 702.

Figure 12B:
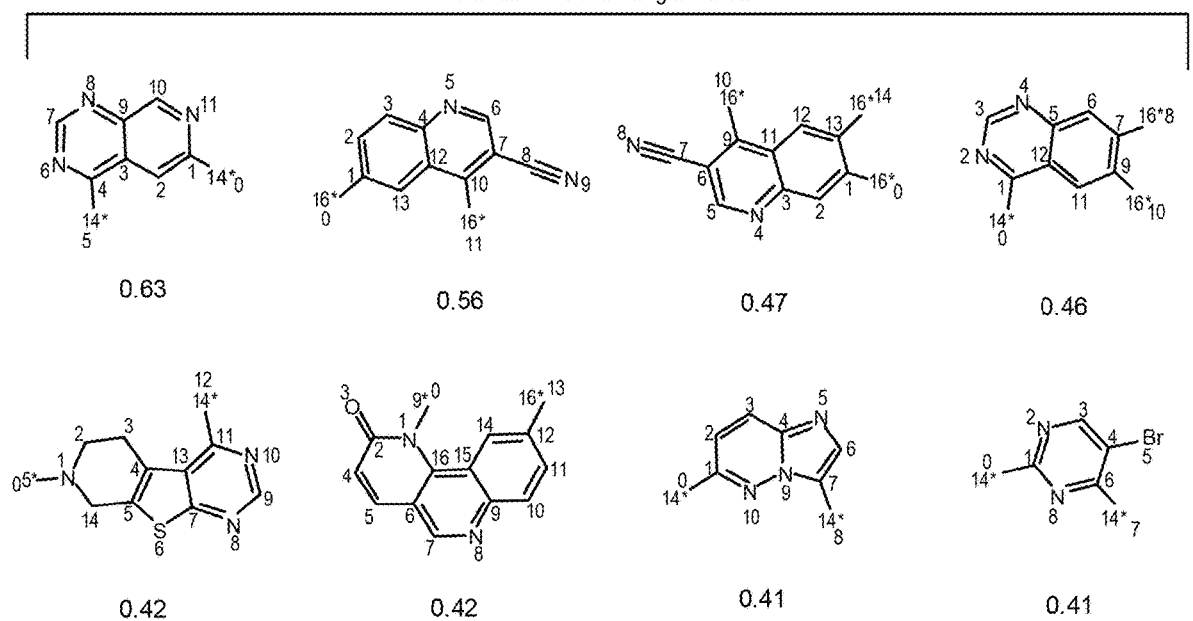
Figure 12C:
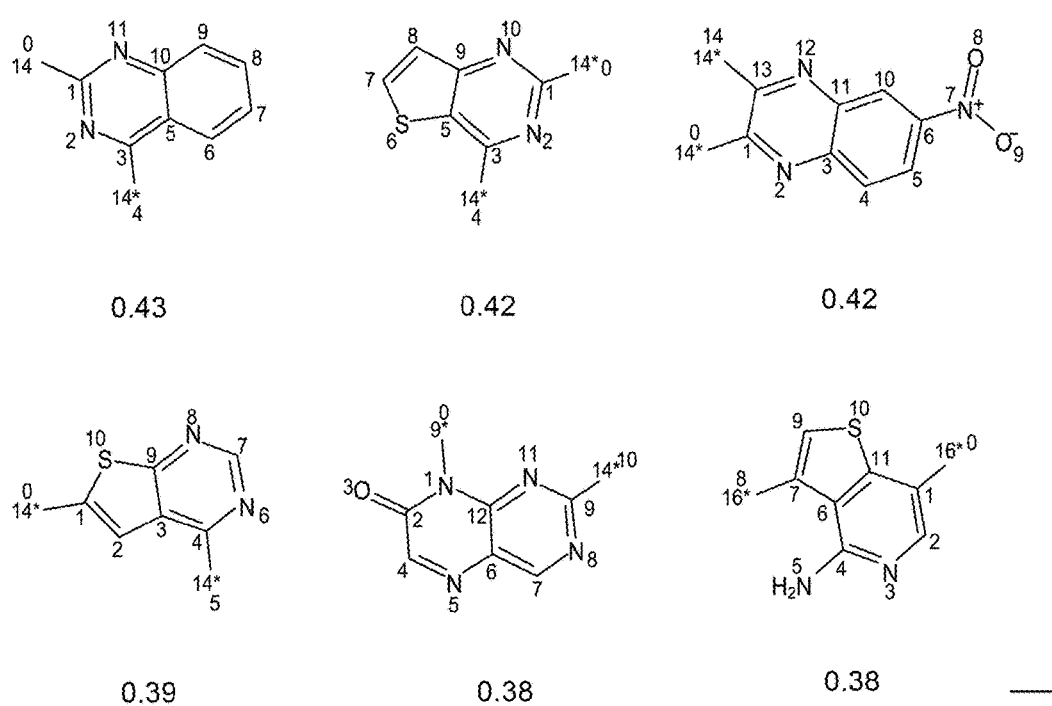

FIGS. 12B-12C show an example set of alternative molecule fragments 722. For example, the system can generate the set of alternative molecule fragments 722 for the target molecule fragment 704 as described above with reference to FIG. 7.

Figure 13A:
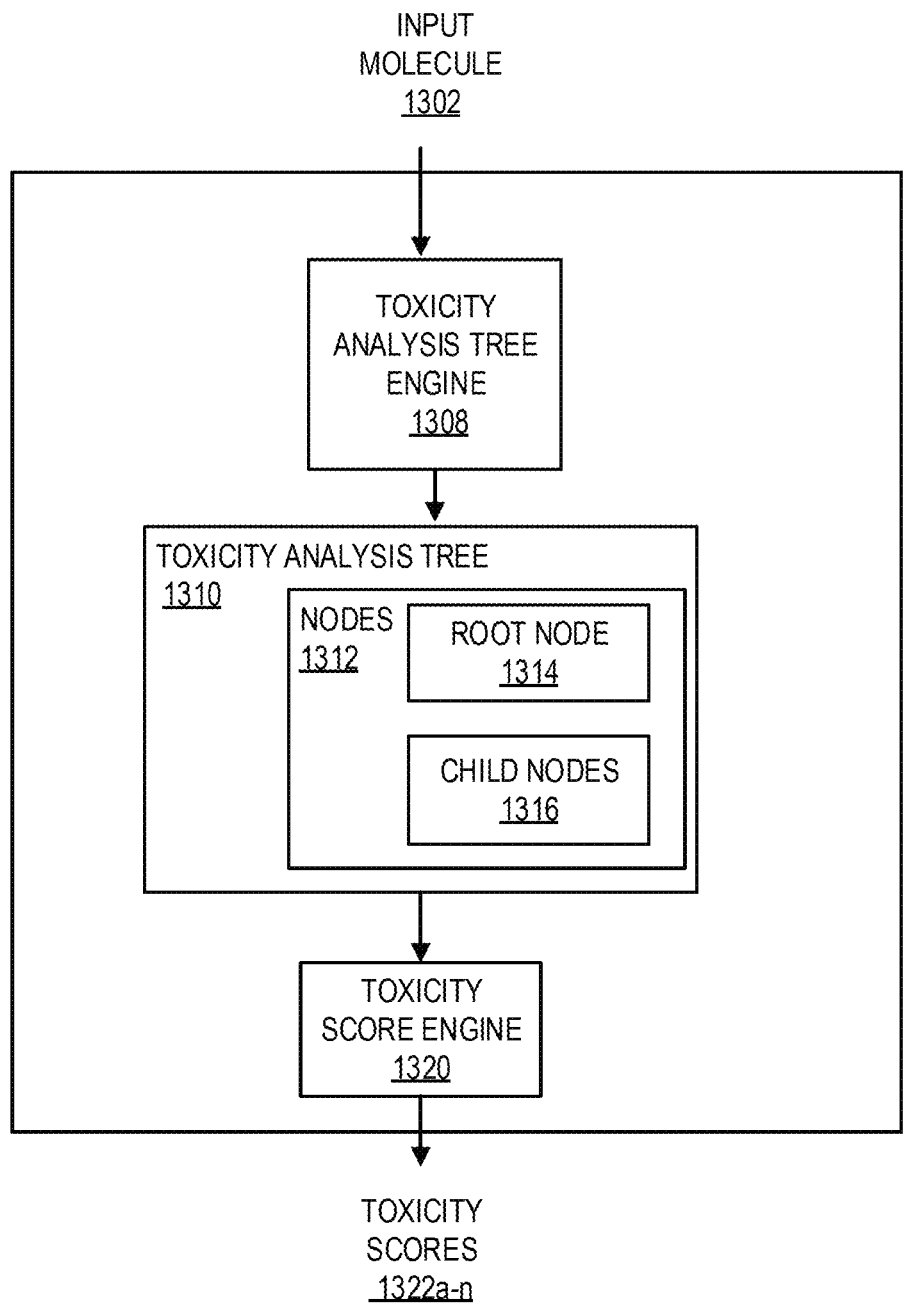
FIG. 13A shows an example toxicity analysis system.

FIG. 13A shows an example toxicity analysis system 1300. The toxicity analysis system 1300 is an example of a system implemented as computer programs on one or more computers in one or more locations in which the systems, components, and techniques described below are implemented.

In some implementations, the toxicity analysis system 1300 can be part of the toxicity prediction system 100 described above with reference to FIG. 1A or the molecule modification system 700 described above with reference to FIG. 7. In some implementations, the toxicity analysis system 1300, the molecule modification system 700, and/or the toxicity prediction system 100 can be subsystems of another system. In some implementations, the toxicity analysis system 1300, the molecule modification system 700, and/or the toxicity prediction system 100 can share one or more components, such as the toxicity prediction machine learning model 120 described with reference to FIG. 1A.

The toxicity analysis system 1300 is configured to generate toxicity scores 1322a-n for each of multiple molecule fragments in an input molecule 1302. Each molecule fragment can include, e.g., an atom, a group of atoms, or a functional group, in the input molecule 1302. For example, as described below, the toxicity analysis system 1300 can generate the toxicity score for each of multiple molecule fragments in the input molecule 1302 by processing a toxicity analysis tree 1310.

To generate the toxicity scores 1322a-n, the system 1300 obtains data identifying the input molecule 1302. The data identifying the input molecule 1302 can include any appropriate data identifying the molecule. For example, the data identifying the input molecule 1302 can include a textual representation of the molecule, e.g., a SMILES string identifying the molecule, or an International Chemical Identifier (InCHI). In some examples where the input molecule 1302 is a protein, the data identifying the input molecule 1302 can include data defining an amino acid sequence of the protein. In some examples where the input molecule 1302 is a nucleic acid, the data identifying the input molecule 1302 can include data defining a nucleic acid sequence of the nucleic acid.

The toxicity analysis system 1300 can obtain the data identifying the input molecule 1302 from any appropriate source, e.g., from a user or from another system, by way of an appropriate interface, e.g., an application programming interface (API) or a user interface (e.g., a graphical user interface). As an example, the other system can be an upstream system that generates data identifying molecules, e.g., in a drug discovery workflow.

The system 1300 includes a toxicity analysis tree engine 1308. The toxicity analysis tree engine 1308 generates data defining a toxicity analysis tree 1310 for the input molecule 1302.

The toxicity analysis tree 1310 includes multiple nodes 1312. The nodes 1312 include a root node 1314, parent nodes, and child nodes 1316. The toxicity analysis tree 1310 defines a hierarchy of parent-child relationships starting from the root node 1314. For example, some nodes are parent nodes that each have one or more child nodes in child nodes 1316. In some cases, a parent node of a child node can be the child node of another parent node. Some nodes are leaf nodes that do not have any child nodes. Each node is connected to one or more other nodes by a respective edge. In particular, each node represents a respective molecule and is associated with data defining a toxicity prediction for the molecule represented by the node. The toxicity prediction represents a prediction of a measure of toxicity when exposing cells to the molecule.

Figure 17:
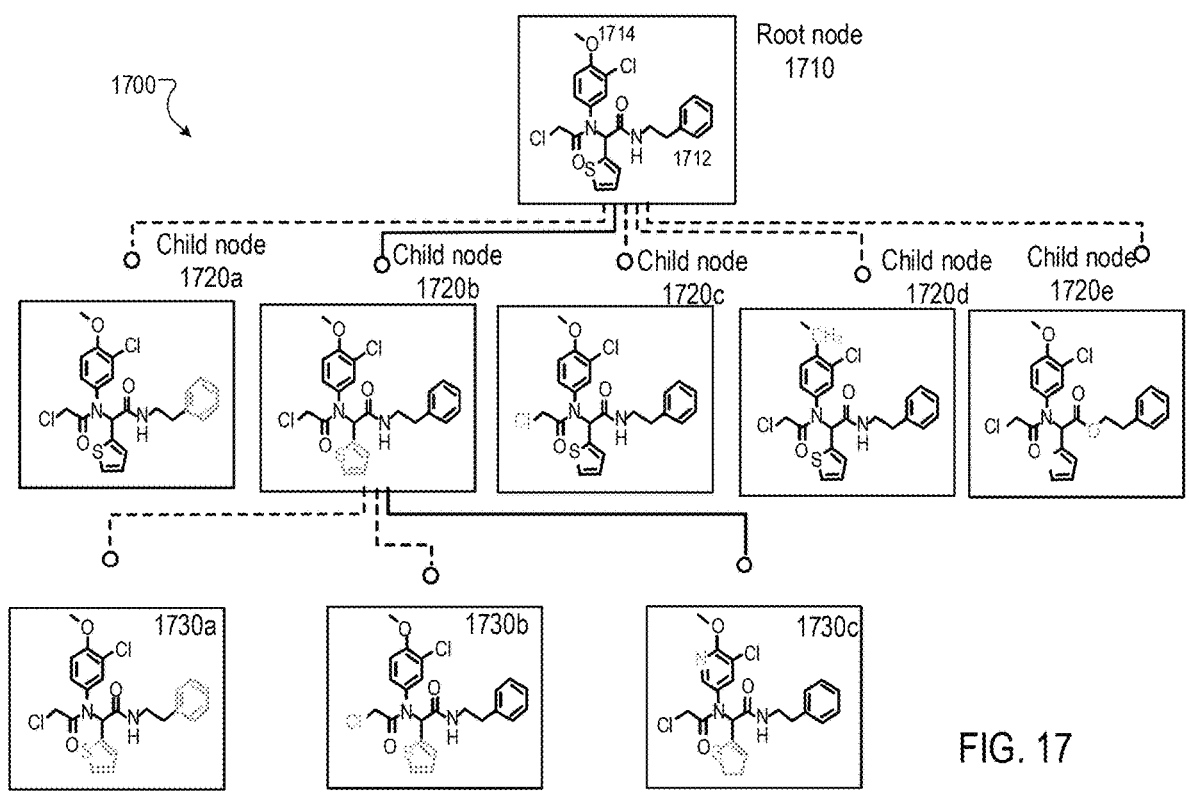
FIG. 17 is an illustration of an example toxicity analysis tree.

In the toxicity analysis tree 1310, the root node 1314 represents the input molecule 1302. Each child node of the child nodes 1316 represents a child molecule that is generated by modifying a parent molecule represented by a parent node of the child node. An example toxicity analysis tree is shown in FIG. 17. Generating the toxicity analysis tree 1310 is described in further detail below with reference to FIG. 14B and FIG. 15.

The toxicity analysis system 1300 includes a toxicity score engine 1320. The toxicity score engine 1320 processes the toxicity analysis tree 1310 to generate the toxicity scores 1322a-n. Each of the toxicity scores 1322a-n characterizes an impact of a molecule fragment in the input molecule 1302 on a toxicity of the input molecule 1302. For example, a higher toxicity score can indicate a higher impact of the molecule fragment on increasing the toxicity of the input molecule 1302. A lower toxicity score can indicate a lower impact of the molecule fragment on increasing the toxicity of the input molecule 1302.

After generating the toxicity scores 1322a-n, the toxicity analysis system 1300 can determine a modified molecule having a lower predicted toxicity than the input molecule 1302 by modifying the input molecule 1302 based at least in part on the toxicity scores 1322a-n for the plurality of molecule fragments in the input molecule 1302.

For example, the system 1300 can identify one or more molecule fragments in the input molecule 1302 that have a respective toxicity score that indicates toxicity. For example, a toxicity score that indicates toxicity can exceed a toxicity threshold. As another example, the system 1300 can rank the molecule fragments, e.g., in order of decreasing toxicity scores. The system 1300 can identify the one or more molecule fragments as having the one or more highest-ranked toxicity scores.

The system 1300 can remove or replace the one or more identified molecule fragments from the input molecule 1302 to determine the modified molecule. For example, for each of the one or more identified molecule fragments, the system 1300 can process data identifying the identified molecule fragment and data identifying the input molecule 1302 using a molecule modification system, e.g., the molecule modification system 700 of FIG. 7, to generate data defining candidate modified molecules for the input molecule 1302. The system 1300 can select the modified molecule from the candidate modified molecules for the input molecule 1302.

In some examples, the system 1300 can select the modified molecule based on the predicted toxicity for each of the candidate modified molecules. For example, the system can process data identifying each of the candidate modified molecules using a toxicity prediction system, e.g., the toxicity prediction system 100 of FIG. 1A, to generate the predicted toxicity for each candidate modified molecule. The system can rank the candidate modified molecules based on the predicted toxicities.

In some examples, the system can select a subset of one or more candidate modified molecules, e.g., less than 50%, less than 10%, or less than 1%, of the candidate modified molecules for further processing, e.g., for inclusion in a drug, for physical synthesis, or further computational analysis, from the candidate modified molecules based on the ranking. For example, the system can select the one or more modified molecules that have the lowest toxicity in the ranking.

In some examples, the system 1300 can perform a physical experiment to measure an experimental toxicity of the modified molecule.

Further computational analysis can include, e.g., predicting the binding affinity for a binding site, e.g., using molecular docking or molecular dynamics simulations. Further computational analysis can be computationally intensive, and performing further computational analysis of all of the candidate modified molecules may be computationally infeasible. By selecting one or more modified molecules based on the ranking, the system performs further processing only on the selected candidate modified molecules that are predicted to have lower toxicity. The system can thus filter the candidate modified molecules to prioritize the selected candidate modified molecules for further processing, reducing the consumption of computational resources, e.g., memory and computing power, otherwise required to perform further processing for a larger number or all of the candidate modified molecules.

In some implementations, the toxicity analysis system 1300 can output the toxicity scores 1322*a-n*. For example, the toxicity analysis system 1300 can present a visual representation of the toxicity scores 1322*a-n* for the molecule fragments in the input molecule 1302 on a display of a user device. The visual representation can include, for example, a two-dimensional (2D) representation of a chemical structure of the input molecule 1302. Each of multiple molecule fragments in the input molecule 1302 are overlaid with a color having an intensity that represents a toxicity score for the molecule fragment. An example visual representation is described below with reference to FIG. 13B. Thus the system 1300 can present a visual representation that shows which molecule fragments are likely to contribute to the toxicity of the input molecule 1302, and which fragments, upon being removed or replaced, can reduce the toxicity of the molecule.

As another example, the toxicity analysis system 1300 can store the toxicity scores 1322*a-n* in a memory. As another example, the toxicity analysis system 1300 can transmit the toxicity scores 1322*a-n* over a data communication network. As another example, the toxicity analysis system 1300 can provide the toxicity scores 1322*a-n* to a system that performs downstream processing based on the toxicity scores 1322*a-n*.

Figure 13B:
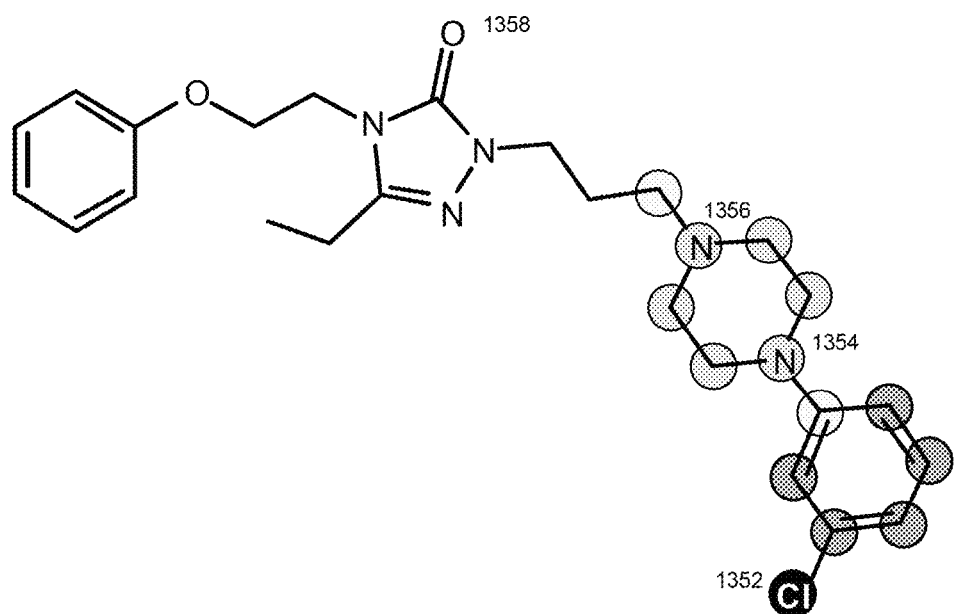
FIG. 13B shows an example visual representation of a chemical structure of an input molecule.

FIG. 13B shows an example visual representation 1350 of a chemical structure of the input molecule 1302. The visual representation 1350 shows the atoms and bonds of the input molecule 1302, with some atoms, e.g., the Cl atom 1352 and the N atoms 1354 and 1356, overlaid with different colors. A molecule fragment, e.g., the Cl atom 1352, overlaid with a higher intensity color can represent a higher toxicity score for the molecule fragment, compared to a molecule fragment, e.g., the N atoms 1354 and 1356, overlaid with a lower intensity color, or compared to molecule fragments, e.g., the O atom 1358, that are not overlaid with any color.

Figure 14A:
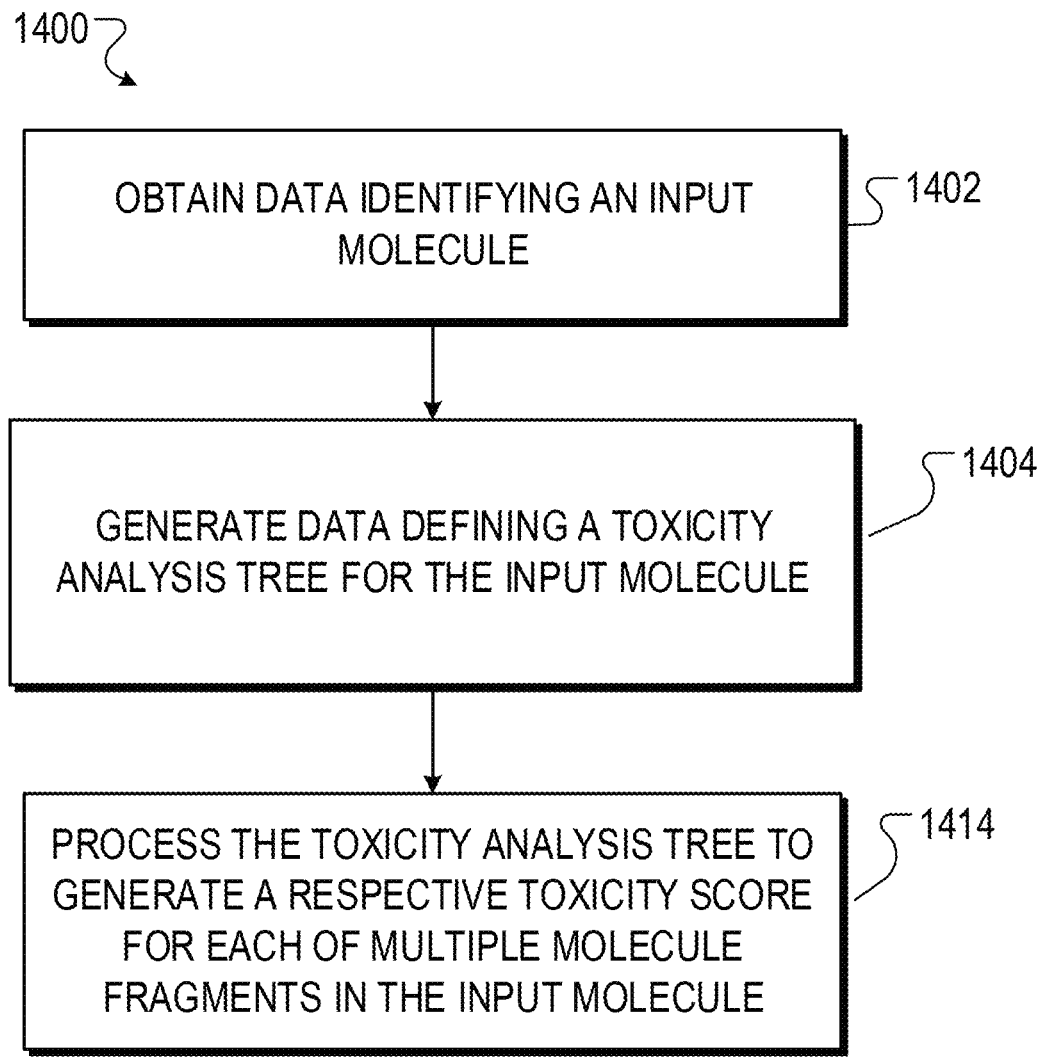
FIG. 14A is a flow diagram of an example process 1400 for generating toxicity scores for each of multiple molecule fragments in an input molecule.

FIG. 14A is a flow diagram of an example process 1400 for generating toxicity scores for each of multiple molecule fragments in an input molecule. For convenience, the process 1400 will be described as being performed by a system of one or more computers located in one or more locations. For example, a molecule modification system, e.g., the toxicity analysis system 1300 of FIG. 13A, appropriately programmed in accordance with this specification, can perform the process 1400.

The system obtains data identifying an input molecule (step 1402). In some examples, the system can obtain the data identifying the input molecule and the data identifying the target molecule fragment from any appropriate source, e.g., from a user or from an upstream system that generates data identifying an input molecule, e.g., in a drug discovery workflow. The system can obtain the data identifying the input molecule by way of an appropriate interface, e.g., an application programming interface (API) or a user interface (e.g., a graphical user interface).

The system generates data defining a toxicity analysis tree for the input molecule (step 1404). The system can initialize the toxicity analysis tree to include a root node representing the input molecule. The system can generate the data defining the toxicity prediction for the input molecule using a toxicity prediction machine learning model, e.g., the toxicity prediction machine learning model 120 of FIG. 1A.

The system can iteratively expand the toxicity analysis tree over multiple iterations. Expanding the toxicity analysis tree at each iteration is described in further detail below with reference to FIG. 14B.

In some examples, the system can iteratively expand the toxicity analysis tree over the multiple iterations to encourage an increase in toxicity predictions of molecules represented by nodes in the toxicity analysis tree. As an example, as described below with reference to FIG. 15, the system can select nodes for expansion that represent molecules that have higher toxicity predictions.

The system processes the toxicity analysis tree to generate a respective toxicity score for each of multiple molecule fragments in the input molecule (step 1416). The respective toxicity score for each molecule fragment characterizes an impact of the molecule fragment on a toxicity of the input molecule. The system can generate toxicity scores for different levels of granularity of molecule fragments in the input molecule. For example, the system can generate toxicity scores for atoms, groups of atoms, and functional groups. Generating a toxicity score for a molecule fragment is described below with reference to FIG. 16.

Figure 14B:
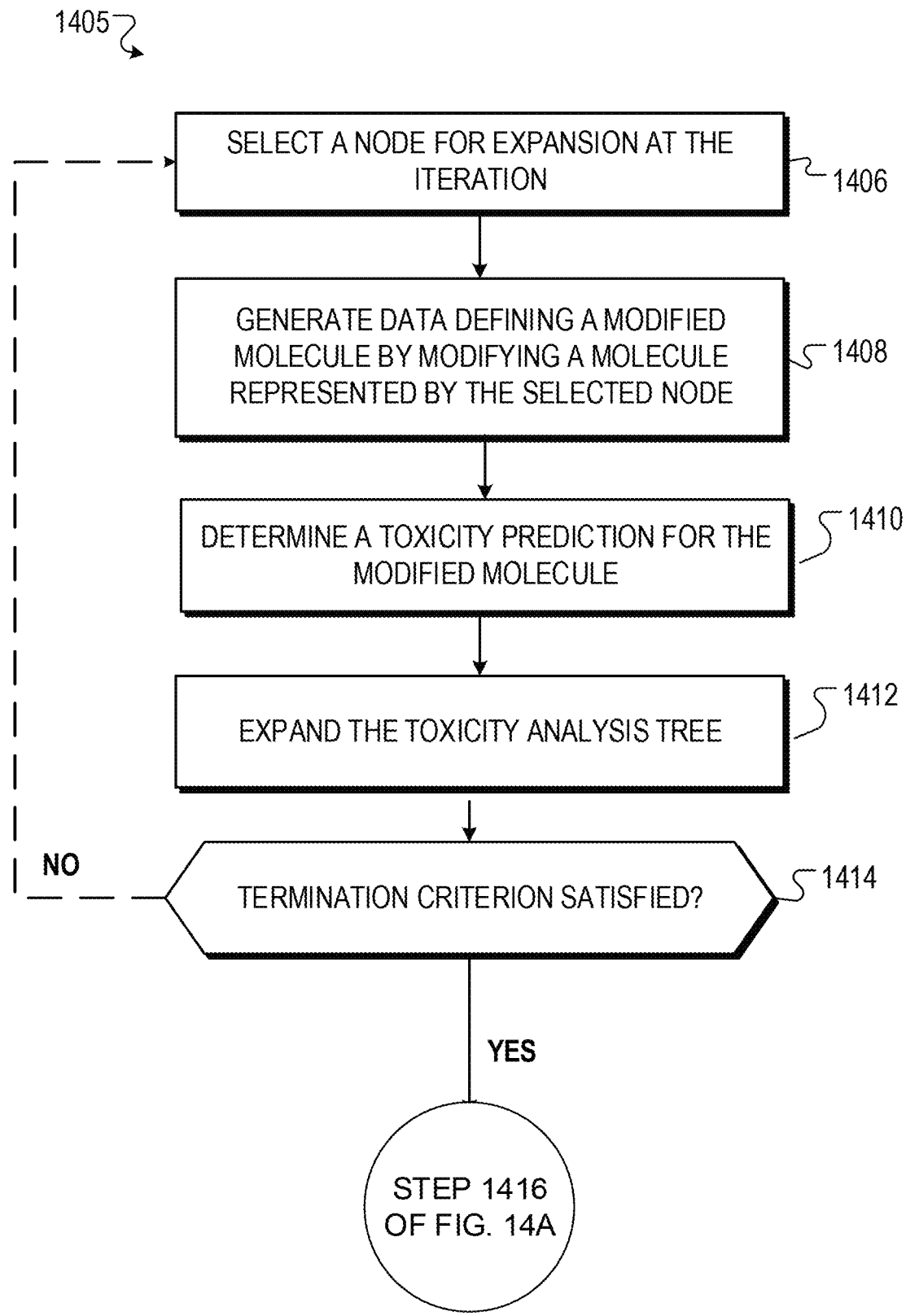
FIG. 14B is a flow diagram of an example process for expanding a toxicity tree.

FIG. 14B is a flow diagram of an example process 1405 for expanding a toxicity tree. For convenience, the process 1405 will be described as being performed by a system of one or more computers located in one or more locations. For example, a molecule modification system, e.g., the toxicity analysis system 1300 of FIG. 13, appropriately programmed in accordance with this specification, can perform the process 1405.

The system can perform the process 1405 as part of step 1404 of FIG. 14A. The system can perform the process 1405 to expand the toxicity tree at each of the one or more iterations.

The system selects a node for expansion at the iteration (step 1406). At the first iteration, the system selects the root node for expansion.

At subsequent iterations, the system can select the node for expansion based at least in part on the toxicity predictions for the nodes in the toxicity analysis tree. As a particular example, the system can select the node in the toxicity analysis tree to expand at the iteration using a Monte Carlo Tree Search (MCTS) optimization algorithm. Selecting a node for expansion at the iteration is described in further detail below with reference to FIG. 15.

The system generates data defining a modified molecule by modifying a molecule represented by the selected node (step 1408). For example, the system can modify the molecule represented by the selected node by removing or replacing a molecule fragment, e.g., an atom, a group of atoms, or a functional group, of the molecule.

In some examples, the system can identify multiple molecule fragments included in the molecule using retrosynthetic fragmentation, e.g., using the Breaking of Retrosynthetically Interesting Chemical Substructures (BRICS) algorithm. In some examples, the system can fragment the molecule using functional group-based fragmentation, e.g., using a pattern matching algorithm, or graph-based fragmentation, e.g., using the Bron-Kerbosch algorithm.

In some examples, the system can remove a molecule fragment from the molecule represented by the selected node. For example, referring to FIG. 17, the system can generate data defining the modified molecule represented by node 1720a by removing the benzene molecule fragment 1712 depicted on the right side of the molecule represented by the selected node 1710.

In some examples, the system can remove the subsequence of the textual representation of the molecule represented by the selected node that corresponds to the molecule fragment to be removed, to generate a textual representation of the modified molecule.

In some examples, the system can randomly select a molecule fragment from multiple molecule fragments included in the molecule for removal.

In some other examples, the system can replace a molecule fragment from the molecule represented by the selected node with a new molecule fragment. For example, referring to FIG. 17, the system can generate data defining the modified molecule represented by node 1720d by replacing the O molecule fragment 1714 depicted on the top of the molecule represented by the selected node 1710 with a $CH_2$ molecule fragment 1724.

In some examples, the system can replace the subsequence of the textual representation of the molecule represented by the selected node that corresponds to the molecule fragment to be replaced, with a textual representation of the new molecule fragment, to generate a textual representation of the modified molecule.

In some examples, the system can randomly select a molecule fragment from multiple molecule fragments included in the molecule, e.g., identified by fragmenting the molecule as described above, for replacement.

In some examples, the system can select the new molecule fragment from a database of candidate molecule fragments according to predefined rules. For example, the system can select the new molecule fragment to have the same number of atoms, or a smaller number of atoms, than the molecule fragment selected to be replaced.

In some examples, the system can select the new molecule fragment from a set of alternative molecule fragments using the molecule modification system 700 described above with reference to FIG. 7. For example, the system can determine, for each candidate molecule fragment in a database of candidate molecule fragments, a respective similarity measure between: (i) an embedding of a molecule fragment of the molecule, and (ii) an embedding of the candidate molecule fragment. The system can select multiple candidate molecule fragments from the database of candidate molecule fragments for inclusion in the set of alternative molecule fragments based on the similarity measures. The system can replace the molecule fragment from the molecule represented by the selected node with a new molecule fragment selected from the set of alternative molecule fragments.

The system determines a toxicity prediction for the modified molecule (step 1410). In some implementations, the system can determine the toxicity prediction for the modified molecule by processing a model input that characterizes the modified molecule and a predefined dose value using a toxicity prediction machine learning model to generate a model output that defines the toxicity prediction for the modified molecule.

An example toxicity prediction machine learning model is described above with reference to FIG. 1A. As a particular example, the toxicity prediction machine learning model can include a decision tree ensemble.

In some examples, for each of multiple predefined dose values, the system can provide data identifying the modified molecule to a toxicity prediction system, e.g., the toxicity prediction system 100 of FIG. 1A, to generate a toxicity dose-response curve for the modified molecule. In these examples, the system can generate a summarized toxicity prediction for each modified molecule. For example, for each modified molecule, the system can derive a statistic summarizing the toxicity dose-response curve, e.g., the area under the curve.

The system expands the toxicity analysis tree (step 1412). For example, the system can expand the toxicity analysis tree by: (i) adding a new node representing the modified molecule to the toxicity analysis tree as a child node of the selected node, and (ii) associating the new node with the toxicity prediction for the modified molecule.

In some examples, the system can expand the toxicity analysis tree at each of one or more iterations by adding multiple new child nodes to a node in the toxicity analysis tree that is selected for expansion at the iteration. Each new child node represents a respective modified molecule that is generated by applying a respective modification operation from a set of possible modification operations to a molecule represented by the node that is selected for expansion at the iteration. The modification operations can include, for example, removing a molecule fragment from the molecule represented by the node that is selected for expansion at the iteration, or replacing a molecule fragment from the molecule represented by the node that is selected for expansion at the iteration with a new molecule fragment.

The system can perform the steps 1406-1412 at the iteration until a termination criterion is satisfied. For example, the system can determine whether the termination criterion is satisfied at the iteration (step 1414). For example, the system can determine that the termination criterion is satisfied if the toxicity analysis tree has reached a maximum depth, or if the toxicity analysis tree has reached a maximum number of nodes.

If the system determines that the termination criterion is not satisfied, the system can return to step 1406 to expand the tree at a next iteration.

If the system determines that the termination criterion is satisfied, the system can proceed to perform step 1416 of FIG. 14A.

Figure 15:
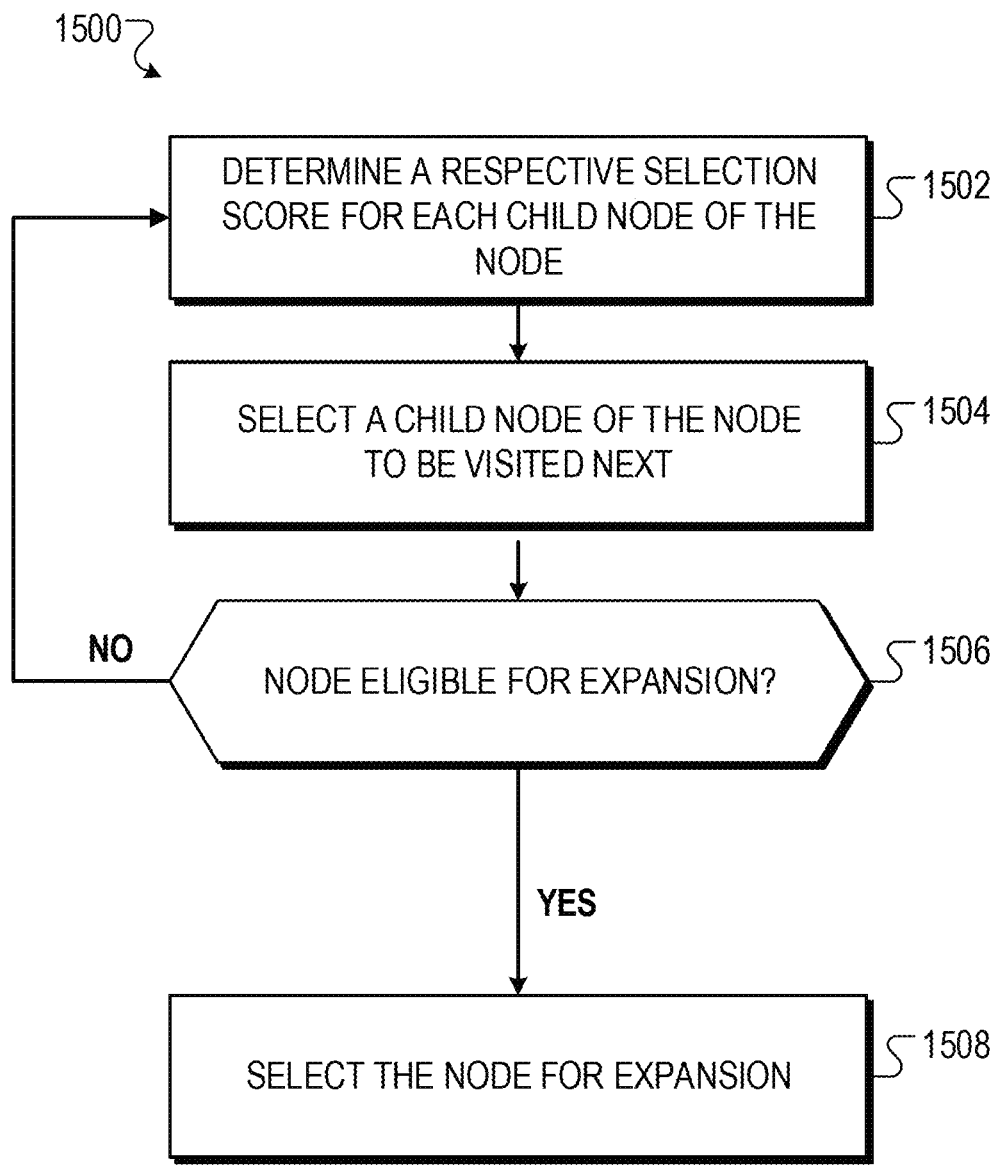
FIG. 15 is a flow diagram of an example process for selecting a node in a toxicity analysis tree to expand at an iteration.

FIG. 15 is a flow diagram of an example process 1500 for selecting a node in a toxicity analysis tree to expand at an iteration. For convenience, the process 1500 will be described as being performed by a system of one or more computers located in one or more locations. For example, a molecule modification system, e.g., the toxicity analysis system 1300 of FIG. 13A, appropriately programmed in accordance with this specification, can perform the process 1500.

The system can sequentially traverse nodes in the toxicity analysis tree, starting from the root node, until a node that is eligible for expansion is reached. The system can perform the steps 1502-1504 at each node before the node that is eligible for expansion is reached.

The system determines a respective selection score for each child node of the node (step 1502). For example, the system can determine the respective selection score based at least in part on: (i) a toxicity prediction for a molecule represented by the child node, (ii) toxicity predictions for any subtree of the toxicity analysis tree that is rooted at the child node, and (iii) a number of previous visits to the child node. For example, the system can determine a higher selection score for a higher toxicity prediction for the molecule represented by the child node, a higher average toxicity prediction for the subtrees rooted at the child node, and a higher number of previous visits to the child node.

In some examples, the system can determine the respective selection score for the child node further based on a number of previous visits to the node. As a particular example, the system can determine the respective selection score as the sum of a first value based on the toxicity prediction for the molecule represented by the child node, and a second value based on the toxicity predictions for any subtrees that are rooted at the child node. The system can determine the first value as the product of a constant value, the toxicity score for the child node, and the square root of the number of previous visits to the node, divided by the sum of a second constant value and the number of visits to the child node. The system can determine the second value as the sum of the toxicity predictions for any leaf nodes (e.g., nodes without child nodes) for any subtrees rooted at the child node, divided by the number of visits to the child node.

The system selects a child node of the node to be visited next in the sequential traversal of the nodes in the toxicity analysis tree (step 1504). For example, the system can select the child node of the node to be visited next based on the selection scores for the child nodes. As an example, the system can select the child node of the node that has a highest selection score to be visited next.

The system determines whether the node is eligible for expansion (step 1506). For example, the system can determine that the node is eligible for expansion if the node has one or more child nodes that have no previous visits. As another example, the system can determine that the node is eligible for expansion if the node is at less than a predefined maximum depth in the toxicity analysis tree, if the node has fewer than a threshold number of child nodes, if the molecule represented by the node includes at least a minimum number of atoms, etc.

If the system determines that the node is not eligible for expansion, the system can return to step 1502 for the next node in the sequential traversal.

If the system determines that the node is eligible for expansion, the system selects the node for expansion (step 1508). In some examples, the system proceeds to perform steps 1408-1412 for the selected node. In some examples, the system adds multiple new child nodes to the selected node, where each new child node represents a respective modified molecule that is generated by applying a respective modification operation from a set of possible modification operations to the molecule represented by the selected node.

Figure 16:
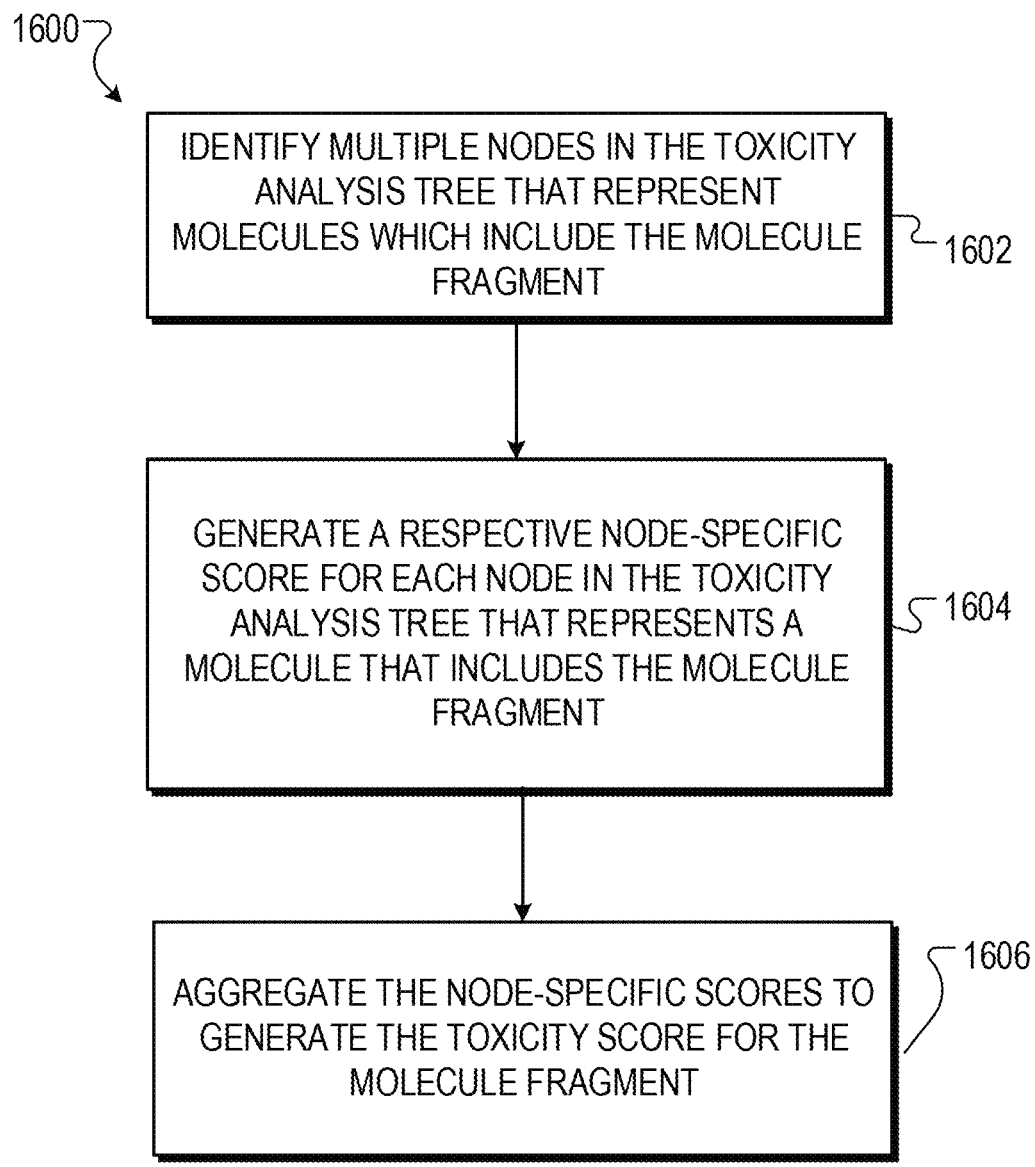
FIG. 16 is a flow diagram of an example process for generating a toxicity score for the molecule fragment.

FIG. 16 is a flow diagram of an example process 1600 for generating a toxicity score for the molecule fragment. For convenience, the process 1600 will be described as being performed by a system of one or more computers located in one or more locations. For example, a molecule modification system, e.g., the toxicity analysis system 1300 of FIG. 13A, appropriately programmed in accordance with this specification, can perform the process 1600.

The system identifies multiple nodes in the toxicity analysis tree that represent molecules which include the molecule fragment (step 1602).

The system generates a respective node-specific score for each node in the toxicity analysis tree that represents a molecule that includes the molecule fragment (step 1604). For example, the system can determine the node-specific score based at least in part on: (i) the toxicity prediction for the molecule represented by the node, and (ii) a size of the molecule represented by the node relative to a size of the input molecule. For example, the system can determine a higher node-specific score for a molecule fragment that has a smaller size, or a higher node-specific score for a molecule fragment that is included in a molecule that has a higher toxicity. As a particular example, the system can determine the node-specific score as an average, over each node that includes the molecule fragment, of the number of molecules in the input molecule, divided by the number of atoms in the molecule represented by the node, raised to a value based on the toxicity prediction for the molecule represented by the node. The system can determine the value to be the inverse of the sum of the toxicity prediction and a constant, subtracted by 1. The constant can be a small positive number, e.g., 0.001.

The system aggregates the node-specific scores to generate the toxicity score for the molecule fragment (step 1606). For example, the system can determine the toxicity score for the molecule fragment based on a measure of central tendency (e.g., mean, median, or mode) of the node-specific scores.

FIG. 17 is an illustration of an example toxicity analysis tree 1700. The toxicity analysis tree 1700 includes a root node 1710. The toxicity analysis tree also includes child nodes 1720*a-e*, each generated by modifying the parent molecule represented by the parent node, the root node 1710. The toxicity analysis tree also includes child nodes 1730*a-c*, each generated by modifying the parent molecule represented by the parent node, the node 1720*b*.

FIGS. 18A-18B show example materials and equipment for performing a physical experiment involving the exposure of cell cultures to an input molecule. A system such as the toxicity prediction system 100 of FIG. 1A can use the results of the physical experiment for generating training data to train machine learning models such as the toxicity prediction machine learning model 120 of FIG. 1A.

FIGS. 19A-19B show example recipes involved in a physical experiment involving the exposure of cell cultures to an input molecule.

Figure 20:
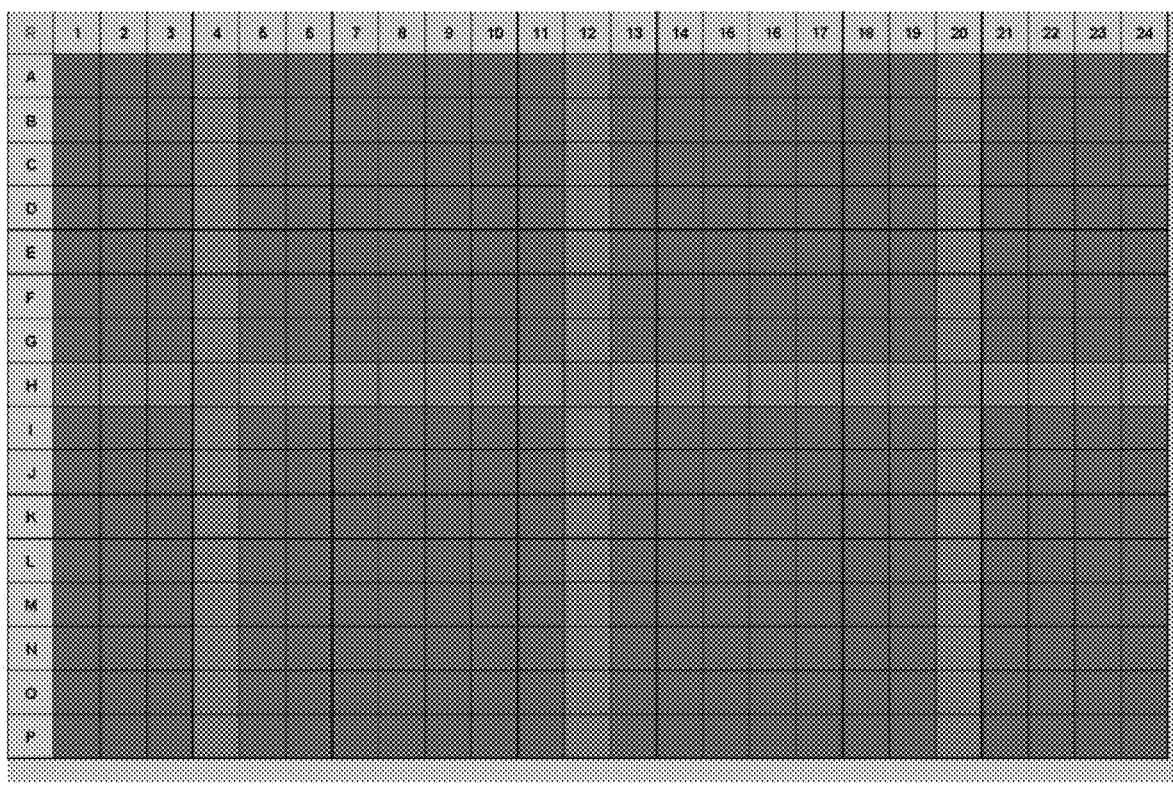
FIG. 20 shows an example compound plate, also referred to as multi-well plate, layout for a physical experiment involving the exposure of cell cultures to an input molecule.

FIG. 20 shows an example compound plate, also referred to as multi-well plate, layout for a physical experiment involving the exposure of cell cultures to an input molecule. The light gray boxes represent dimethyl sulfoxide (DMSO) wells (or neutral control wells). The dark gray boxes represent compound wells that include cell culture that has been exposed to the input molecule.

Figure 21:
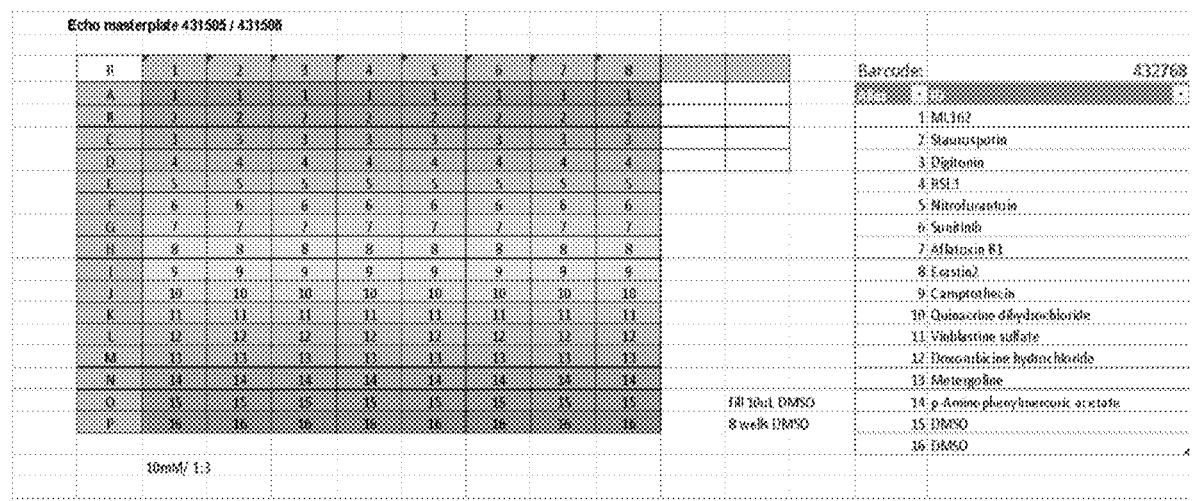
FIG. 21 shows an example reference source plate layout.

FIG. 21 shows an example reference source plate layout. For example, the reference source plate layout can be an Echo source plate layout. FIG. 21 shows 14 tool compounds and DMSO, with 8 pt/3× dilution prepared manually.

Figure 22:
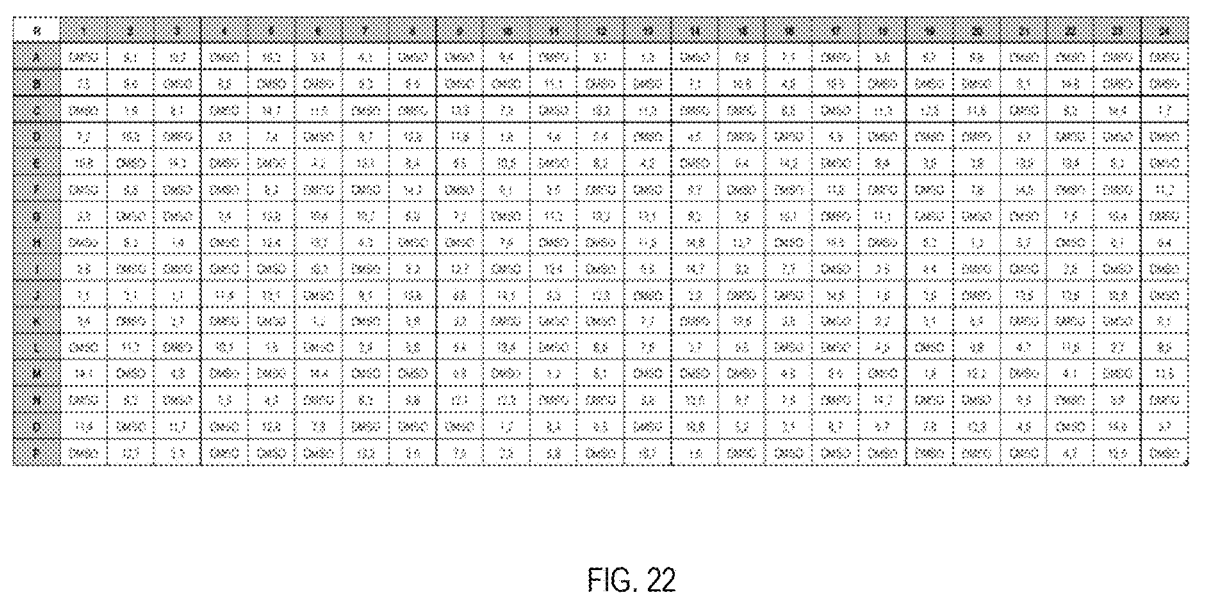

FIG. 22 shows an example reference destination plate layout. For example, the reference destination plate layout can be an Echo destination plate layout. FIG. 22 shows 14 tool compounds and DMSO. The concentrations for each tool compound, where X represents the tool compound number, are: X,1 (100 uM); X,2 (33.5 uM); X,3 (11 uM); X,4 (3.5 uM); X,5 (1 uM); X,6 (0.4108 uM); X,7 (0.1369 uM); X,8 0.0456 uM).

Figure 23:
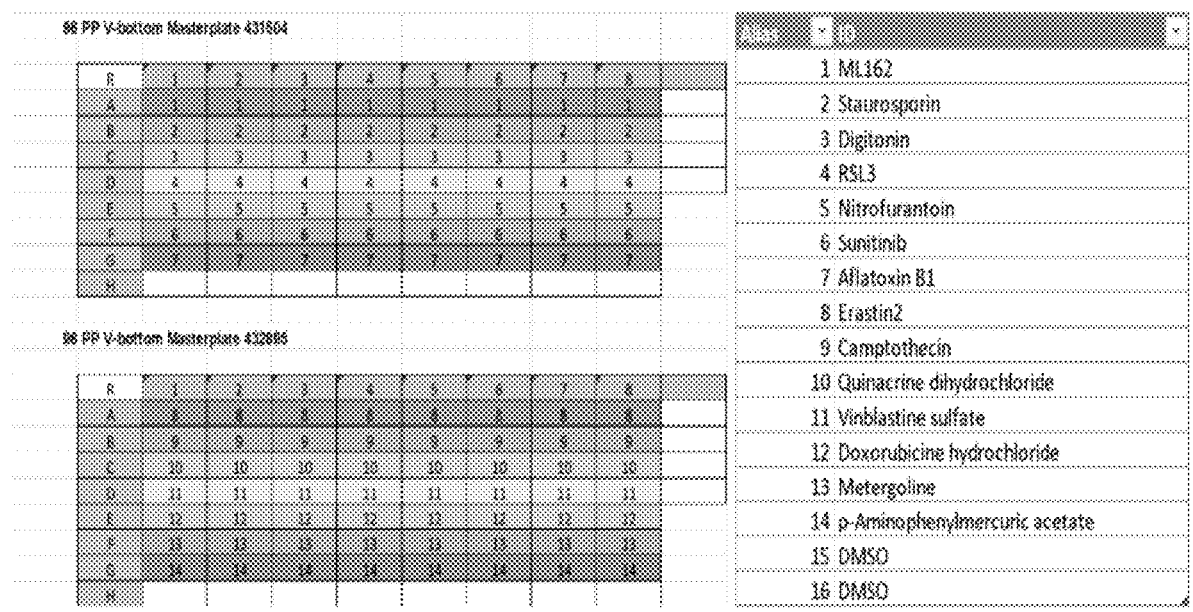
FIG. 23 shows an example 96-well master dilution plate.

FIG. 23 shows an example 96-well master dilution plate.

FIG. 24 shows example compound and DMSO volumes picked per concentration.

Figure 25:
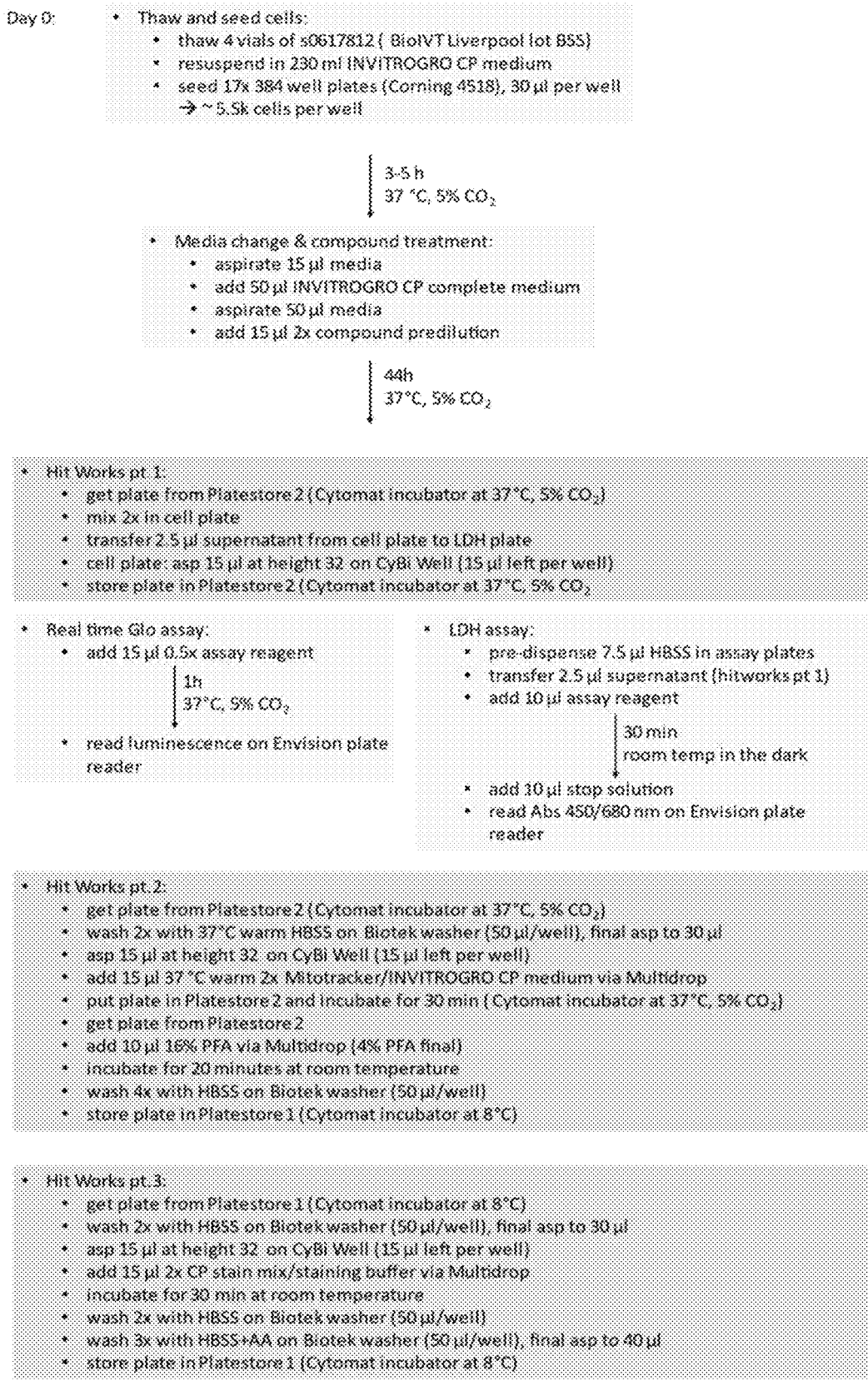
FIG. 25 shows an example process for performing a physical experiment involving the exposure of cell cultures to an input molecule.

FIG. 25 shows an example process for performing a physical experiment involving the exposure of cell cultures to an input molecule. For example, the physical experiment can include the screening process for a primary human hepatocyte (PHH) toxicity assay with multiple readouts. In brief, PHH are seeded on collagen treated 384-well imaging plates and treated with compounds 3-5 hours after seeding. Cells are incubated with compound for 44 hours. Then, LDH content is quantified in supernatants and a real time Glo assay is used to measure cell viability. After that, cells are washed and first incubated with MitoTracker live cell dye before they are fixed with PFA. Lastly, cells are stained with a mix of cell painting dyes and images are acquired on an Operetta CLS.

Compound plates are prepared. Preparing the reference compound source plate involves serial dilution of test compounds in DMSO in 384-well format using a manual multichannel pipettor. The start concentration is 10 mM; with 8 dilutions and dilution factor=3. Serially diluted compounds are stamped to ECHO 550 compatible plates to generate source plates for creating assay-ready compound plates.
1. Pick compound from Stock.
2. Add 45 µl test compound stock to Dilution Master Plate-column 1.
3. Multichannel pipettor: Preload column 2-8 with 30 uL DMSO from a DMSO reservoir
4. Multichannel pipettor: Transfer 15 µl from column 1 to column 2, discard tips, load new tips, mix 3× and proceed with next column.
5. Repeat mix-and-split (step 4) for columns 2-8
6. Centrifuge plate for 1 min at 1000 rpm (218×g)
7. Transfer 9 µl aliquot from the Dilution Master Plate is stamped to an Echo Master Plate for preparation of assay-ready compound plates using nanoliter dispensing on ECHO 550 see FIG. 20.
8. Prepare a pick file manually to define source and destination wells for ARP plate see FIG. 21.

Assay-ready compound plates are prepared. A pick job for n=1 is set up for single order with intermediates. The compound master plates are Echo-compatible 384-well MTP containing test compounds.

Part 1 DMSO Backfill:
1. Generate a new pick file for every plate concentration to fill DMSO according to FIG. 25 and to fill 500 nl DMSO in Row 8 and columns 4, 12 and 20.
2. Start Echo with a script Part 2 (Prepare Intermediate (i1) from Stock):
1. Equilibrate compound plates at room temperature for 1 hour.
2. Centrifuge plates for 1 minute at 1000 rpm (218×g).
3. Unseal the plates and put in the Echo-stacker (Platestore 1)
4. Fill Platestore 2 with destination plates containing 6 µl DMSO.
5. Start Echo with a script
6. Run Echo with Condition "meander by column".
7. Seal plates and store at 4° C. overnight.
8. Upload report file from the run.

Part 3 (Pick 5 Concentrations from Stock):
1. Equilibrate compound plates at room temperature for 1 hour.
2. Centrifuge plates for 1 minute at 1000 rpm (218×g).
3. Unseal the plates and put in the Echo-stacker (Plate store 1)
4. Fill the Plate store 2 with Destination plates.
5. Start Echo with a script
6. Run Echo with Condition as shown in FIG. 24
7. Leave row free: 8; leave column free: 4;12;20 (controls)
8. Seal plates Part 4 (Pick 3 Concentrations from i1):
1. Equilibrate compound plates (i1) at room temperature for 1 hour.
2. Centrifuge plates for 1 minute at 1000 rpm (218×g).
3. Unseal the plates and put in the Echo-stacker (Plate store 1)
4. Fill the Plate store 2 with Destination plates
5. Start Echo with a script
6. Run Echo with condition as shown in FIG. 24
7. Leave row free: 8; leave column free: 4;12;20 (controls)
8. Seal plates.

Part 5 (Reference Plate):
1. Generate random pick file to fill 500 nl CRS/DMSO according to FIG. 22; picked from FIG. 21
2. Start Echo with a script After the Run:
1. Save report files.
2. Save log files.
3. Delete log files.
4. Upload run files (only with backfill) and dispatch plates.

Collagen Coating of Cell Plates:
1. Add 50 µg/ml Collagen solution per well with Multidrop Combi Multidrop Combi settings:

| Corning low volume #4518 |
| --- |
| Standard tube cassette |
| Dispense volume: 15 µl |
| Plate: 384 well low profile (10 mm) |
| Adjust Height to 13.2 mm |
| Dispense speed: High |
| Predispense volume: 20 µl |

2. Lid plates and centrifuge for 1 minute@138×g.
3. Incubate for 1 hour @ room temperature.
4. Wash plates 2 times with sterile H2O with CyBio FeliX 384 well head, remove collagen solution with Cybio FeliX 384 well head, add 30 µl per well H2O, remove H2O, add 30 µl per well H2O, then remove H2O.

Run Felix Protocol

| Layout at CyBio-Felix |
| --- |
| Tip Tray OL3317-11-120 for protector plate |
| TipTray OL3317-11-100 with TipTray 384/60 µl |
| Reservoir Wash 2 (70% EtOH) |
| Reservoir Wash 1 (sterile H2O) |
| Reservoir with sterile Whatman-Paper |
| Destination Plate (384_4518) |
| Reservoir with sterile H2O |
| Collect Reservoir fur Waste |

5. After the last removal step air dry plates for more than 2 hours under a hood. Remove lids and place plates in a plate rack.
6. Weld in plates in a bag and store @4° C. for up to 1-2 weeks.

On Day 0, cells are thawed and seeded. PHH were thawed and plated according to vendor protocol.

Collagen Treatment of Plates:
1. Thaw Torpedo Antibody mix from −20° C. and dilute 45× in INVITROGRO CP medium to prepare Complete CP medium, store at 4° C. for later.
2. Transfer 20 ml INVITROGRO CP medium without antibiotics to a 50 ml falcon tube and 210 ml to a 250 ml Falcon tube and warm in a 37° C. water bath.
3. Pick 4 vials of BioIVT PHH 'Liverpool' 5 Donors (lot BSS) from the N2 (l) tank and immediately immerse the vials in a 37° C. water bath. Shake gently while keeping the vial immersed for ~2-3 min. When cells pull away from the vial wall transfer content into the prepared media in a Falcon tube (pour from vial).
4. Using a 5 ml stripette, add 1 ml of fresh media from the 250 ml falcon tube to the cryovial to wash any remaining cells from the vial (pipette slowly and directly into the liquid when adding back to the falcon tube).
5. Count cells at Cell Counter diluted 1:1 with Trypan Blue, 8 fields of view, size gate 8
6. Pour everything from the 50 ml Falcon tube into the 250 ml falcon tube, transfer 20 ml from the 250 ml tube to the 50 ml tube to rinse, pour back into the 250 ml tube.
7. Plate cells in 30 μl per well with Multidrop Combi: 384 well low profile (10 mm)
   Standard tube cassette
   Volume: 30 μl
   Height adjusted to 13.2 mm
   Speed: medium
8. Centrifuge plates for 1 minute @100×g.
9. Store plates in a Cytomat plate incubator at 37° C., 5% CO2.

Media Change and Compound Addition:
1. 3-5 hours after seeding, change media and add compound to all plates.
   Multidrop Combi settings:
   384 well standard
   Volume: 30 μl
   Speed: high
   Standard tube cassette
   Lid plates with a sterile lid and centrifuge for 1 min @216×g.
   Run CyBi Felix protocol
   aspirates 15 μl at height 1.5, leaves 15 μl in well, adds 50 μl Complete CP medium, aspirates 50 μl at height 1.5, leaves 15 μl in well, mixes 3 times in compound plate and adds 15 μl 2× compound to the cell plate with dispense speed 2 at height 1.5.
   Afterwards the tips are washed 3× with 10% EtOH in the wash station, then 1× with 100% DMSO in a Matrix reservoir at position 5 and then 1× with DPBS in in a Matrix reservoir at position 6.
2. Store plates in a Cytomat plate incubator at 37° C., 5% CO2 for 44 hours.

On Day 2, Real Time Glo Assay and transfer of LDH Supernatant is performed.
1. Prewarm to 37° C.: Complete CP Medium in a water bath, MT Cell viability substrate and NanoLuc® Enzyme in incubator.
2. Prepare MT-Glo Reagent according to recipes.
3. The transfer of supernatant for LDH assay and the media removal for the MT-Glo assay is combined in one Hit Works protocol.

Mixes 2× times in the cell plate, then transfers 2.5 μl from cell plate to SN plate, then removes medium from cell plate @ height 32 (leaves 15 μl in plate).
4. Add 15 μl 1× RealTime-Glo™ Reagent per well with Multidrop Combi.
   Multidrop Combi Settings:
   384 well low profile (10 mm)
   Adjust Height to 13.2 mm
   Volume: 18 μl
   Speed: Medium
   Standard tube cassette
5. Centrifuge plate @ 138×g for 1 minute.
6. Incubate lidded plate for 60 minutes @37° C.
7. Read plate on Envision.

An LDH absorbance assay is performed.
1. Dispense 7.5 μl HBSS w/o Ca2+/Mg2+ in LDH Assay Plates with a Multidrop dispenser.
   Multidrop Combi settings:
   a. 384 well standard
   b. Volume: 7.5 μl
   c. Speed: high
   d. Small tube cassette
2. Transfer 2.5 μl supernatant from cell plate to LDH assay plate (via Hit Works, see above).
3. Add 10 μl Reaction Mixture from the CyQUANT™ LDH Cytotoxicity Assay Kit to assay plate with a Multidrop.
   Multidrop Combi settings:
   a. 384 well standard profile (15 mm)
   b. Volume: 10 μl
   c. Speed: high
   d. Small tube cassette
4. Centrifuge plate at 218×g for 1 minute without lid to remove air bubbles.
5. Incubate the plate for 30 minutes at room temperature and protected from light.
6. Add 10 μl stop solution with a Multidrop.
   Multidrop Combi settings:
   a. 384 well standard profile (15 mm)
   b. Volume: 10 μl
   c. Speed: high
   d. Standard tube cassette
7. Centrifuge plate @218×g for 1 minute without lid to remove air bubbles.
8. Measure the plate on the Envision using a protocol Cell painting is performed using automated staining on Hit Works automation platform.

CyBio Scheduler Program:
1. Get plate from Platestore 2 (Cytomat incubator at 37° C., 5% CO2).
2. Wash 2× with HBSS on Biotek washer (50 μl/well), final asp to 30 μl.
3. Asp 15 μl at height 32 on CyBi Well (15 μl per well left).
4. Add 15 μl 37° C. warm 2× Mitotracker/INVITROGRO CP complete medium via Multidrop.
5. Put plate in Platestore 2 and incubate for 30 min (Cytomat incubator at 37° C., 5% CO2).
6. Get plate from Platestore 2.
7. Add 10 μl 16% PFA via Multidrop (4% PFA final).
8. Incubate for 20 minutes at room temperature.
9. Wash 4× with HBSS on Biotek washer (50 μl/well), final asp to 30 μl.

10. Store plate in Platestore 1 (Cytomat incubator at 8° C.).

CyBio Scheduler Program:
1. Get plate from Platestore 1 (Cytomat incubator at 8° C.).
2. Asp 15 µl at height 32 on CyBi Well (15 µl per well left).
3. Add 15 µl 2× CP stain mix/staining buffer via Multi-drop.
4. Incubate for 30 min at room temperature.
5. Wash 2× with HBSS on Biotek washer (50 µl/well).
6. Wash 3× with HBSS+AA on Biotek washer (50 µl/well), final asp to 40 µl.
7. Store plate in Platestore 1 (Cytomat incubator at 8° C.).

Listed below are measurement settings and parameters.

Envision (Real Time Glo Measurement):
Label:
  Aperture: 384 Plate US Luminescence aperture—In
  Distance between plate and detector: 0
  Measurement time(s): 0.1
  Glow (CT2) correction factor (%): 0
Platetype: Corning 4518

Envision (LDH Absorbance Measurement):
  Excitation light (%)=100.
  No of Flashes=10
  Measurement height=6.5
Platetype: Greiner 781095

Hit Works:
Run in CyBio Scheduler for automated measurement of plates on Operetta:
1. Get plate from Platestore 1 (Cytomat incubator at 8° C.).
2. Incubate plate for 1 hour at room temperature.
3. Measure plate on Operetta (Experiment 70129_CP_Screen).
4. Store plate in Platestore 1 (Cytomat incubator at 8° C.).

Operetta
  Plate type: 384 Corning 4518 HCl rescan V4
  Autofocus: Two Peak (Default)
  Objective: 40× Water, NA 1.1
  Opt. Mode: Non-Confocal
  Camera ROI: 2160×2160
  Binning: 1
  Measurement: max. 2 h 47 min/max. 341 GB

| Channel | Label | Ex | Em | comment |
|---|---|---|---|---|
| 1 | Brightfield | Transmission | 685-760 | |
| 2 | Hoechst 33342 | 355-385 | 430-500 | Nuclei |
| 3 | PhenoVue Fluor 488 | 460-490 | 500-550 | ER (ConA) |
| 4 | CP_Nucleic acid_512 | 460-490 | 570-650 | Nucleoli/cytoplasmic RNA |
| 5 | WGA555/Phalloidin568 | 530-560 | 570-650 | Golgi/actin (Plasma membrane |
| 6 | Mito_641 | 615-645 | 655-760 | Mitochondria (MitoTracker) |

Figure 26:
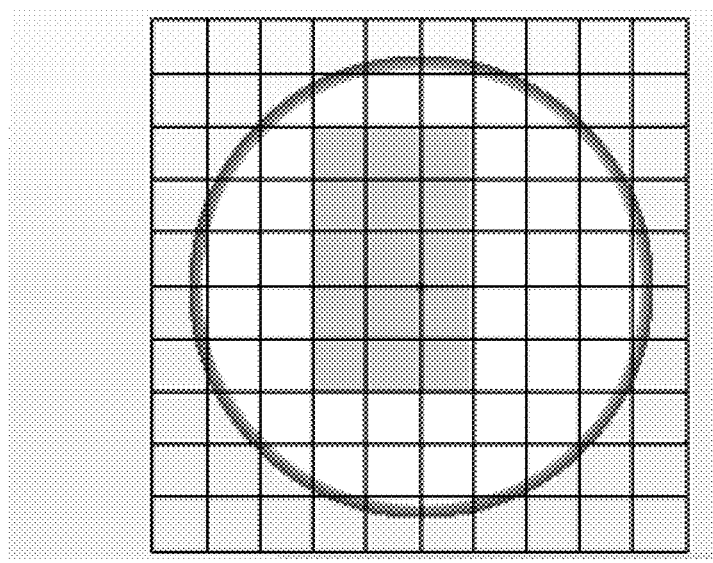
FIG. 26 shows an example FOV of a camera.

FIG. 26 shows an example FOV of a camera on a well.

Data Processing:
  Metadata and raw data files are uploaded.
  Raw data files from LDH and real time Glo measurements are uploaded.

Optimization Parameters:
  Phenoview 512 stain is used at 3 µM final concentration (6 µM in optimized cell painting protocol (Cimini, B. A., Chandrasekaran, S. N., Kost-Alimova, M. et al. Optimizing the Cell Painting assay for image-based profiling. Nat Protoc 18, 1981-2013 (2023)), they increased the concentration and decreased ConA (488 channel) concentration because some groups reported interference of the ConA with RNA signal. In this experiment a further reduction to 1 µM final conc of Phenoview was decided to minimize bleed through of Phenoview 512 signal to the WGA/Phalloidin channel.

PHH lot BSS has an unexpectedly high LDH content compared to lot INM which was used to initially validate the LDH absorbance assay. A 2× dilution in cell culture media seems not enough to significantly lower the baseline of the assay signal to a range not in danger of saturation. Dilution in HBSS instead of media and an overall increase in assay volume to 30 µl in a standard 384 well plate to allow for a 4× dilution of supernatant sample was necessary to get Abs 490-680 nm below 0.5.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Machine learning models can be implemented and deployed using a machine learning framework, e.g., a TensorFlow framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:
    obtaining data identifying: (i) an input molecule, and (ii) a target molecule fragment of the input molecule;
    generating a set of alternative molecule fragments by performing operations comprising:
        determining, for each candidate molecule fragment in a database of candidate molecule fragments, a respective similarity measure between: (i) an embedding of the target molecule fragment, and (ii) an embedding of the candidate molecule fragment;
        selecting a plurality of candidate molecule fragments from the database of candidate molecule fragments for inclusion in the set of alternative molecule fragments based on the similarity measures; and
    generating data defining a plurality of modified molecules, wherein each modified molecule is a modified version of the input molecule where the target molecule fragment is replaced by a respective alternative molecule fragment from the set of alternative molecule fragments;
    generating a respective toxicity prediction for each of the plurality of modified molecules; and
    outputting data identifying the plurality of modified molecules and the toxicity predictions for the plurality of modified molecules.

2. The method of claim 1, wherein embeddings of the candidate molecule fragments in the database of candidate molecule fragments have been generated by performing operations comprising:
    training a neural network to perform a machine learning task, wherein the neural network comprises:
        an embedding subnetwork that is configured to process data identifying a set of input molecule fragments to generate a respective embedding of each input molecule fragment; and
        a prediction subnetwork that is configured to process the embeddings of the input molecule fragments to generate a network output; and
    determining the respective embedding of each candidate molecule fragment as the embedding generated by processing the candidate molecule fragment using the embedding subnetwork of the neural network.

3. The method of claim 2, wherein the machine learning task comprises predicting an identity of a molecule fragment included in a training molecule based on identities of one or more other molecule fragments included in the training molecule.

4. The method of claim 3, wherein the machine learning task comprises predicting an identity of a molecule fragment included in a training example based on both: (i) identifies of one or more other molecule fragments included in the training molecule, and (ii) a spatial arrangement of the one or more other molecule fragments included in the training molecule.

5. The method of claim 3, wherein training the neural network to perform the machine learning task comprises:
    generating a set of training examples for training the neural network, comprising, for each training example:
        obtaining data identifying a training molecule;
        processing the data identifying the training molecule to identify a set of molecule fragments included in the training molecule;
        generating a training input for the training example, wherein the training input comprises all but one of the molecule fragments in the set of molecule fragments; and
        generating a target output for the training example, wherein the target output comprises the one molecule fragment excluded from the training input; and
    training the neural network on the set of training examples.

6. The method of claim 5, wherein training the neural network on the set of training examples comprises, for each training example:
    processing molecule fragments included in the training input of the training example using the neural network to generate a score distribution over the database of candidate molecule fragments; and
    training the neural network to optimize an objective function that measures an error between: (i) the score distribution over the database of candidate molecule fragments, and (ii) a molecule fragment specified by the target output of the training example.

7. The method of claim 6, wherein training the neural network to optimize the objective function comprises:
    backpropagating gradients of the objective function through the prediction subnetwork and into the embedding subnetwork of the neural network.

8. The method of claim 7, wherein the objective function measures the error using a cross-entropy term.

9. The method of claim 7, wherein the embedding subnetwork is parametrized by an array of embeddings that comprises a respective embedding for each candidate molecule fragment in the database of candidate molecule fragments; and
    wherein backpropagating gradients of the objective function through the prediction subnetwork and into the embedding subnetwork of the neural network comprises:
        backpropagating gradients through the array of embeddings that parametrize the embedding subnetwork of the neural network.

10. The method of claim 7, wherein the embedding subnetwork of the neural network is configured to process data characterizing a respective chemical structure of each input molecule fragment in a set of input molecule fragments using one or more embedding neural network layers; and
    wherein backpropagating gradients of the objective function through the prediction subnetwork and into the embedding subnetwork of the neural network comprises:

backpropagating gradients through the embedding neural network layers of the embedding subnetwork of the neural network.

11. The method of claim 1, wherein the database of candidate molecule fragments has been generated by fragmenting a plurality of training molecules.

12. The method of claim 1, wherein selecting a plurality of candidate molecule fragments from the database of candidate molecule fragments for inclusion in the set of alternative molecule fragments based on the similarity measures comprises:
   selecting a plurality of candidate molecular fragments with embeddings having highest similarity to the embedding of the target molecule fragment for inclusion in the set of alternative molecule fragments.

13. The method of claim 1, wherein outputting data identifying the plurality of modified molecules and the toxicity predictions for the plurality of modified molecules comprises:
   determining a ranking of the plurality of modified molecules based at least in part on the toxicity predictions for the plurality of modified molecules.

14. The method of claim 13, wherein the ranking of the plurality of modified molecule is based at least in part on one or more other properties in addition to toxicity, including one or more of: synthetic accessibility, binding affinity, or solubility.

15. The method of claim 13, wherein the ranking of the plurality of modified molecules is a ranking from lowest toxicity to highest toxicity.

16. The method of claim 13, wherein outputting data identifying the plurality of modified molecules and the toxicity predictions for the plurality of modified molecules further comprises:
   providing, for display on a user device, a visual representation of a ranked list of the plurality of modified molecules.

17. The method of claim 1, for each of the plurality of modified molecules, generating the respective toxicity prediction for the modified molecule comprises:
   processing a model input that characterizes the modified molecule using a toxicity prediction machine learning model to generate a model output that defines the toxicity prediction for the modified molecule.

18. The method of claim 17, wherein the toxicity prediction machine learning model comprises a decision tree ensemble.

19. A system comprising:
   one or more computers; and
   one or more storage devices communicatively coupled to the one or more computers, wherein the one or more storage devices store instructions that, when executed by the one or more computers, cause the one or more computers to perform operations comprising:
      obtaining data identifying: (i) an input molecule, and (ii) a target molecule fragment of the input molecule;
      generating a set of alternative molecule fragments by performing operations comprising:
         determining, for each candidate molecule fragment in a database of candidate molecule fragments, a respective similarity measure between: (i) an embedding of the target molecule fragment, and (ii) an embedding of the candidate molecule fragment;
         selecting a plurality of candidate molecule fragments from the database of candidate molecule fragments for inclusion in the set of alternative molecule fragments based on the similarity measures; and
         generating data defining a plurality of modified molecules, wherein each modified molecule is a modified version of the input molecule where the target molecule fragment is replaced by a respective alternative molecule fragment from the set of alternative molecule fragments;
      generating a respective toxicity prediction for each of the plurality of modified molecules; and
      outputting data identifying the plurality of modified molecules and the toxicity predictions for the plurality of modified molecules.

20. One or more non-transitory computer storage media storing instructions that when executed by one or more computers cause the one or more computers to perform operations comprising:
   obtaining data identifying: (i) an input molecule, and (ii) a target molecule fragment of the input molecule;
   generating a set of alternative molecule fragments by performing operations comprising:
      determining, for each candidate molecule fragment in a database of candidate molecule fragments, a respective similarity measure between: (i) an embedding of the target molecule fragment, and (ii) an embedding of the candidate molecule fragment;
      selecting a plurality of candidate molecule fragments from the database of candidate molecule fragments for inclusion in the set of alternative molecule fragments based on the similarity measures; and
   generating data defining a plurality of modified molecules, wherein each modified molecule is a modified version of the input molecule where the target molecule fragment is replaced by a respective alternative molecule fragment from the set of alternative molecule fragments;
   generating a respective toxicity prediction for each of the plurality of modified molecules; and
   outputting data identifying the plurality of modified molecules and the toxicity predictions for the plurality of modified molecules.

* * * * *